US009587269B2

(12) United States Patent
Myers et al.

(10) Patent No.: US 9,587,269 B2
(45) Date of Patent: *Mar. 7, 2017

(54) BI-DIRECTIONAL SEQUENCING COMPOSITIONS AND METHODS

(71) Applicant: LIFE TECHNOLOGIES CORPORATION, Carlsbad, CA (US)

(72) Inventors: Jason Myers, Golden, CO (US); Zhoutao Chen, Carlsbad, CA (US); Devin Dressman, Pittsburgh, PA (US); Theo Nikiforov, Carlsbad, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/832,772

(22) Filed: Aug. 21, 2015

(65) Prior Publication Data

US 2015/0353994 A1    Dec. 10, 2015

Related U.S. Application Data

(63) Continuation of application No. 13/543,521, filed on Jul. 6, 2012, now Pat. No. 9,139,874.

(60) Provisional application No. 61/505,420, filed on Jul. 7, 2011, provisional application No. 61/544,992, filed on Oct. 7, 2011, provisional application No. 61/562,252, filed on Nov. 21, 2011, provisional application No. 61/577,637, filed on Dec. 19, 2011.

(51) Int. Cl.
*C12P 19/34* (2006.01)
*C12Q 1/68* (2006.01)

(52) U.S. Cl.
CPC ......... *C12Q 1/6806* (2013.01); *C12Q 1/6869* (2013.01)

(58) Field of Classification Search
USPC ........................................................ 435/91.1
See application file for complete search history.

(56) References Cited

U.S. PATENT DOCUMENTS

2009/0088327 A1    4/2009    Rigatti et al.

FOREIGN PATENT DOCUMENTS

| EP | 0767240 | 4/1997 |
| WO | WO-97/43617 | 11/1997 |
| WO | WO-2004/067764 | 8/2004 |

OTHER PUBLICATIONS

Metzker, Michael, "Sequencing Technologies—the Next Generation", *Nature Reviews Genetics*, 11:, 2010, 31-46.
PCT/US2012/045783, International Search Report and Written Opinion mailed on Nov. 21, 2012.

*Primary Examiner* — Kenneth Horlick

(57) ABSTRACT

In some embodiments, methods for obtaining sequence information from a nucleic acid template linked to a support include hybridizing a first primer to a template strand linked to a support, sequencing a portion of the nucleic acid template, thereby forming an extended first primer product that is complementary to a portion of the nucleic acid template, In some embodiments, the method further includes introducing a nick into a portion of the template strand that is hybridized to the extended first primer product, degrading a portion of the template strand from the nick using a degrading agent, where a portion of the extended first primer remains hybridized to an undegraded portion of the template strand, and sequencing at least some of the single-stranded portion of the extended first primer by synthesis.

9 Claims, 49 Drawing Sheets

| Run | Orientation | %Rev/Fwd >80% | %Paired >75% | MB Q17 40Mb Total | MB Q20 |
|---|---|---|---|---|---|
| 3xEDS washes | | | | | |
| C27-139_C27-140 | forward | 77.21 | 72.25 | 13.99 | 13.24 |
| C27-139_C27-140 | reverse | 77.21 | 93.58 | 10.82 | 10.38 |
| | mean | 77.2 | 82.9 | 24.8 | 23.62 |
| | | | | | |
| C28-90_C28_91 | forward | 79.2 | 73.01 | 15.38 | 14.42 |
| C28-90_C28_91 | reverse | 79.2 | 92.19 | 12.38 | 11.84 |
| | mean | 79.2 | 82.6 | 27.8 | 26.26 |
| | | | | | |
| C29-90_C29-91 | forward | 69.98 | 64.33 | 41.33 | 38.53 |
| C29-90_C29-91 | reverse | 69.98 | 91.92 | 28.7 | 27.42 |
| | mean | 70.0 | 78.1 | 70.0 | 65.95 |
| | | | | | |
| C29-92-C29-93 | forward | 79 | 71.53 | 50.34 | 48.07 |
| C29-92-C29-93 | reverse | 79 | 90.55 | 35.59 | 33.4 |
| | mean | 79.0 | 81.0 | 85.9 | 81.47 |
| | | | | | |
| C30-95_C30-97 | forward | 42.17 | 38.26 | 31.96 | 29.69 |
| C30-95_C30-97 | reverse | 42.17 | 90.73 | 12.56 | 11.67 |
| | mean | 42.2 | 64.5 | 44.5 | 41.36 |
| | | | | | |
| C30-98_C30-99 | forward | 80.44 | 73.58 | 48.19 | 45.85 |
| C30-98_C30-99 | reverse | 80.44 | 91.47 | 36.95 | 35.09 |
| | mean | 80.4 | 82.5 | 85.1 | 80.94 |

FIG. 15A

| Run | Orientation | %Rev/Fwd | %Paired | MB Q17 | MB Q20 |
|---|---|---|---|---|---|
| | | >80% | >75% | 40Mb Total | |

1xEDS wash

| Run | Orientation | %Rev/Fwd | %Paired | MB Q17 | MB Q20 |
|---|---|---|---|---|---|
| C29-100_C29-101 | forward | 81.43 | 76.65 | 24.66 | 23.01 |
| C29-100_C29-101 | reverse | 81.43 | 94.13 | 19.5 | 18.61 |
| | mean | 81.4 | 85.4 | 44.2 | 41.62 |
| C30-104_C30-105 | forward | 81.6 | 75.36 | 41.95 | 39.89 |
| C30-104_C30-105 | reverse | 81.6 | 92.36 | 32.98 | 31.43 |
| | mean | 81.6 | 83.9 | 74.9 | 71.32 |

FIG. 15B

FIG. 17A 1xEnzyme; 1xEDS incubation
2x100 PE run using a 300bp insert Rhodo or DH10B library

| | Auto_C02-325_4357_55737 | Auto_C02-326_4361_55743 |
|---|---|---|
| Bead Density | Loading Density | Loading Density |
| AQ17 Read Lengths | AQ17 Read Lengths | AQ17 Read Lengths |
| Total Number of Reads | 556,982 | 179,936 |
| Filtered 100Q17 Reads | 413,358 | 55,571 |
| 100Q17/50Q17 | 0.89 | 0.65 |
| Mean Length: AQ17 [bp] | 115 | 88 |
| Wells with ISPs: Percentage | 84% | 51% |
| Live ISPs: Percentage | 96% | 77% |
| Key | 59 FWD | 44 REV |

FIG. 17B

2xEnzyme; 1xEDS incubation
2x100 PE run using a 300bp insert Rhodo or DH10B library

| | Auto_C28-112-FWD-AO2_4424_55813 | Auto_C28-113-AO2-REV_4432_55822 |
|---|---|---|
| Bead Density | Loading Density | Loading Density |
| AQ17 Read Lengths | Filtered Q17 Read Length | Filtered Q17 Read Length |
| Total Number of Reads | 517,649 | 337,979 |
| Filtered 100Q17 Reads | 375,972 | 131,940 |
| 100Q17/50Q17 | 0.86 | 0.66 |
| Mean Length: AQ17 [bp] | 117 | 93 |
| Wells with ISPs: Percentage | 83% | 70% |
| Live ISPs: Percentage | 94% | 85% |
| Key | 49 | 36 |
| | FWD | REV |

FIG. 18B 0.05% Tween-20; 1xEDS incubation
2x100 PE run using a 300bp insert Rhodo or DH10B library

| | Auto_C26-250_4397_55783 | Auto_C26-251_AO2-REV_4420_55809 |
|---|---|---|
| Bead Density | Loading Density | Loading Density |
| AQ17 Read Lengths | AQ17 Read Lengths | Filtered Q17 Read Length |
| Total Number of Reads | 485,749 | 382,608 |
| Filtered 100Q17 Reads | 353,187 | 250,438 |
| 100Q17/50Q17 | 0.86 | 0.81 |
| Mean Length: AQ17 [bp] | 118 | 113 |
| Wells with ISPs: Percentage | 80% | 70% |
| Live ISPs: Percentage | 93% | 88% |
| Key | 50 | 40 |
| | FWD | REV |

FIG. 18C 0.4% PVP; 1xEDS incubation
2x100 PE run using a 300bp insert Rhodo or DH10B library

| | Auto_C28-110_4396_55782 | Auto_C28-111_AO2-REV_4423_55812 |
|---|---|---|
| Bead Density | Loading Density | Loading Density |
| AQ17 Read Lengths | AQ17 Read Lengths | Filtered Q17 Read Length |
| Total Number of Reads | 464,633 | 407,233 |
| Filtered 100Q17 Reads | 333,724 | 246,290 |
| 100Q17/50Q17 | 0.85 | 0.80 |
| Mean Length: AQ17 [bp] | 117 | 110 |
| Wells with ISPs: Percentage | 78% | 73% |
| Live ISPs: Percentage | 92% | 90% |
| Key | 47 | 39 |
| | FWD | REV |

FIG. 19C 0.4% PVP;1xEDS incubation
2x100 PE run using a 300bp insert DH10B library

| | Auto_C30-122_AO2-0.4perPVP-<br>12.5u-FWD_4521_55931 | Auto_C30-123_AO2-0.4perPVP-<br>REV_4430_55950 |
|---|---|---|
| Bead Density | Loading Density | Loading Density |
| AQ17 Read Lengths | Filtered Q17 Read Length | Filtered Q17 Read Length |
| Total Number of Reads | 414,302 | 340,572 |
| Filtered 100Q17 Reads | 300,451 | 216,157 |
| 100Q17/50Q17 | 0.83 | 0.79 |
| Mean Length: AQ17 [bp] | 115 | 110 |
| Wells with ISPs: Percentage | 64% | 56% |
| Live ISPs: Percentage | 94% | 85% |
| Key | 42 | 38 |
| | FWD | REV |

FIG. 20B 0.4% PVP, 1xEDS incubation
2x200 PE run using a 300bp insert Rhodo library

| | Auto_C26-260-R134242-RhodoPE_316-_0.4PVP_F_GB_4544_55987 | Auto_C26-261-R134243-RhodoPE_316-_0.4PVP_R_GB_4556_55999 |
|---|---|---|
| Bead Density | Loading Density | Loading Density |
| AQ17 Read Lengths | Filtered Q17 Read Length | Filtered Q17 Read Length |
| Total Number of Reads | 1,683,244 | 900,143 |
| Filtered 100Q17 Reads | 1,224,402 | 418,783 |
| Filtered 200Q17 Reads | 413,980 | 79,566 |
| 100Q17/50Q17 | 0.85 | 0.64 |
| Mean Length: AQ17 [bp] | 153 | 114 |
| Wells with ISPs: Percentage | 64% | 59% |
| Live ISPs: Percentage | 89% | 72% |
| Key | 70 | 50 |
| | FWD | REV |

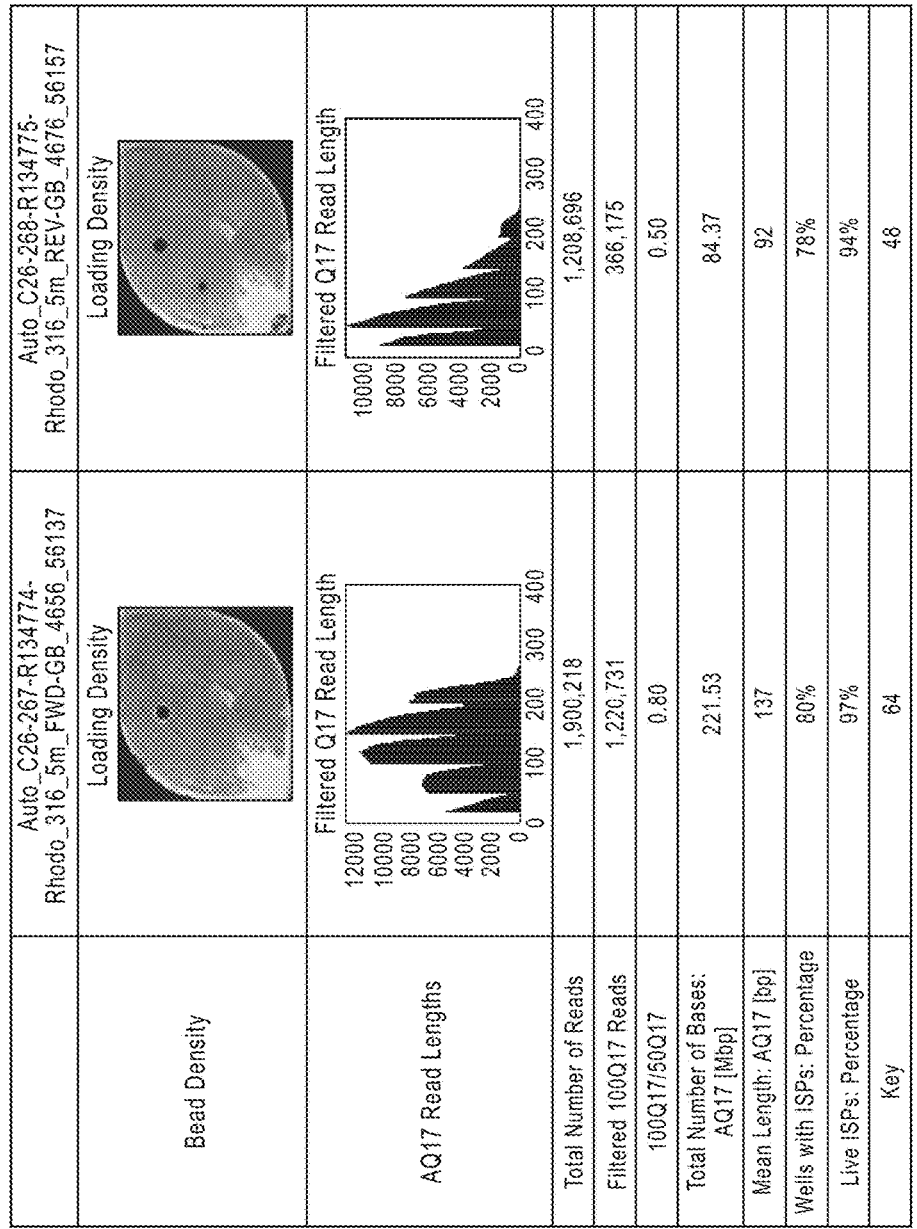
FIG. 21A No 1st EDS; 1xEDS incub.; 0.4% PVP; 5 min Enzyme 2x200 PE run using a 300bp insert Rhodo library

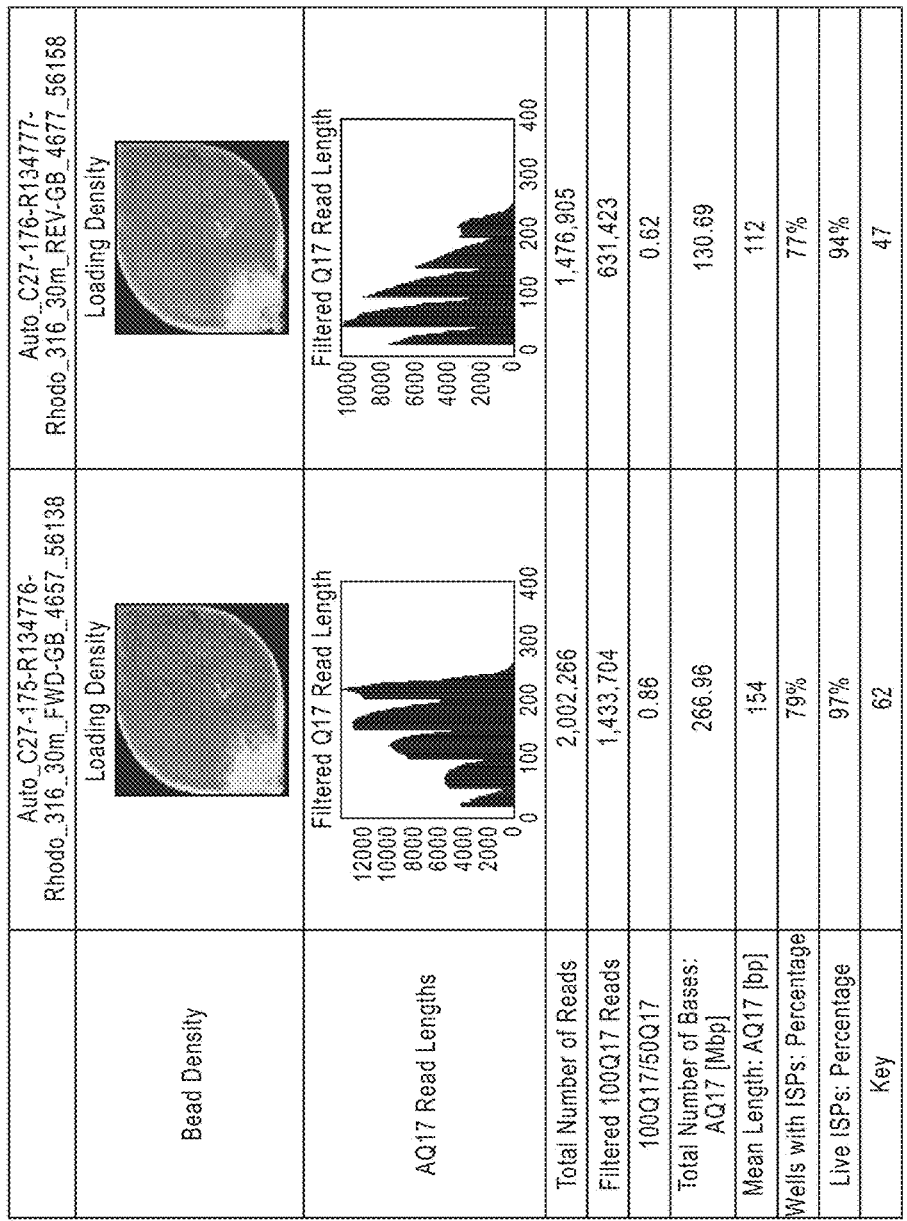
FIG. 21B  No 1st EDS; 1xEDS incub.; 0.4% PVP; 30 min Enzyme 2x200 PE run using a 300bp insert Rhodo library

|  | 5-PSBlock Primer | | SOP Primer | |
| --- | --- | --- | --- | --- |
| Clonal | 70.4% | 74.2% | 69.4% | 73.2% |
| Total Number of Reads | 5,560,328 | 5,262,002 | 5,424,322 | 4,809,786 |
| Filtered 200Q17 Reads | 3,667,458 | 2,751,727 | 3,854,210 | 2,550,760 |
| Filtered 250Q17 Reads | 3,073,815 | 2,098,955 | 3,290,245 | 1,638,172 |
| Filtered 300Q17 Reads | 405,320 | 256,008 | 454,810 | 13,553 |
| Filtered 100Q20 Reads | 4,380,083 | 3,705,597 | 4,446,708 | 3,339,496 |
| Filtered 250Q20 Reads | 2,278,740 | 1,456,789 | 2,660,651 | 1,175,172 |
| Filtered 300Q20 Reads | 33,652 | 183,958 | 359,453 | 9,021 |
| Total Number of Bases: AQ17 [Mbp] | 1185.64 | 979.34 | 1209.27 | 851.62 |
| Total Number of Bases: AQ20 [Mbp] | 1050.21 | 844.02 | 1103.64 | 746.81 |
| Total Number of Bases: Perfect [Mbp] | 765.42 | 604.55 | 825.64 | 543.16 |
| Mean Length: AQ17 (bp) | 227 | 202 | 236 | 196 |
| Mean Length: AQ20 (bp) | 205 | 179 | 220 | 178 |
| Mean Length: Perfect (bp) | 154 | 132 | 170 | 134 |
| 100Q17/50Q17 | 0.92 | 0.88 | 0.94 | 0.88 |
| 200Q17/50Q17 | 0.72 | 0.59 | 0.77 | 0.61 |
| 200Q17/100Q17 | 0.79 | 0.68 | 0.82 | 0.70 |
| 300Q17/100Q17 | 0.09 | 0.06 | 0.10 | 0.00 |
| 300Q17/200Q17 | 0.11 | 0.09 | 0.12 | 0.01 |
| 100Q20/50Q20 | 0.92 | 0.87 | 0.94 | 0.89 |
| 200Q20/50Q20 | 0.65 | 0.53 | 0.73 | 0.56 |
| 200Q20/100Q20 | 0.71 | 0.60 | 0.78 | 0.64 |
| 300Q20/100Q20 | 0.07 | 0.05 | 0.08 | 0.00 |
| 300Q20/200Q20 | 0.10 | 0.08 | 0.10 | 0.00 |

FIG. 23A

|  | 5-PSBlock Primer | | SOP Primer | |
| --- | --- | --- | --- | --- |
| Total Addressable Wells | 11,287,275 | 11,287,275 | 11,287,275 | 11,287,275 |
| Wells with ISPs (%) | 80% | 78% | 79% | 78% |
| Live ISPs (%) | 89% | 83% | 89% | 78% |
| Percent Enrichment | 89% | 83% | 89% | 78% |
| Final Library Reads | 5,560,328 | 5,262,002 | 5,424,322 | 4,809,786 |
| Final Library Reads (%) | 69% | 72% | 68% | 70% |
| Template Bead SNR | 14.31 | 11.94 | 15.67 | 11.47 |
| TauB | 5.41 | 4.23 | 4.47 | 2.96 |
| 10X Coverage Proportional Similarity | 0.9495 | 0.9254 | 0.9515 | 0.9346 |
| GC Percentile Proportional Similarity | 0.9703 | 0.9635 | 0.9697 | 0.9656 |
| Total Non-redundant Start Point Count | 3,910,708 | 3,726,494 | 3,848,842 | 3,472,097 |
| Average Ras Read Accuracy | 98.77% | 98.54% | 99.01% | 98.76% |
| Error Percentage @ 50bp | 0.532% | 0.721% | 0.456% | 0.690% |
| Error Percentage @ 100bp | 0.908% | 1.232% | 0.655% | 1.035% |
| Error Percentage @ 200bp | 1.881% | 2.274% | 1.403% | 1.984% |
| QV Score @ 50bp | 22.74 | 21.42 | 23.41 | 21.61 |
| QV Score @ 100bp | 20.42 | 19.09 | 21.84 | 19.85 |
| QV Score @ 200bp | 17.26 | 16.43 | 18.53 | 17.02 |

|  | C15-470/C15-471 | C16-331/C16-332 |
| --- | --- | --- |
| REV/FWD reads (%) | 94.64 | 88.7 |
| Pairing rate (%) | 87.14 | 82.22 |
| AQ20 throughput (%) | 80.4 | 67.7 |

FIG. 23B

4mM TCEP (Lot# P30347.3W25)

10min

5-PSblock-primer

|  | Auto_C15-470-R148574-L3269_StdF_318_30M-5-block-ak_fwd_10569 | Auto_C15-471-R148575-L3269_StdF_318_30M-ak_rev_148574_10609 |
|---|---|---|
| PGM | C15 | C15 |
| Chip Type | 318C | 318C |
| Chip Barcode | AAQ147415 | AAQ147415 |
| Project |  |  |
| Ref. Library | e_coli_dh10b | e_coli_dh10b |
| Notes | 1T pool48 Lib3269 395bp lr3_a5 lot 1171223-p30427.3w25-5-block | 1T pool48 Lib3269 395bp lr3_a5 lot 1171223-5-blockprimer-sop |
| Run Date | 2012-06-18 11:39:42 | 2012-06-18 18:25:41 |
| Read Length Histogram |  |  |
| Bead Density |  |  |
| Key |  |  |
| Key | 59 | 44 |

FIG. 23C

4mM TCEP (Lot# P30347.3W25)
10min
5-PSblock-primer
| | Auto_C15-470-R148574-L3269_StdF_318_30M-5-block-ak_fwd_10569 | Auto_C15-471-R148575-L3269_StdF_318_30M-ak_rev_148574_10609 |
|---|---|---|
| PGM | C15 | C15 |
| Chip Type | 318C | 318C |
| Chip Barcode | AAQ147415 | AAQ147415 |
| Project | | |
| Ref. Library | e_coli_dh10b | e_coli_dh10b |
| Notes | 1T pool48 Lib3269 395bp lr3_a5 lot 1171223-p30427.3w25-5-block | 1T pool48 Lib3269 395bp lr3_a5 lot 1171223-5-blockprimer-sop |
| Run Date | 2012-06-18 11:39:42 | 2012-06-18 18:25:41 |
| AQ17 Read Lengths | 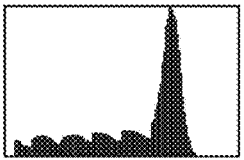 | 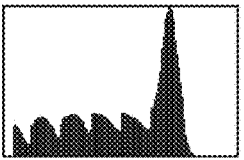 |
| AQ20 Read Lengths |  | 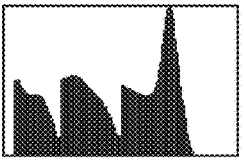 |
| Perfect Read Lengths | 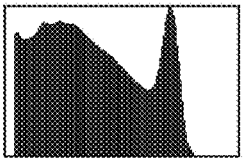 | 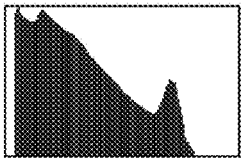 |
| Clonality | 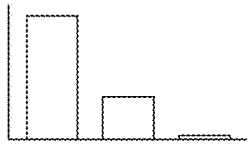 | 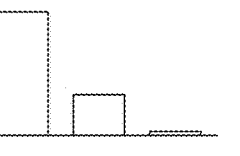 |
| Clonal | 70.4% | 74.2% |
FIG. 23D

4mM TCEP (Lot# P30347.3W25)
10min
SOP primer
| | Auto_C16-331-R148576-L3269_StdF_318_30M-ak_fwd_10568 | Auto_C16-332-R148577-L3269_StdF_318_30M-ak_rev_148576_10608 |
|---|---|---|
| PGM | C16 | C16 |
| Chip Type | 31BC | 31BC |
| Chip Barcode | AAQ147422 | AAQ147422 |
| Project | | |
| Ref. Library | e_coli_dh10b | e_coli_dh10b |
| Notes | 1T pool48 Lib3269 395bp lr3_a5 lot 1171223-p30427.3w25-std | 1T pool48 Lib3269 395bp lr3_a5 lot 1171223-sop |
| Run Date | 2012-06-18 11:40:05 | 2012-06-18 18:25:55 |
| Read Length Histogram | 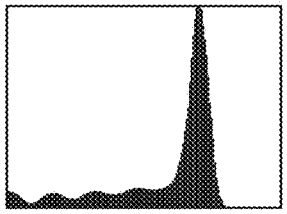 | 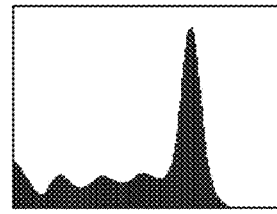 |
| Bead Density | 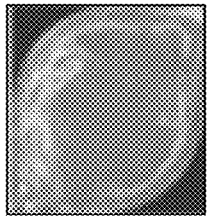 | 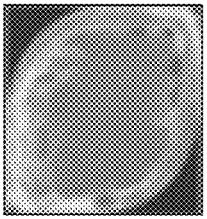 |
| Key | 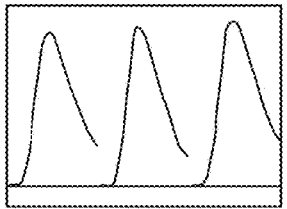 | 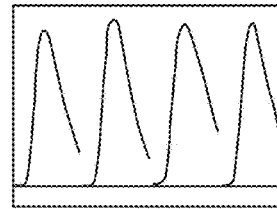 |
| Key | 59 | 41 |
FIG. 23E 4mM TCEP (Lot# P30347.3W25)
10min
SOP-primer
| | Auto_C15-470-R148574-L3269_StdF_318_30M-5-block-ak_fwd_10569 | Auto_C15-471-R148575-L3269_StdF_318_30M-ak_rev_148574_10609 |
|---|---|---|
| PGM | C15 | C15 |
| Chip Type | 31BC | 31BC |
| Chip Barcode | AAQ147415 | AAQ147415 |
| Project | | |
| Ref. Library | e_coli_dh10b | e_coli_dh10b |
| Notes | 1T pool48 Lib3269 395bp lr3_a5 lot 1171223-p30427.3w25-5-block | 1T pool48 Lib3269 395bp lr3_a5 lot 1171223-5-blockprimer-sop |
| Run Date | 2012-06-18 11:39:42 | 2012-06-18 18:25:41 |
| AQ17 Read Lengths | 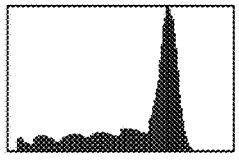 | 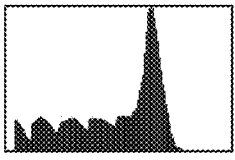 |
| AQ20 Read Lengths | 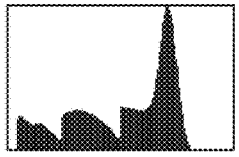 | 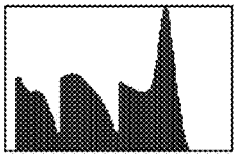 |
| Perfect Read Lengths | 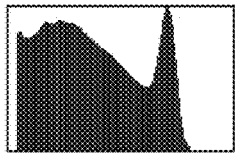 | 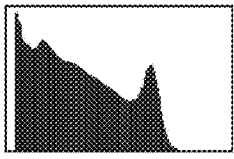 |
| Clonality | 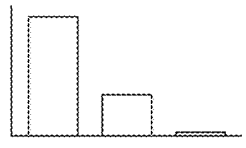 | 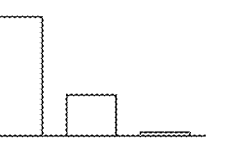 |
| Clonal | 69.4% | 73.2% |
FIG. 23F

BI-DIRECTIONAL SEQUENCING COMPOSITIONS AND METHODS

CROSS REFERENCE TO RELATED APPLICATIONS

This application is a continuation of application Ser. No. 13/543,521, filed Jul. 6, 2012, now U.S. Pat. No. 9,139,874, which claims benefit of priority under 35 U.S.C. §119(e) to U.S. Provisional Application No. 61/505,420, filed Jul. 7, 2011, U.S. Provisional Application No. 61/544,992, filed Oct. 7, 2011, U.S. Provisional Application No. 61/562,252, filed Nov. 21, 2011, and U.S. Provisional Application No. 61/577,637 filed Dec. 19, 2011 entitled "SEQUENCING METHOD AND COMPOSITIONS", the disclosures of which are incorporated herein by reference in their entireties.

SEQUENCE LISTING

This application hereby incorporates by reference the material of the electronic Sequence Listing filed concurrently herewith. The material in the electronic Sequence listing is submitted as a text (.txt) file entitled "LT00545_ST25.txt" created on Jul. 3, 2012, which has a file size of 3 KB, and is herein incorporated by reference in its entirety.

Throughout this application various publications, patents, and/or patent applications are referenced. The disclosures of these publications, patents, and/or patent applications in their entireties are hereby incorporated by reference into this application in order to more fully describe the state of the art to which this invention pertains.

FIELD

In some embodiments, the disclosure relates generally to methods, systems, compositions and kits useful for obtaining sequence information from a nucleic acid molecule. In some embodiments, the methods, systems, compositions and kits are useful for bi-directional sequencing of nucleic acids. In some embodiments, the methods, systems, compositions and kits are useful for generating single stranded polynucleotides. The disclosure also generally relates to sequencing nucleic acids in various orientations, including orientations that are reversed relative to each other. The methods can include sequencing-by-synthesis, paired-end sequencing, or both.

INTRODUCTION

Many nucleic acid sequencing methods involve sequencing-by-synthesis, wherein nucleic acid synthesis is performed via serial incorporation of nucleotides in a template-dependent fashion, typically using a polymerase, and the identity and order of incorporated nucleotides is determined. Recently, label-free methods of sequencing-by-synthesis have been developed, including so-called "ion based" sequencing, wherein one or more byproducts of nucleotide incorporation can be detected electronically using chemically sensitive transistors (e.g., FETs including chemFETs or ISFETs). When performing nucleic acid sequencing, it is frequently desirable to sequence the template strand in both directions. Such bi-directional sequencing can be helpful in increasing the total amount of sequence information available from a given template strand, especially when the length of the template strand exceeds the read lengths typically obtainable from the sequencing method employed. Even in cases where the read lengths of the sequencing method are of the same order as template length, bi-directional sequencing can provide independent validation of sequence information by allowing comparison of the "forward" with the corresponding "reverse" sequence obtained by sequencing the template strand (or its complement) in the opposite direction. While various methods of bi-directional or "paired end" sequencing are known, there remains a need for improved methods, compositions, systems, apparatuses and kits that allow bi-directional sequencing of a template strand.

SUMMARY

Provided herein are compositions, systems, methods and kits for obtaining sequence information from one or more nucleic acid molecules, for example via nucleic acid sequencing.

In some embodiments, the sequencing includes bi-directional sequencing of a nucleic acid molecule of interest.

In some embodiments, the sequencing includes sequencing and obtaining sequencing information in a forward direction, followed by sequencing and obtaining sequence information in a direction that is reversed relative to the forward direction.

In some embodiments, bi-directional sequencing of a nucleic acid molecule can be performed at a single location or at multiple locations along a nucleic acid strand.

In some embodiments, the disclosure relates generally to methods, compositions, systems, apparatuses and kits for obtaining sequence information from a nucleic acid. In some embodiments, the method includes obtaining sequence information from a portion of a nucleic acid. In some embodiments, the method can include obtaining sequencing information for substantially the entire length of the nucleic acid. In some embodiments, obtaining sequencing information can include determining the nucleotide identity of one or more nucleotides along the length of the nucleic acid. In some embodiments, obtaining sequencing information can include determining the nucleotide identity of substantially all of the nucleotides along the length of the nucleic acid. In some embodiments, obtaining sequencing information can include determining the nucleotide identity of substantially all of the nucleotides along the length of the nucleic acid in a first orientation and a second (reversed) orientation relative to the first orientation. In some embodiments, obtaining sequencing information can include determining the nucleotide identity of one or more nucleotides along the length of the nucleic acid in a paired-end sequencing orientation. In some embodiments, obtaining sequencing information can include determining the nucleotide identity of one or more nucleotides along the length of the nucleic acid in a bi-directional sequencing orientation.

In some embodiments, the disclosure relates generally to methods, compositions, systems, apparatuses and kits for obtaining sequence information from at least a portion of a nucleic acid. In some embodiments, obtaining sequencing information can include sequencing by label-free or ion based sequencing methods. In some embodiments, obtaining sequencing information can include labeled or optically detectable based sequencing methods such a fluorescence or bioluminescence. In some embodiments, obtaining sequencing information can include determining the identity of an incorporated nucleotide by monitoring sequencing reaction byproducts released during nucleotide incorporation. In some embodiments, the sequencing reaction byproducts released during nucleotide incorporation can include hydrogen ions, inorganic pyrophosphate or inorganic phosphate.

In some embodiments, the disclosure relates generally to methods, compositions, systems, apparatuses and kits for obtaining sequence information from a nucleic acid via paired-end sequencing. In some embodiments, the nucleic acid can include a DNA, RNA, cDNA, mRNA, or DNA/RNA hybrid. In some embodiments, the nucleic acid can be a target-specific nucleic acid associated with genotyping, such as a nucleic acid containing a single nucleotide polymorphism or a short tandem repeat. In some embodiments, the nucleic acid can be a target-specific nucleic acid associated with one or more medically relevant or medically actionable mutations, such as mutations associated with cancer or inherited disease. In some embodiments, the nucleic acid can be derived from a mammal such as a human.

In some embodiments, the method (and related compositions, systems, apparatuses and kits using the disclosed methods) can include obtaining sequencing information from a nucleic acid linked to a support. Optionally, the support can include any suitable support such as, but not limited to a bead, particle, microparticle, microsphere, slide, flowcell or reaction chamber. In some embodiments, the support can include a solid support. In some embodiments, the support can include a planar support such as a flowcell or slide. In some embodiments, the support can include an Ion Sphere Particle (ISP). In some embodiments, the nucleic acid includes a template strand. In some embodiments, the template strand can further include one or more adaptors. In some embodiments, the one or more adaptors can optionally include a barcode or tagging sequence. In some embodiments, a template strand including an adaptor can further include one or more nucleotide residues that are resistant to a degrading agent. In some embodiments, an adaptor can include one or more phosphorothioate or 2-O-Methyl RNA (2' OMe) nucleotides. In some embodiments, the template strand can be linked to a support through the 5' end of the template strand. In some embodiments, the template strand can be linked to the support through at least one nucleotide in the template strand that is situated 5' of a nick site in the template strand. In some embodiments, the at least one nucleotide in the template strand situated 5' of the nick site can be resistant to a degrading agent. In some embodiments, the at least one nucleotide resistant to a degrading agent includes a phosphorothioate, a 2'OMe residue, or a combination thereof. In some embodiments, the at least one nucleotide resistant to a degrading agent can be located at the 5' end of the template strand, which can optionally include an adaptor. In some embodiments, an adaptor can include the at least one nucleotide resistant to a degrading agent. In some embodiments, an adaptor can link the template strand to the support.

In some embodiments, the disclosure relates generally to methods, compositions, systems, apparatuses and kits for obtaining sequence information from a nucleic acid comprising hybridizing a first primer to the nucleic acid linked to a support and sequencing a portion of the nucleic acid. In some embodiments, the method includes a first primer that is complementary or substantially complementary (e.g., target-specific) to the nucleic acid linked to the support. In some embodiments, the first primer can include a universal or shared primer sequence. In some embodiments, the first primer can include a degenerate primer sequence. In some embodiments, the first primer includes one or more nucleotide analogs. In some embodiments, the first primer is hybridized to the nucleic acid under stringent hybridization conditions. In some embodiments, the first primer contains one or more residues or nucleotides that are resistant to degradation by a degrading agent. In some embodiments, the extended first primer product contains one or more residues or nucleotides that are resistant to degradation by a degrading agent. In some embodiments, the extended first primer product or first primer is nuclease resistant. In some embodiments, the first primer contains one or more residues or nucleotides that are resistant to degradation by an exonuclease. In some embodiments, the first primer contains one or more phosphorothioates, 2'OMe residues, or a combination thereof.

In some embodiments, the first primer is hybridized to the distal end of a nucleic acid, where the proximal end of the nucleic acid is attached to a support. In some embodiments, the first primer is hybridized to the proximal end of a nucleic acid, where the distal end of the nucleic acid is attached to a support. In some embodiments, the first primer is extended via template-dependent nucleic acid synthesis. In some embodiments, the method includes sequencing by synthesis. In some embodiments, the method includes sequencing by ligation. In some embodiments, the method includes sequencing by hybridization. In some embodiments, the sequencing includes sequencing via template dependent nucleic acid synthesis.

In some embodiments, the method includes forming an extended first primer product that is complementary or substantially complementary to a portion of the nucleic acid. In some embodiments, the extended first primer product is complementary or substantially complementary to all of the nucleotides in the nucleic acid. In some embodiments, the sequencing information obtained can determine substantially all of the nucleotides in the nucleic acid or the extended first primer product. In some embodiments, the extended first primer product can be cross-linked to a support. In some embodiments, the extended first primer product can be cross-linked to a support that is different to a support linked to the template strand. In some embodiments, the extended primer product can be separated from the template strand prior to cross-linking to a support. In some embodiments, the extended primer product can be cross-linked to a support prior to introducing the nick or degrading step. In some embodiments, the extended primer product can be cross-linked to a support shared with the template strand. In some embodiments, the extended primer product can be photo-chemically cross-linked to a support. In some embodiments, the template strand can be removed or degraded after linking the extended primer product to a support.

In some embodiments, the method can include sequencing a portion a nucleic acid template by synthesis, where the sequencing by synthesis includes extending the first primer via template-dependent nucleic acid synthesis. In some embodiments, the method can include sequencing a portion of a nucleic acid, optionally linked to a support, where the sequencing includes extending the first primer via sequencing by hybridization or sequencing by ligation. In some embodiments, the sequencing can include sequencing at least some of the single-stranded portion of the extended first primer by extending the free 3' end of the nick. In some embodiments, extending the free 3' end of the nick can include sequencing via nucleic acid synthesis, thereby synthesizing a nucleic acid molecule that is complementary to at least some of the single-stranded portion of the extended first primer. In some embodiments, sequencing at least some of the single-stranded portion of the extended first primer product can include hybridizing a reverse primer to a sequence within the single-stranded portion of the extended first primer product. In some embodiments, hybridizing a reverse primer to a sequence within the single stranded portion of the extended first primer product can include extending the reverse primer using a polymerase. In some embodiments, the reverse primer can include one or more nucleotides resistant to degradation by a degrading agent. In some embodiments, the reverse primer is nuclease resistant. In some embodiments, the reverse primer contains one or more residues or nucleotides that are resistant to degradation by an exonuclease. In some embodiments, the reverse primer contains one or more phosphorothioates, 2'OMe residues, or a combination thereof.

In some embodiments, the method (and related kits, compositions and apparatus using the disclosed methods) can include introducing a nick into a portion of the template strand that is hybridized to the extended first primer product. In some embodiments, the nick includes a free 5' end and a free 3' end in the template strand. In some embodiments, a plurality of nicks can be introduced into the portion of the template strand that is hybridized to the extended first primer. In some embodiments, introducing one or more nicks can include introducing a gap along the template strand. In some embodiments, introducing a site-specific nick can include introducing a site-specific gap along the template strand. In some embodiments, one or more nicks can be introduced randomly along the length of the template strand. In some embodiments, one or more nicks can be introduced at site-specific locations along the length of the template strand. In some embodiments, one or more nicks can be introduced into the extended primer product and the template strand. In some embodiments, one or more nicks can be introduced into the template strand, which optionally includes one or more adaptors. In some embodiments, one or more nicks can be introduced into the template strand and the extended primer product, however it is preferred that the nicks are not positioned as to introduce a double stranded break. In some embodiments, a nickase can be used to introduce one or more nicks in the template strand or the extended primer product. In some embodiments, a restriction enzyme can be used to introduce one or more nicks into the template strand or extended primer product. In some embodiments, one or more nicks can be introduced into the template strand using a uracil DNA glycosylase. In some embodiments, the template strand can include at least one adaptor, where the adaptor can include one or more nicks.

In some embodiments, the method can further include degrading a portion of the template strand from the free 5' end of the nick using a degrading agent. In some embodiments, the method can include degrading a portion of the template strand from the free 5' end of the nick using a degrading agent, thereby generating a single-stranded portion of the extended first primer product. In some embodiments, the degrading agent can include an enzymatic, thermal or chemical treatment. In some embodiments, the degrading agent can include an exonuclease. Optionally, the degrading agent can include a 5'-3' exonuclease. In some embodiments, the degrading can further include digesting the template strand from the free 5' end of the nick using the 5'-3' exonuclease. In some embodiments, the degrading agent can include an exonuclease in combination with an endonuclease. In some embodiments, the degrading agent can include a heat treatment.

In some embodiments, a portion of the extended first primer product can remain hybridized to an undegraded portion of the template strand. In some embodiments, the extended first primer product that remains hybridized to an undegraded portion of the template strand can undergo sequencing. In some embodiments, the extended first primer product that remains hybridized to an undegraded portion of the template can undergo separation from the undegraded template prior to sequencing. In some embodiments, a separated extended first primer product can be captured by a binding partner or capture probe. In some embodiments, a captured or bound extended primer product can be sequenced by any suitable sequencing means. In some embodiments, the sequencing can include sequencing by synthesis, sequencing by ligation and/or sequencing by hybridization.

In some embodiments, the disclosure relates generally to methods, compositions, systems, apparatuses and kits for nucleic acid sequencing. In some embodiments, the method (and related kits, compositions and apparatuses using the method) can include hybridizing a first primer to a distal end of a nucleic acid strand having a distal and proximal end, where the proximal end of the nucleic acid strand is linked to a solid support. In some embodiments, the method can further include extending the hybridized first primer in the direction of the proximal end of the nucleic acid strand and the solid support, thereby forming an extended first primer product that is complementary to a portion of the nucleic acid strand and obtaining a first sequencing read. In some embodiments, the method can further include introducing a site-specific nick into the proximal end of the nucleic strand hybridized to the extended first primer product. Optionally, the method can further include degrading a portion of the nucleic acid strand, thereby generating a single-stranded portion within the extended first primer product, wherein a portion of the extended first primer product remains hybridized to the nucleic acid strand. In some embodiments, the method can further include extending the single-stranded portion within the extended first primer product, thereby obtaining a second sequencing read. In some embodiments, the method can further include consolidating the first and second sequencing read. In some embodiments, the consolation can including aligning the first and second sequencing read against a reference sample. In some embodiments, the reference sample is a human sample. In some embodiments, the reference sample is hg19. In some embodiments, the aligning can identity a mismatch, deletion, insertion or translocation or variations in the nucleic acid strand. In some embodiments, aligning the first and second sequencing reads against a reference sequence can determine the presence of a deletion, insertion, translocation, inversion, variation, mutation or mismatch in the nucleic acid strand.

In some embodiments, the disclosure relates generally to methods, compositions, systems and apparatuses for bi-directional sequencing of a nucleic acid. In some embodiments, a method for obtaining bi-directional sequence information from a nucleic acid molecule can include hybridizing a first primer to a nucleic acid molecule, sequencing a portion of the nucleic acid molecule, wherein the sequencing includes extending the first primer, thereby forming an extended first primer product that is complementary to a portion of the nucleic acid molecule. In some embodiments, the extended first primer product can be substantially complementary to the nucleic acid molecule. In some embodiments, the extending can include extending via template-dependent nucleic acid synthesis. In some embodiments, the method can further include introducing a nick into a portion of the nucleic acid molecule that is hybridized to the extended first primer product. In some embodiments, a plurality of nicks can be introduced into the nucleic acid molecule. In some embodiments, one or more nicks are introduced into the 5'end of the nucleic acid molecule. In some embodiments, the nick can include a free 5' end and a free 3' end in the nucleic acid molecule. In some embodiments, the method can further include degrading a portion of the nucleic acid molecule from the free 5' end of the nick using a degrading agent, thereby generating a single-stranded portion of the extended first primer product. In some embodiments, the extended first primer product can remain hybridized to an undegraded portion of the nucleic acid molecule. In some embodiments, the method further includes sequencing at least some of the single-stranded portion of the extended first primer product. In some embodiments, the sequencing can include sequencing by synthesis, sequencing by ligation and/or sequencing by ligation. In some embodiments, the nucleic acid molecules is linked to a support, such as but not limited to a solid support. In some embodiments, the nucleic acid molecule is a single-stranded template. In some embodiments, the nucleic acid molecule is a double-stranded template that can undergo a denaturation treatment to form a single stranded template.

In some embodiments, the disclosure relates generally to kits (and methods, compositions, apparatuses and systems that use the kits) including a primer having an exonuclease resistant nucleotide sequence substantially complementary to a template nucleic acid to be sequenced. In some embodiments, the kit can include a primer that is complementary to the template nucleic acid to be sequenced. In some embodiments, the primer can include one or more phosphorothioate or 2' OMe residues. In some embodiments, the kit can further include one or more polymerases, one or more dNTPs, one or more nicking enzymes and one or more degrading enzymes. In some embodiments, the kit can include one or more DNA polymerases, such as a native polymerase, mutant polymerase, genetically engineered DNA polymerase or fragment thereof, where the fragment is capable of catalyzing polymerization. In some embodiments, the polymerase can include a thermostable polymerase. In some embodiments, the kit can include one or more ddNTPs for terminating polymerization. In some embodiments, the nicking agent can include a nickase. In some embodiments, the nicking agent can be a uracil DNA glycosylase. In some embodiments, the degrading agent can include an exonuclease, optionally in combination with an endonuclease. In some embodiments, the kit can further include one or more buffers, cations, salts, additives, reducing agents and/or supports. In some embodiments, the kit can further include a capture or binding partner. In some embodiments, the kit can further include a standard or control nucleic acid molecule and/or instructions as to use the kit.

In some embodiments, the disclosure relates generally to methods (and related compositions, kits, systems and apparatuses using the methods) for improving nucleic acid sequencing accuracy. In some embodiments, the method includes hybridizing a first primer to a distal end of a nucleic acid strand having a distal and proximal end. Optionally, the method includes linking the proximal end of the nucleic acid strand to a solid support. In some embodiments, the method further includes extending the hybridized first primer in the direction of the proximal end of the nucleic acid strand (and optionally the solid support), thereby forming an extended first primer product that is complementary to a portion of the nucleic acid strand and obtaining a first sequencing read. In some embodiments, the method can further include introducing a site-specific nick into the proximal end of the nucleic strand hybridized to the extended first primer product. In some embodiments, a site-specific nick can be introduced to the 5' end of the nucleic acid strand hybridized to the extended first primer product. In some embodiments, a nick can be introduced into an adaptor that is linked to the proximal end of the nucleic acid strand. In some embodiments, the method can further include degrading a portion of the nucleic acid strand, thereby generating a single-stranded portion within the extended first primer product. In some embodiments, a portion of the extended first primer product can remain hybridized to the nucleic acid strand. In some embodiments, the method can further include extending the single-stranded portion within the extended first primer product, thereby obtaining a second sequencing read. In some embodiments, the method can include aligning the first and second sequencing read to obtain a nucleic acid sequence with improved accuracy. In some embodiments, obtaining a first and second sequencing read results in improved sequencing accuracy and/or sequencing throughput. In some embodiments, obtaining a first and second sequencing read can include generating greater than 1 gigabyte of sequencing data in a first and second orientation. In some embodiments, obtaining a first and second sequencing read can include generating greater than 1 gigabyte of sequencing data in each of a first and second orientation. In some embodiments, obtaining a first and second sequencing read can include greater than 1 gigabyte of sequencing data in a first orientation and greater than 1 gigabyte of sequencing data in a reverse orientation as compared to the first sequencing read. In some embodiments, obtaining a first and second sequencing read can include greater than 1 gigabyte of sequencing data in a first orientation at AQ20 and greater than 1 gigabyte of sequencing data in a reverse orientation at AQ20 as compared to the first sequencing read. In some embodiments, obtaining a first and second sequencing read can include greater than 1 gigabyte of sequencing data in a first orientation at AQ17 and greater than 1 gigabyte of sequencing data in a reverse orientation at AQ17 as compared to the first sequencing read.

In some embodiments, the sequencing can include hybridizing a first primer to a template strand. Optionally, the sequencing can include extending the first primer, thereby generating an extended first primer product. Extending the first primer can include obtaining sequence information in the "forward" or first direction. Extending the first primer can include using one or more enzymes. Optionally, the template strand can be linked to a support.

In some embodiments, the sequencing can include degrading at least some portion of the template strand. In some embodiments, the degrading can including degrading a portion of the template strand that is hybridized to the extended first primer product. The degrading can include using one or more degrading agents. In some embodiments, the degrading agent specifically degrades the template strand but not the extended first primer strand, thereby generating a single-stranded region within the extended first primer product. In some embodiments, the template strand can be degraded using a nicking enzyme, optionally in the presence of an exonuclease. The single-stranded region within the extended first primer product can optionally be used as a template for template-dependent nucleotide incorporation. Such template-dependent nucleotide incorporation can include catalyzing template dependent nucleotide incorporation using one or more enzymes, thereby obtaining sequence information in the "reverse" or second direction. In some embodiments, template-dependent nucleotide incorporation of the single-stranded region within the extended first primer product can include generating an extended second nucleic acid molecule that is substantially complementary to the extended first primer product over at least some portion of their respective lengths.

In some embodiments, the disclosed methods for bi-directional sequencing of nucleic acids comprise two or more sequencing reactions performed serially on the same template nucleic acid molecule. In some embodiments, the disclosed methods for bi-directional sequencing can include one or more hybridization reactions, extension reactions, sequencing reactions, and degradation reactions. In some embodiments, the disclosed methods for bi-directional sequencing can include a single hybridization reaction. In some embodiments, the disclosed methods for bi-directional sequencing can be performed using a single primer. Optionally, the single primer can be hybridized to the template strand and extended by template dependent nucleotide incorporation in the presence of a polymerase. In some embodiments, a hybridization reaction can introduce and/or hybridize a primer to a complementary sequence along the template strand. An extension reaction can attach or incorporate nucleotides using one or more enzymes to extend the primer sequence. Such attachment or incorporation can optionally occur in template-dependent fashion. In some embodiments, a sequencing reaction can determine the base identity of one or more nucleotides incorporated into an extending or newly synthesized nucleic acid molecule (e.g., an extending or newly synthesized primer or template strand) in an extension reaction and therefore determine sequence information relating to the extending or newly synthesized strand. The sequencing reaction can be performed in a forward and/or reverse direction (i.e., bi-directional). In some embodiments, the sequencing reaction can be performed in a first orientation, optionally followed by a second sequencing reaction in an orientation that is reversed relative to the first orientation. In some embodiments, the sequencing reaction includes determining the identity of nucleotides incorporated during the sequencing reaction. In some embodiments, a degradation reaction can include the use of one of more degrading agents to degrade at least some portion of a strand of the nucleic acid molecule to be degraded. In some embodiments, the degrading can occur near a site of attachment or action of the degrading agent. In some embodiments, the degrading reaction can degrade one or more nucleotides at one or more degradation sites along the nucleic acid molecule to be degraded. In some embodiments, the degrading agent can generate one or more single-stranded regions within the nucleic acid molecule. In some embodiments, the single-stranded regions can be extended using one or more enzymes and optionally, the extended primer product as a template for extension. Optionally, extension of the single-stranded regions can be coupled to a sequencing reaction to determine the nucleotide identity of one or more nucleotides incorporated into the extended nucleic acid molecule.

Methods for bi-directional sequencing of nucleic acids can be practiced on any nucleic acid, including DNA, cDNA, RNA, RNA/DNA hybrids, and nucleic acid analogs. These and other features are provided herein.

DRAWINGS

Figure 9:
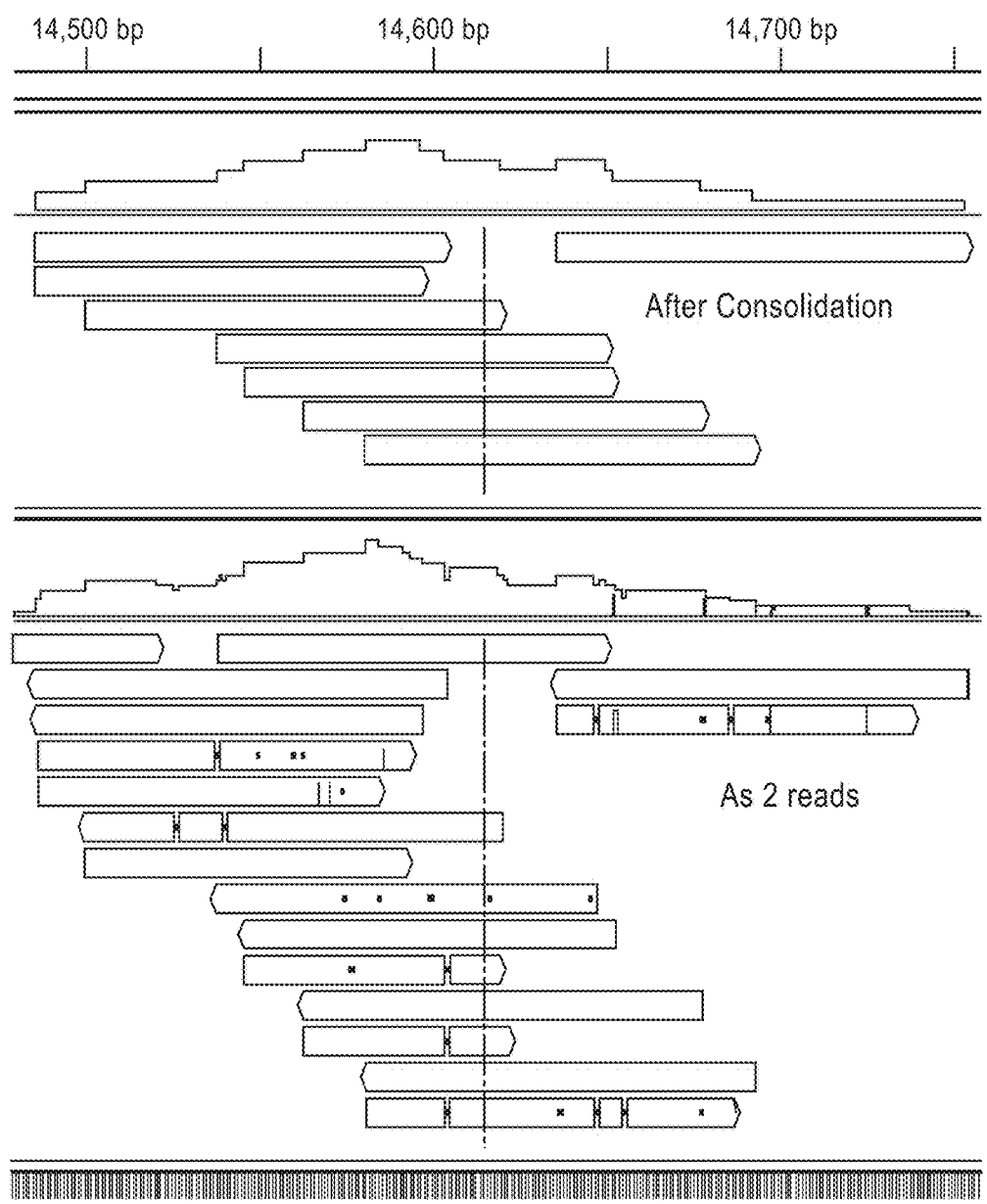

FIG. 9 discloses dual (2 reads) and consolidated reads obtained using an exemplary paired-end sequencing method according to the disclosure from a mapped region of the genome. An overall improvement in accuracy is obtained using the exemplary paired-end sequencing method according to the disclosure.

Figure 10A:
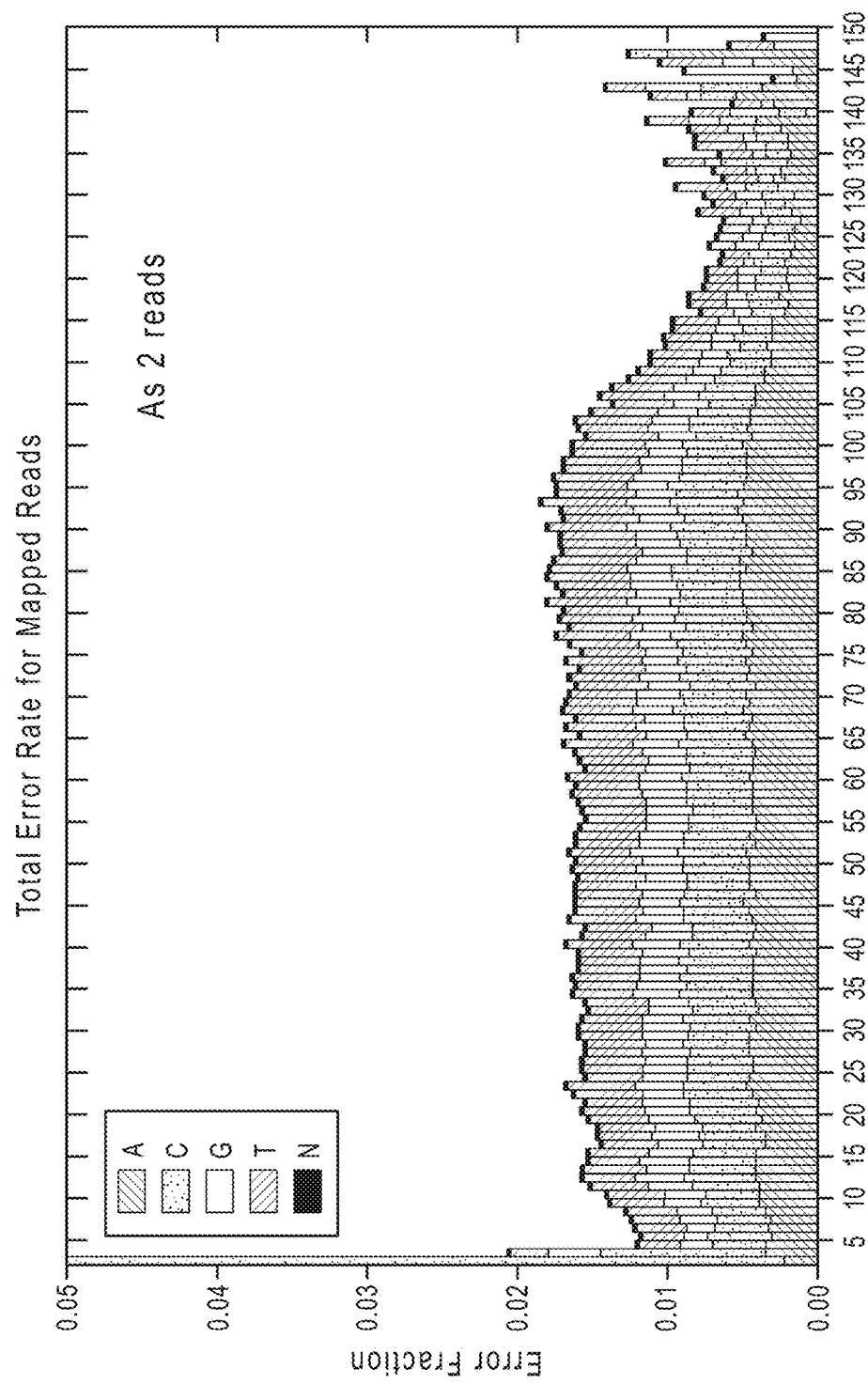

FIG. 10A is a graph disclosing total error rate for dual reads (2 reads) obtained using an exemplary paired-end sequencing method according to the disclosure.

Figure 10B:
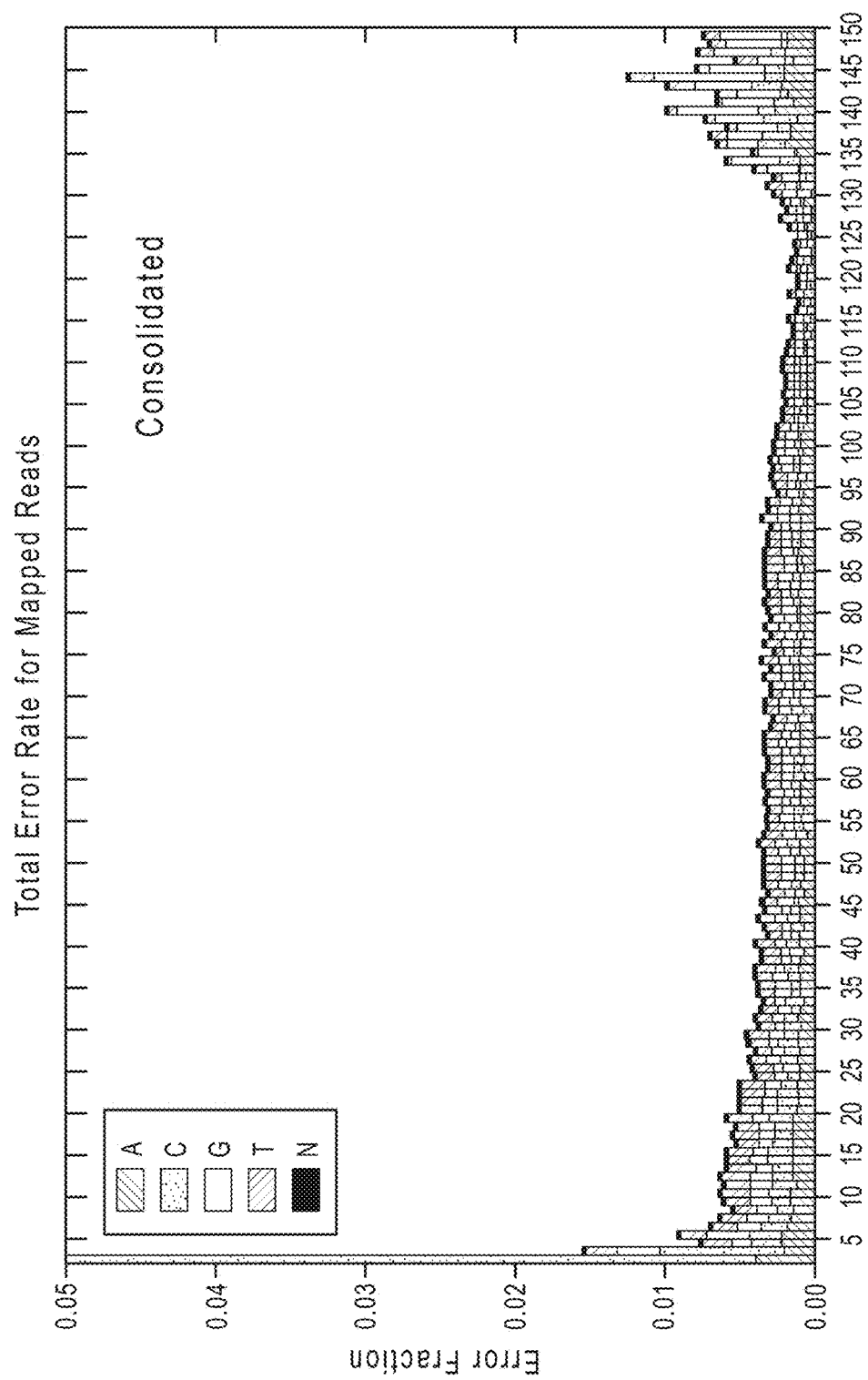

FIG. 10B is a graph disclosing total error rate for consolidated reads obtained using an exemplary paired-end sequencing method according to the disclosure.

Figure 11A:
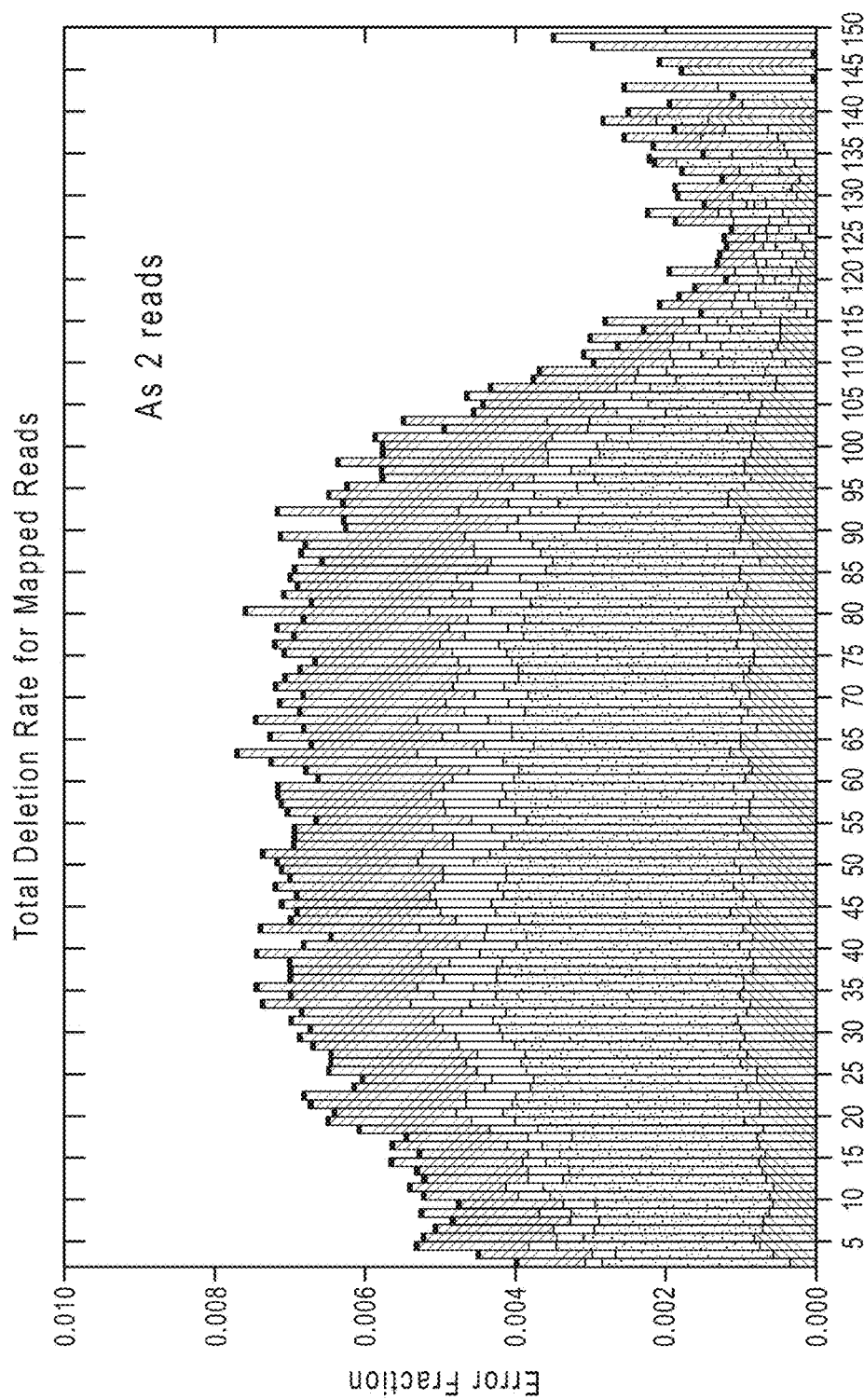

FIG. 11A is a graph disclosing total deletion rate for dual reads (2 reads) obtained using an exemplary paired-end sequencing method according to the disclosure.

Figure 11B:
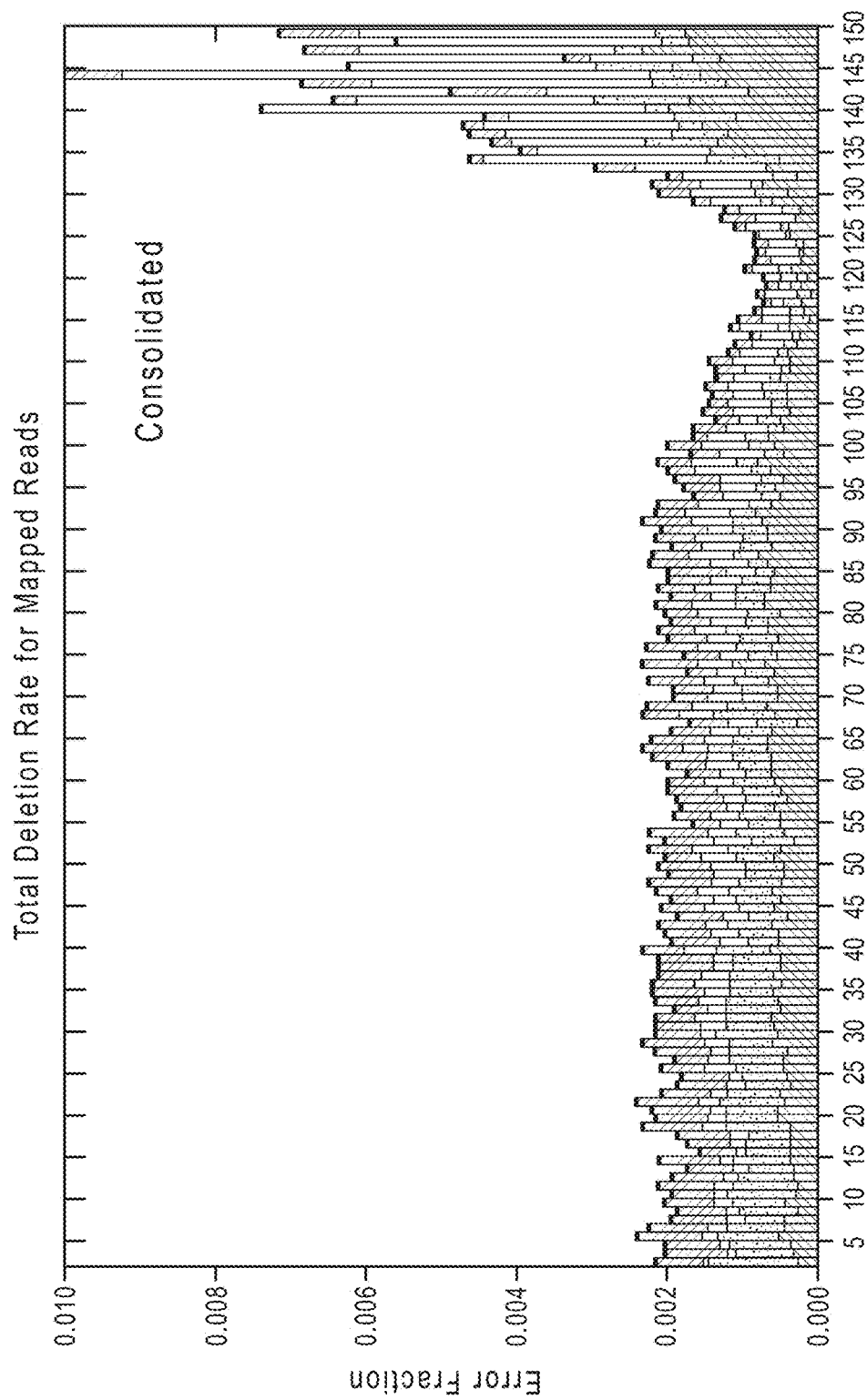

FIG. 11B is a graph disclosing total deletion rate for consolidated reads obtained using an exemplary paired-end sequencing method according to the disclosure.

Figure 12A:
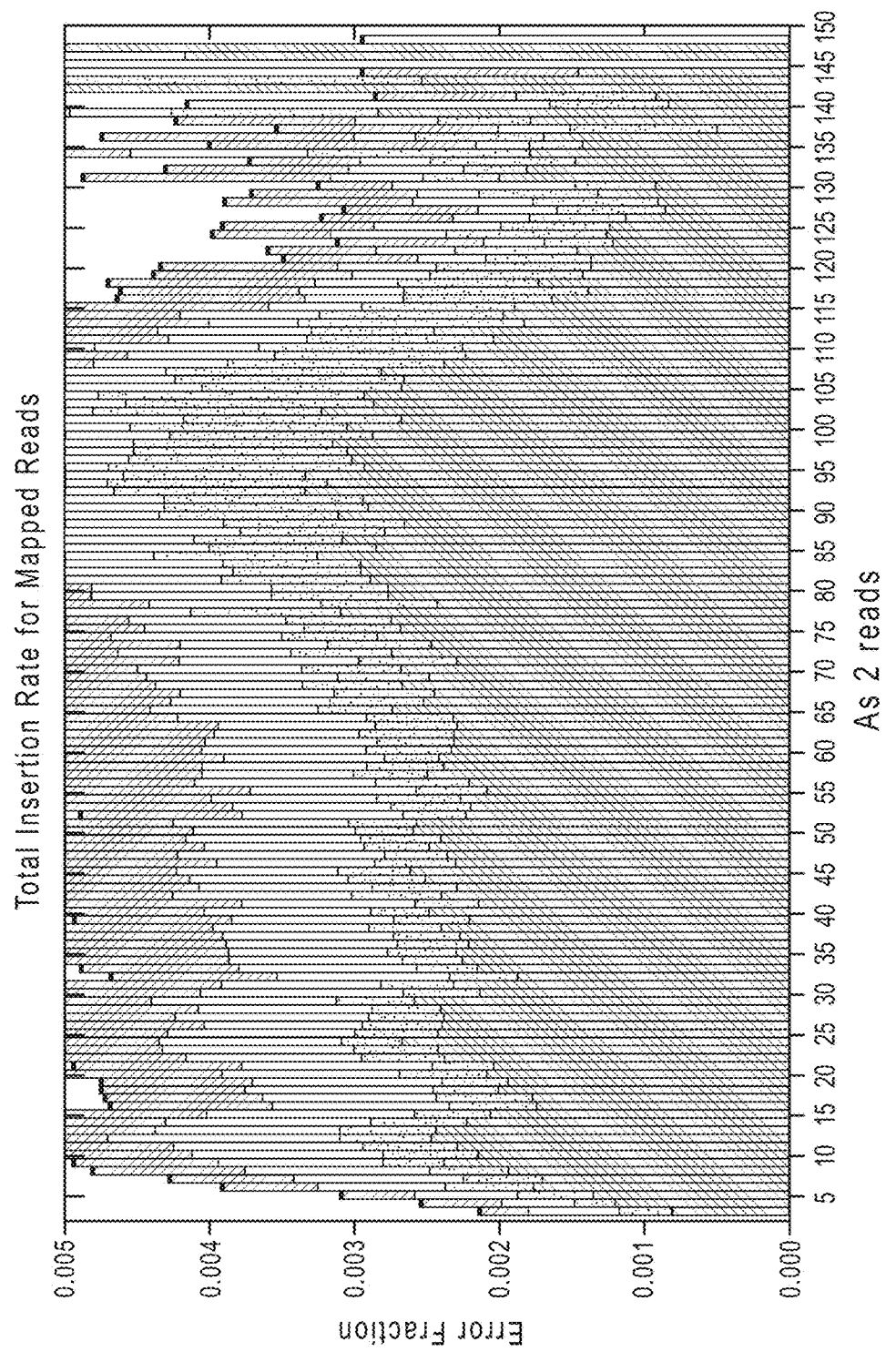

FIG. 12A is a graph disclosing total insertion rate for dual reads (2 reads) obtained using an exemplary paired-end sequencing method according to the disclosure.

Figure 12B:
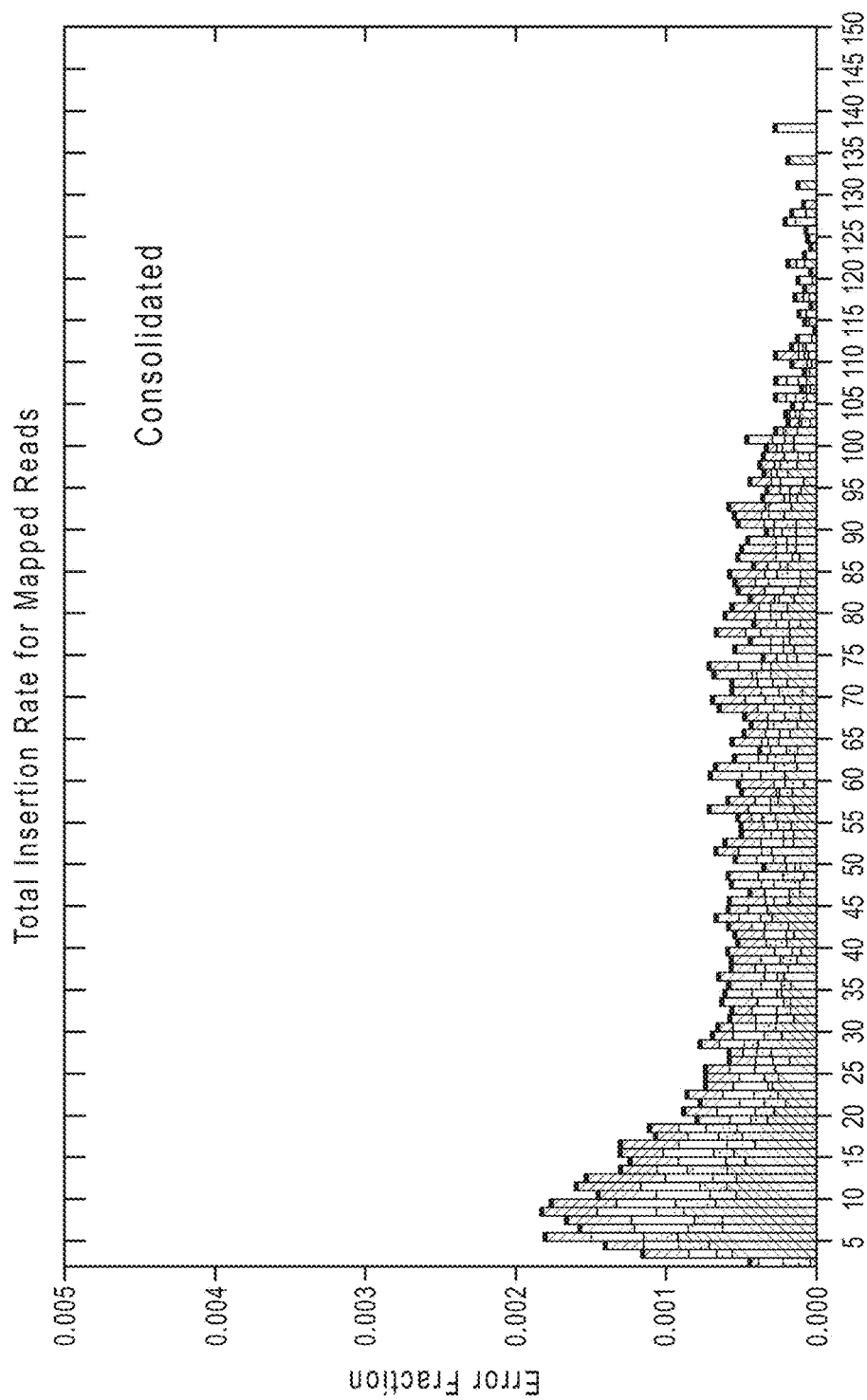

FIG. 12B is a graph disclosing total insertion rate for consolidated reads obtained using an exemplary paired-end sequencing method according to the disclosure.

Figure 13A:
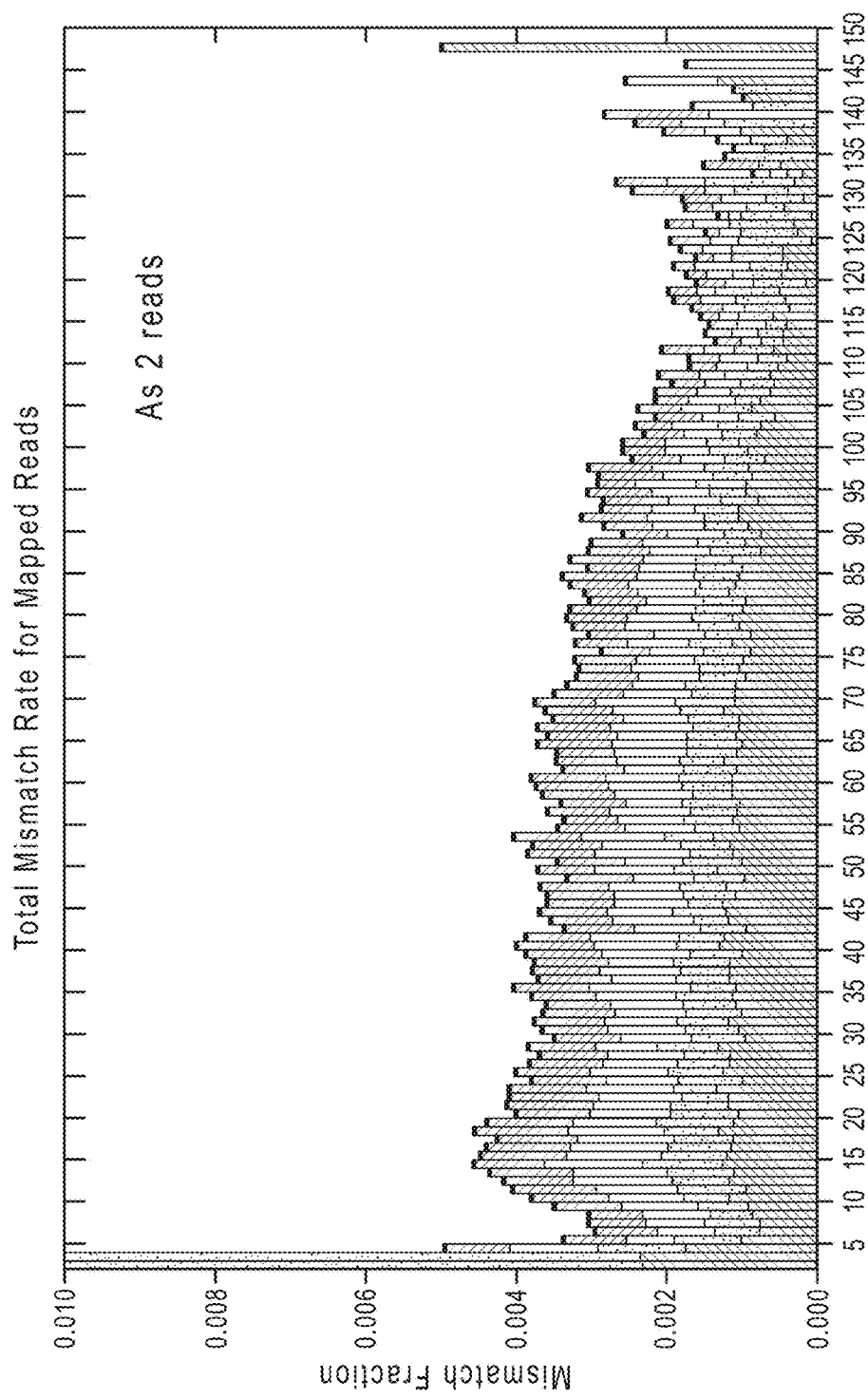

FIG. 13A is a graph disclosing total mismatch rate for dual reads (2 reads) obtained using an exemplary paired-end sequencing method according to the disclosure.

Figure 13B:
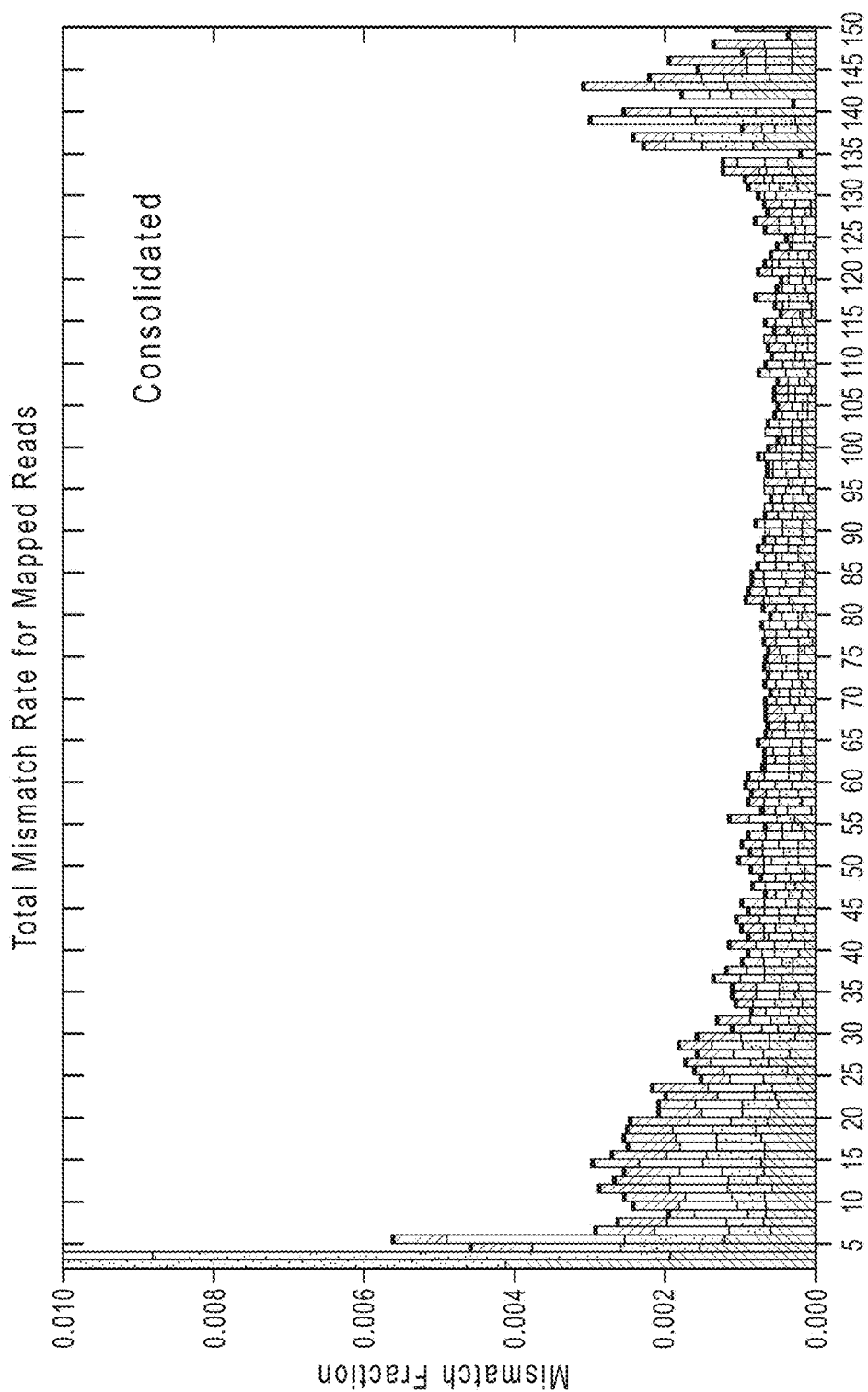

FIG. 13B is a graph disclosing total mismatch rate for consolidated reads obtained using an exemplary paired-end sequencing method according to the disclosure.

Figure 14:
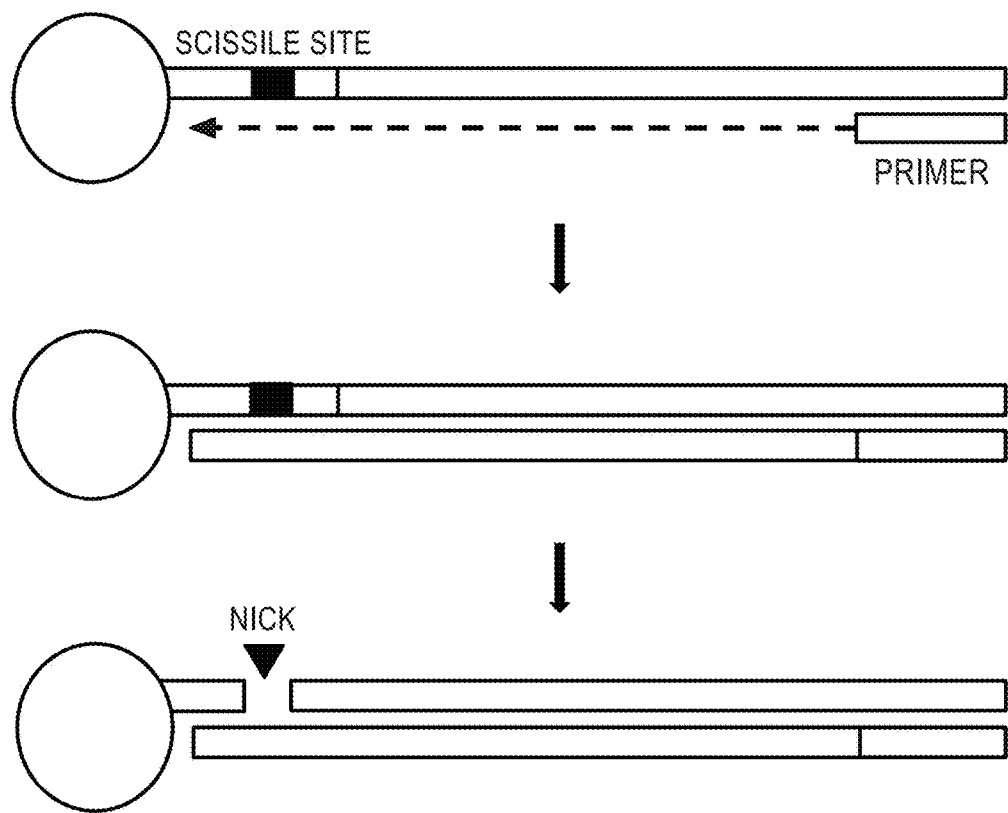

FIG. 14 is a schematic depicting an exemplary embodiment of a paired-end sequencing method according to the disclosure.

FIG. 15A provides data obtained using an exemplary paired-end sequencing method according to the disclosure.

FIG. 15B provides data obtained using an exemplary paired-end sequencing method according to the disclosure.

Figure 16A:
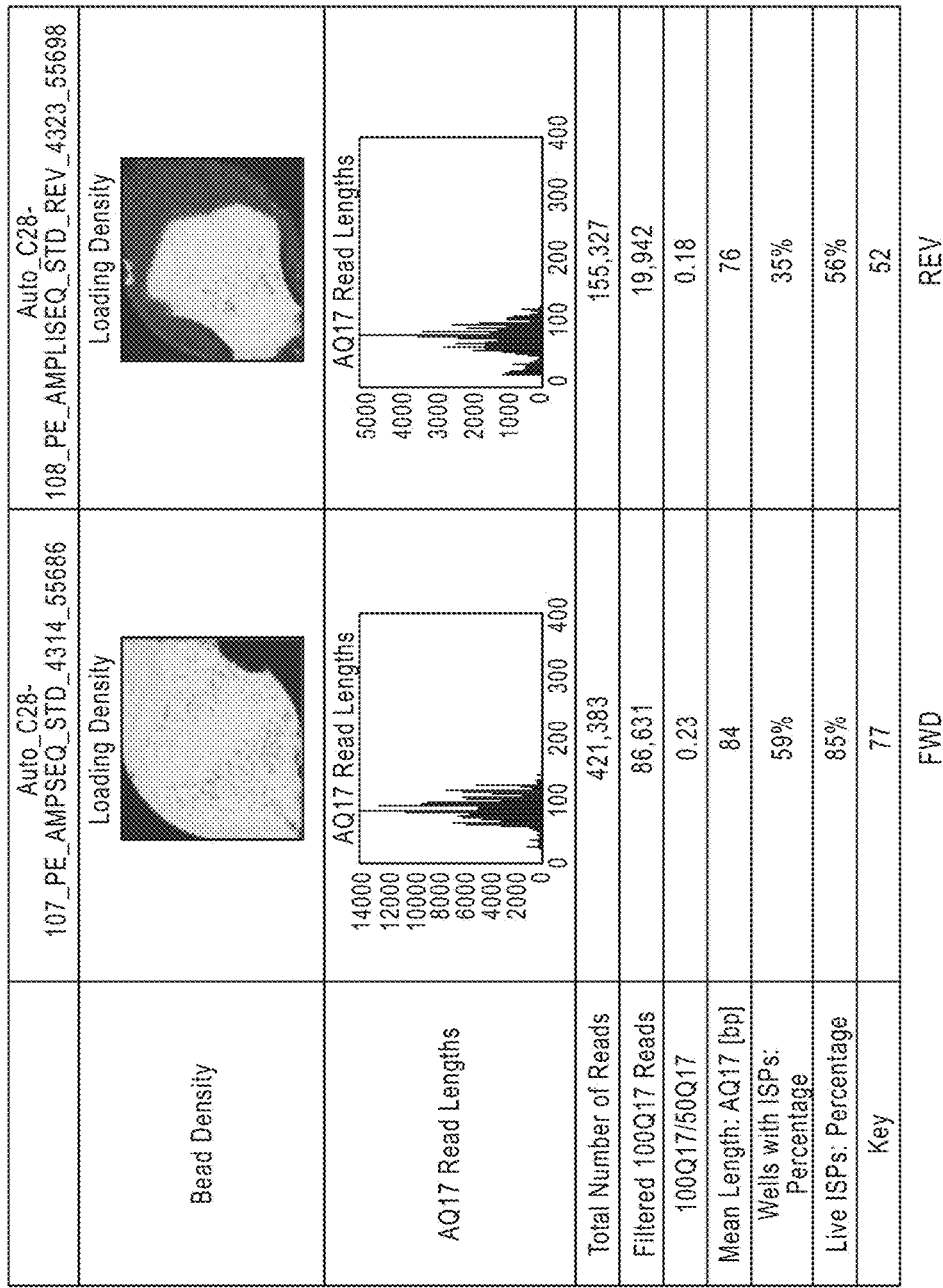

FIG. 16A provides data obtained using an exemplary paired-end sequencing method according to the disclosure.

Figure 16B:
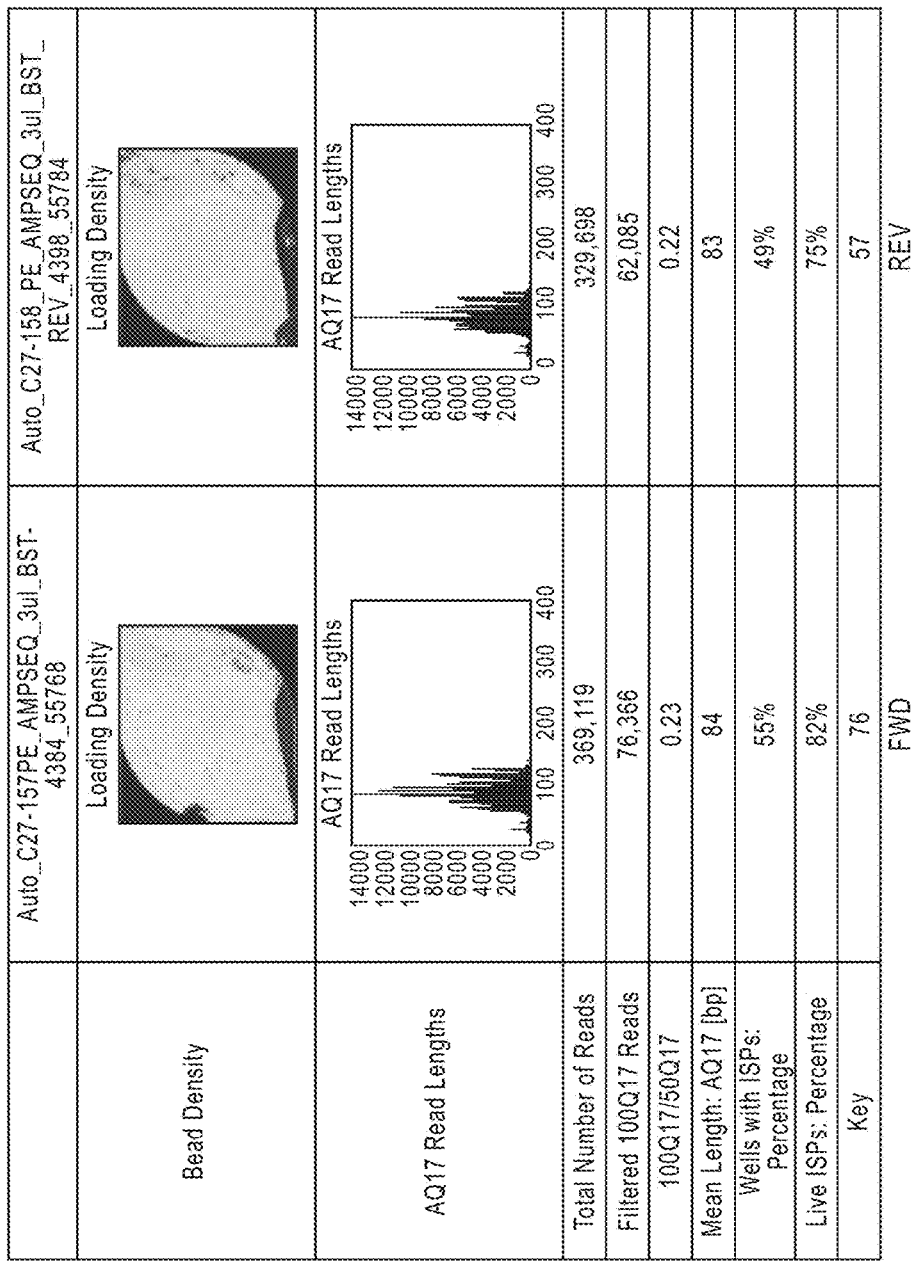

FIG. 16B provides data obtained using an exemplary paired-end sequencing method according to the disclosure.

FIG. 17A provides data obtained using an exemplary paired-end sequencing method according to the disclosure.

FIG. 17B provides data obtained using an exemplary paired-end sequencing method according to the disclosure.

Figure 18A:
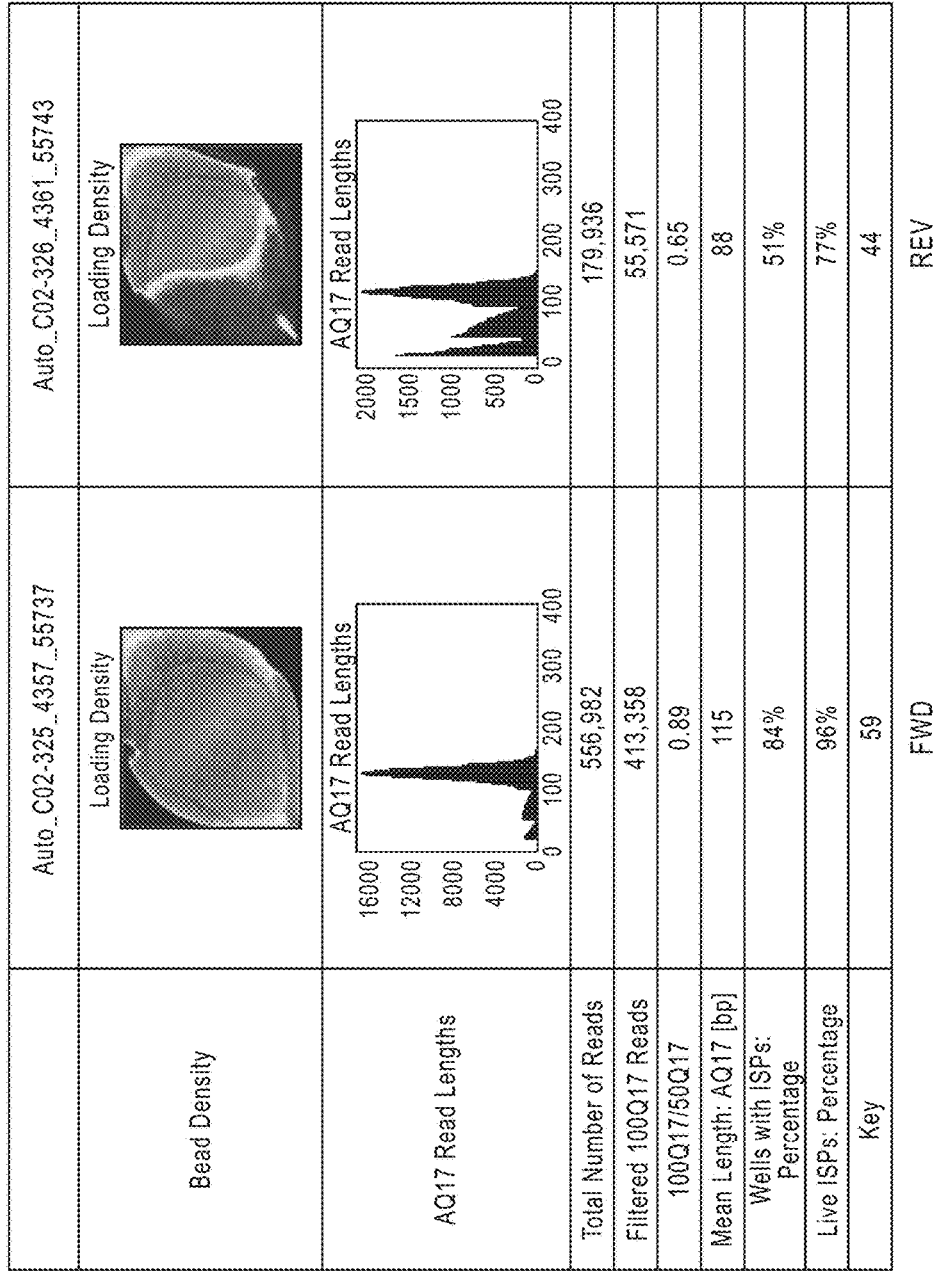

FIG. 18A provides data obtained using an exemplary paired-end sequencing method according to the disclosure.

FIG. 18B provides data obtained using an exemplary paired-end sequencing method according to the disclosure.

FIG. 18C provides data obtained using an exemplary paired-end sequencing method according to the disclosure.

Figure 19A:
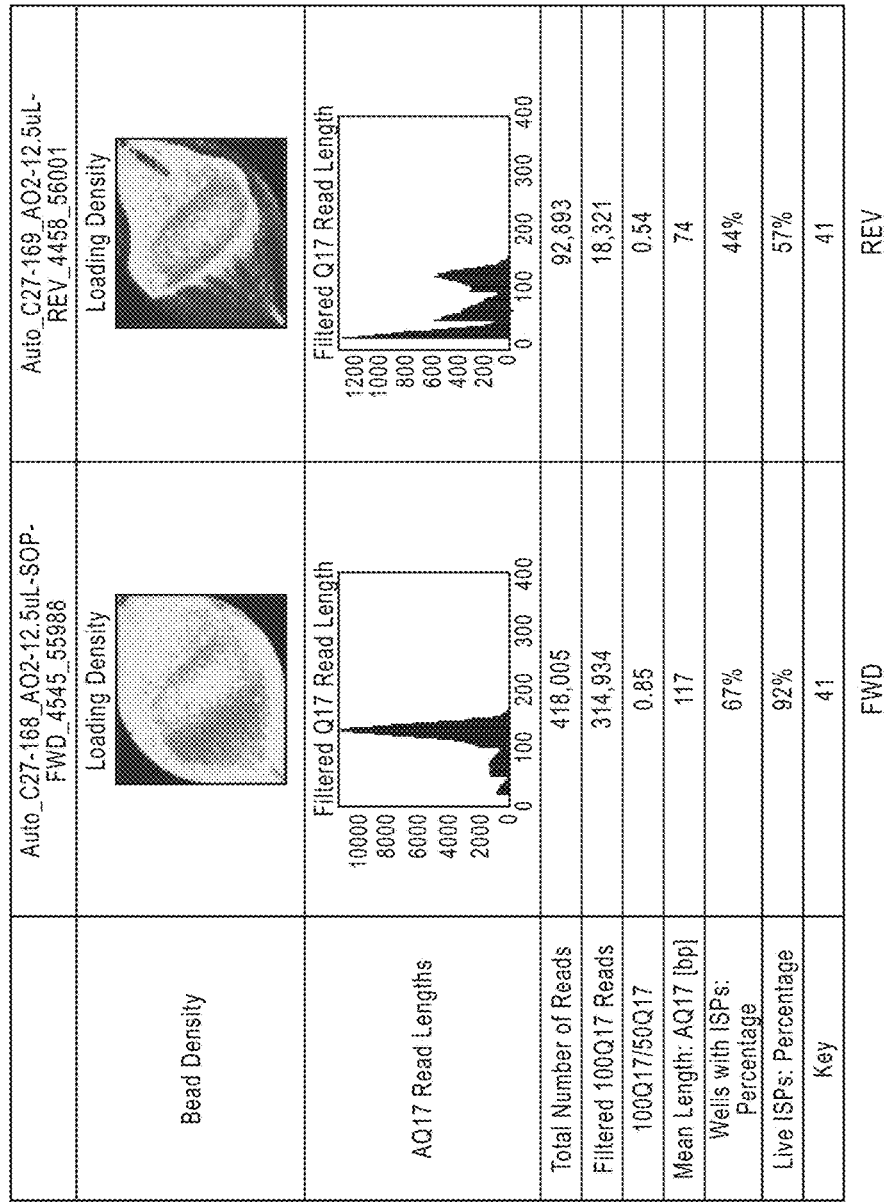

FIG. 19A provides data obtained using an exemplary paired-end sequencing method according to the disclosure.

Figure 19B:
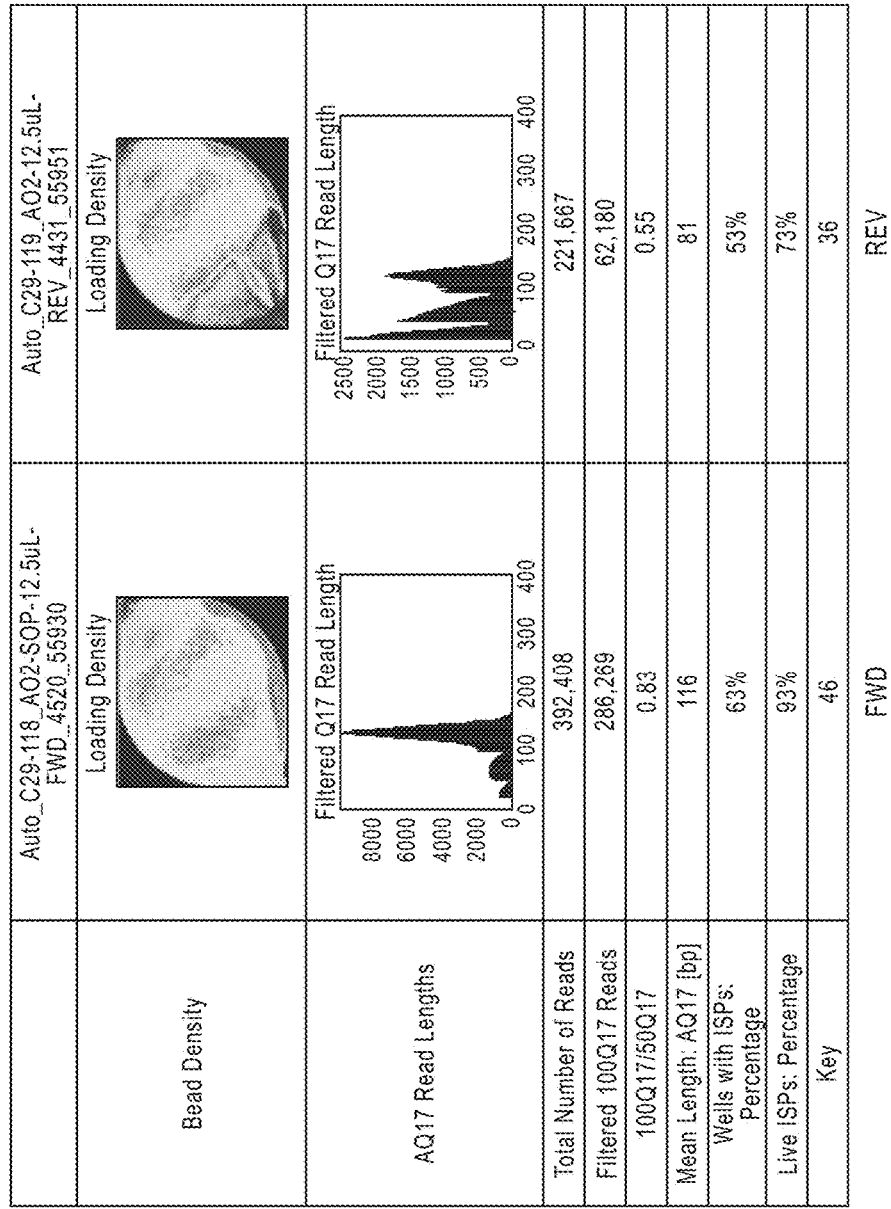

FIG. 19B provides data obtained using an exemplary paired-end sequencing method according to the disclosure.

FIG. 19C provides data obtained using an exemplary paired-end sequencing method according to the disclosure.

Figure 20A:
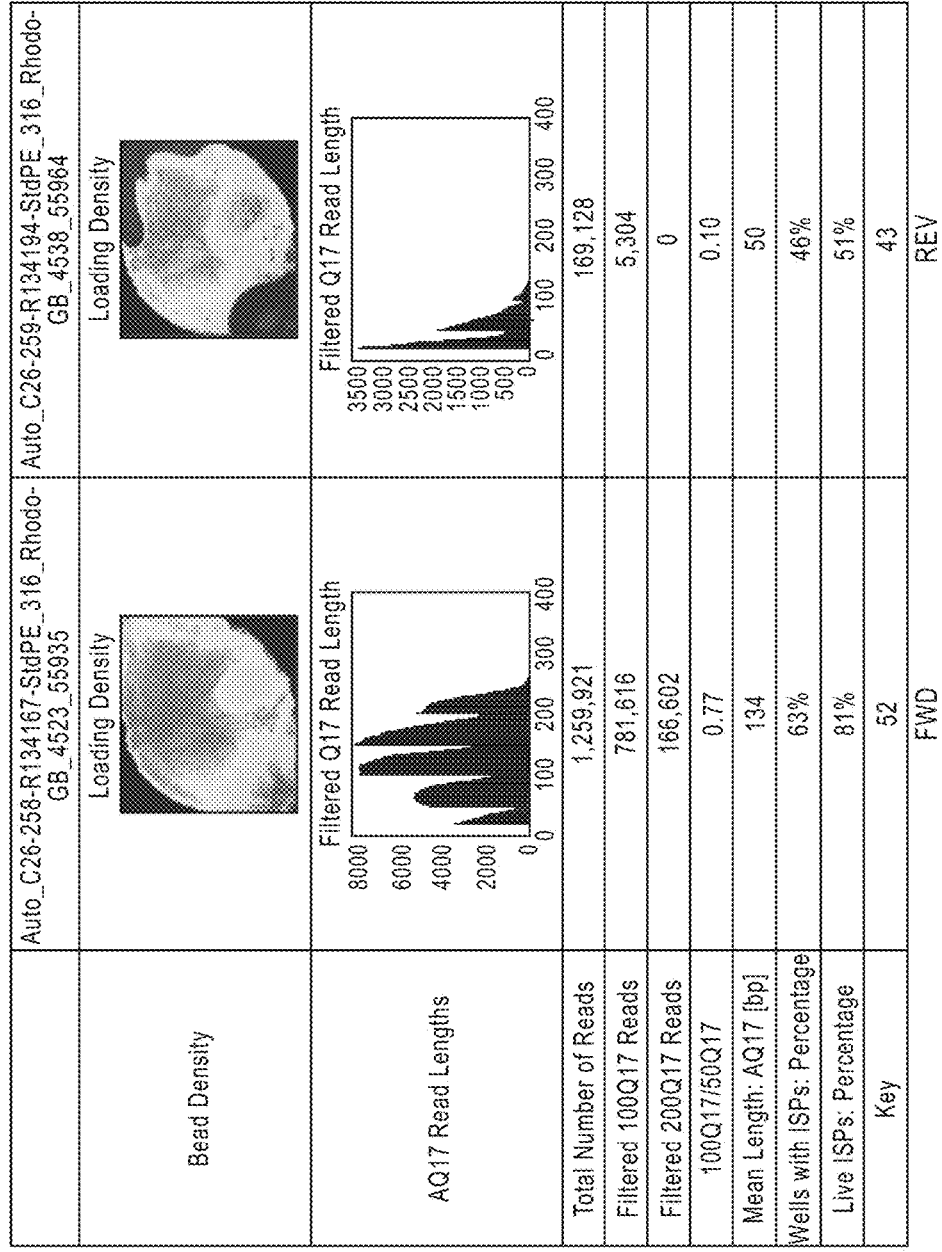

FIG. 20A provides data obtained using an exemplary paired-end sequencing method according to the disclosure.

FIG. 20B provides data obtained using an exemplary paired-end sequencing method according to the disclosure.

FIG. 21A provides data obtained using an exemplary paired-end sequencing method according to the disclosure.

FIG. 21B provides data obtained using an exemplary paired-end sequencing method according to the disclosure.

Figure 22:
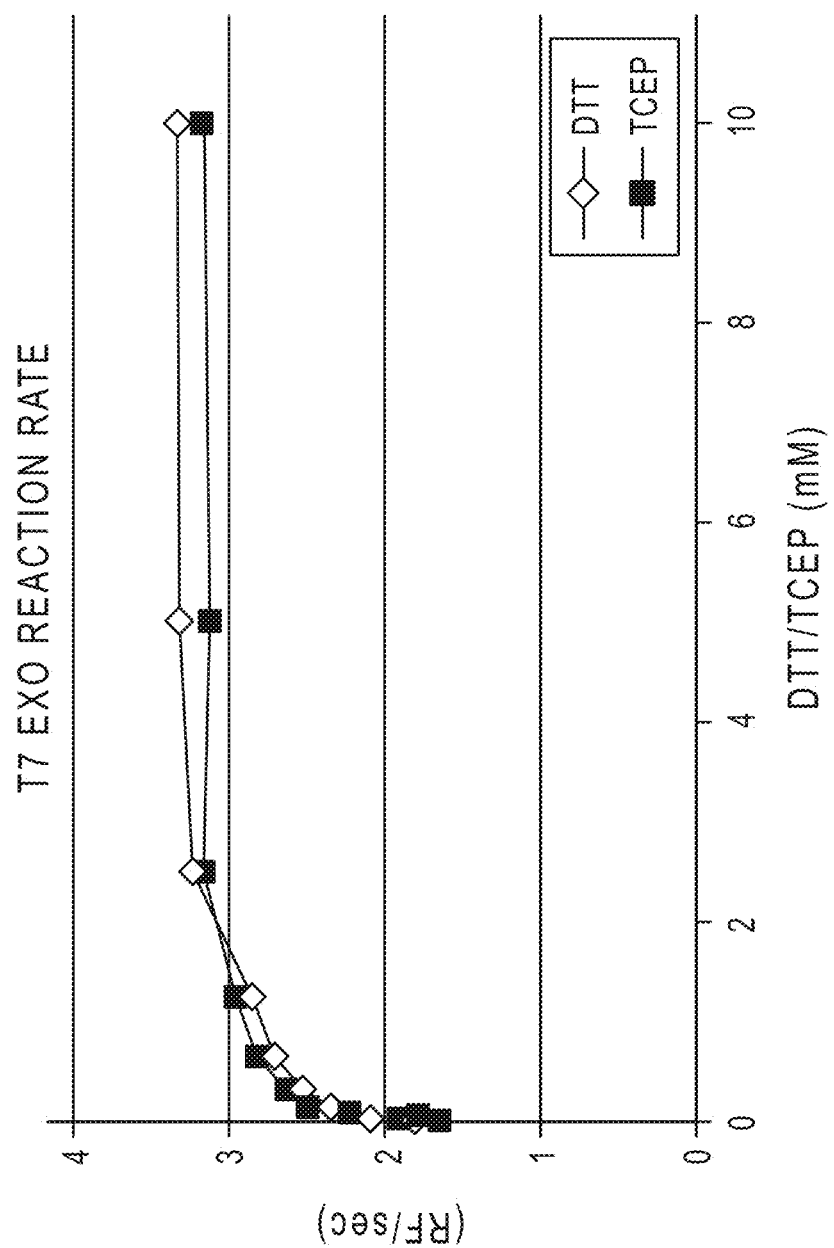

FIG. 22 provides comparative data of two reducing agents for use in exemplary paired end sequencing methods according to the disclosure.

FIG. 23A provides data obtained using an exemplary paired end sequencing method according to the disclosure.

FIG. 23B provides data obtained using an exemplary paired end sequencing method according to the disclosure.

FIG. 23C provides data obtained using an exemplary paired end sequencing method according to the disclosure.

FIG. 23D provides data obtained using an exemplary paired end sequencing method according to the disclosure.

FIG. 23E provides data obtained using an exemplary paired end sequencing method according to the disclosure.

FIG. 23F provides data obtained using an exemplary paired end sequencing method according to the disclosure.

Figure 24:
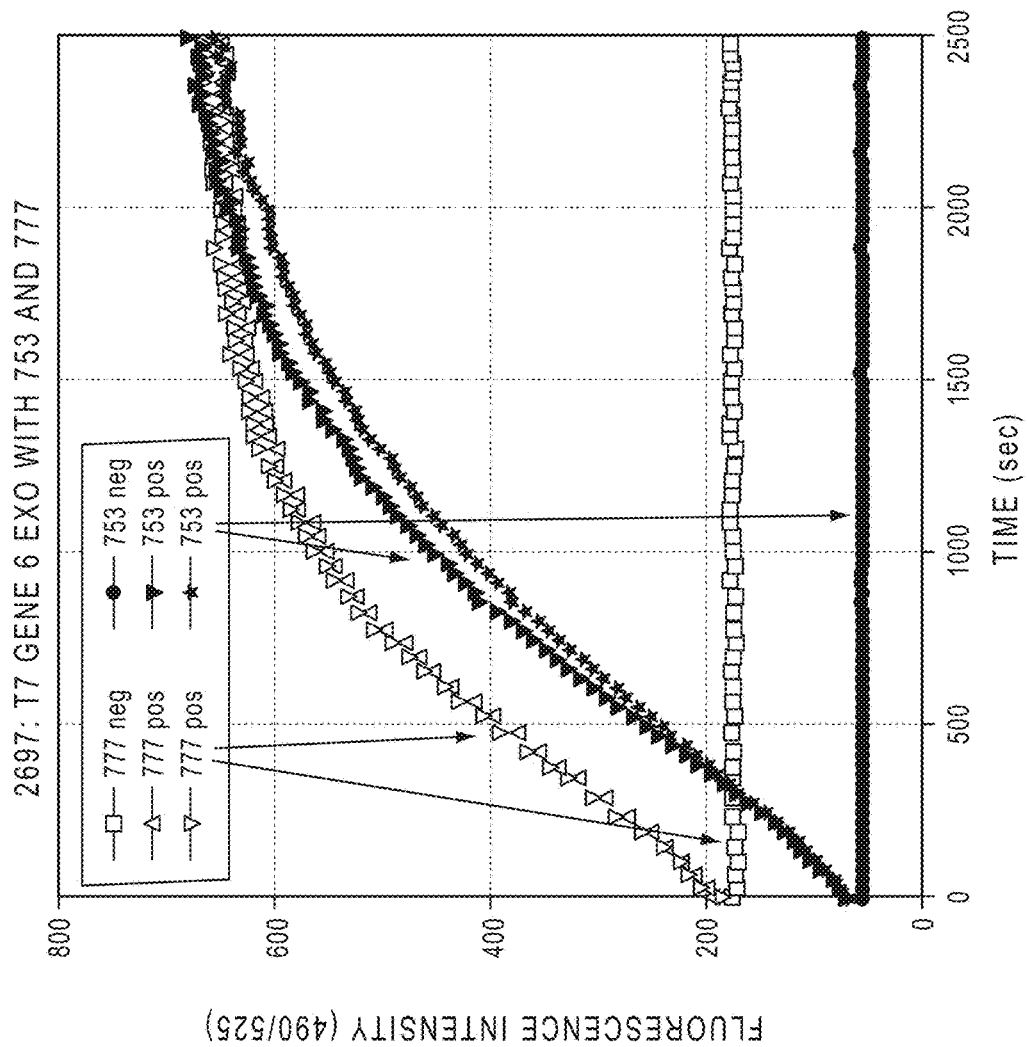

FIG. 24 provides comparative data of oligonucleotide substrates to exonuclease digestion.

Figure 25:
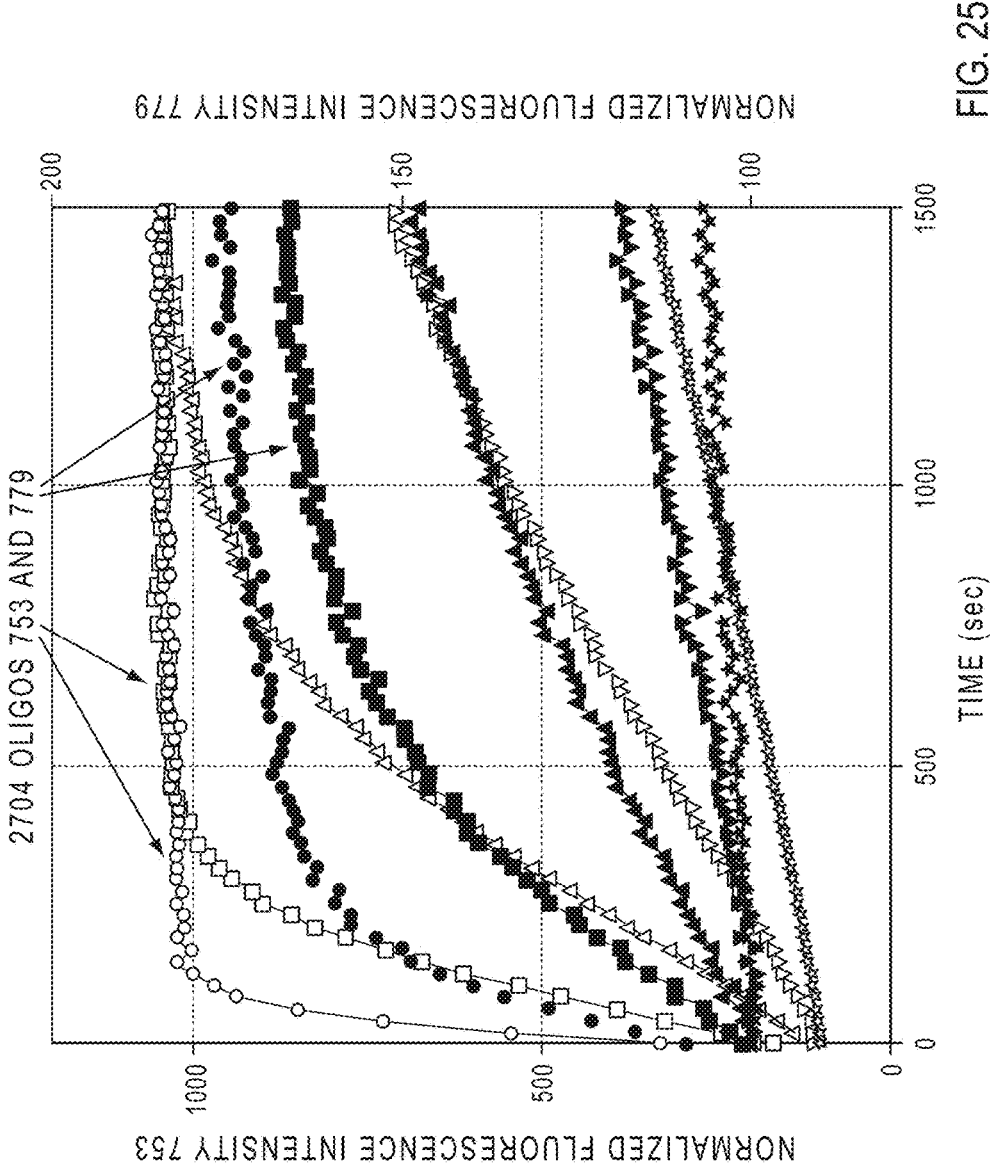

FIG. 25 provides comparative data of oligonucleotide substrates to exonuclease digestion.

Figure 26:
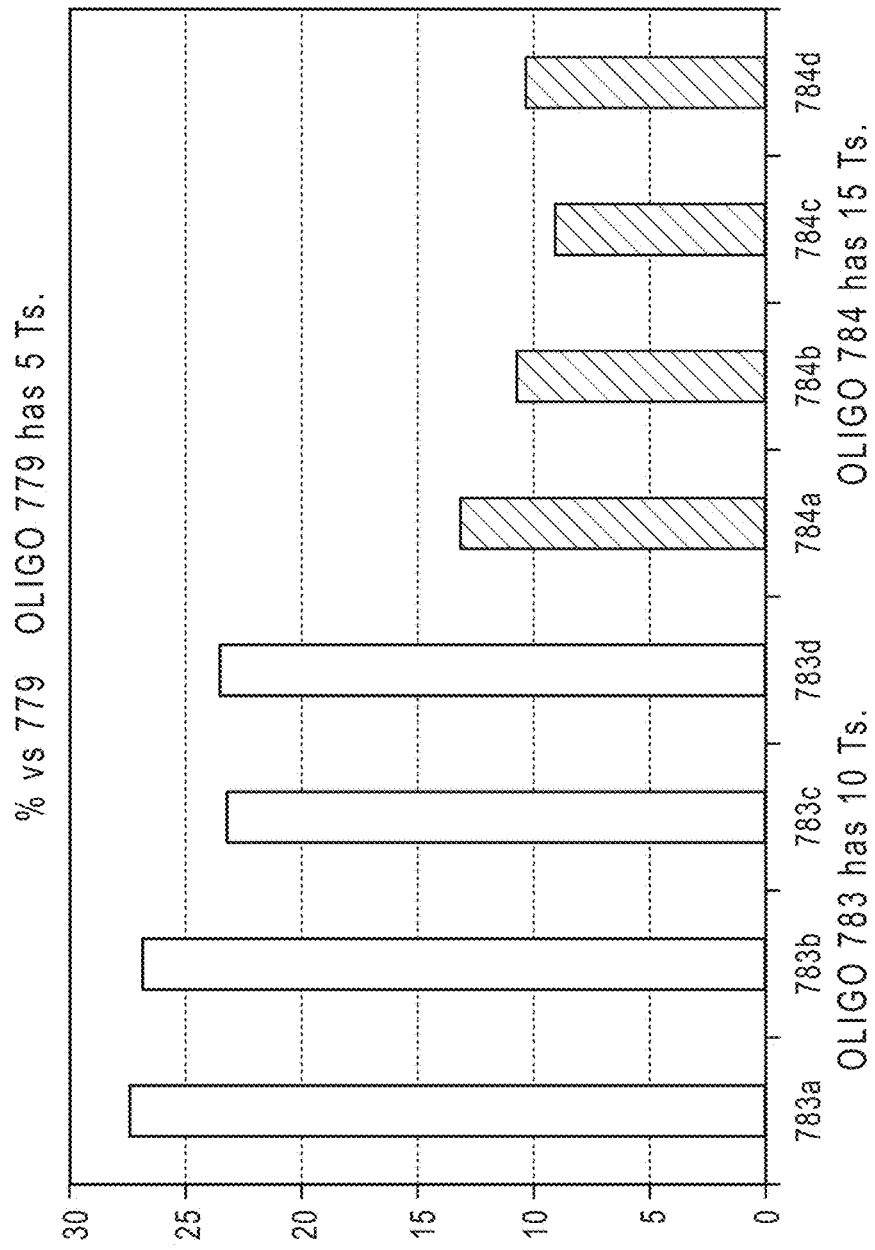

FIG. 26 provides comparative data of oligonucleotide substrates to exonuclease digestion.

Figure 27:
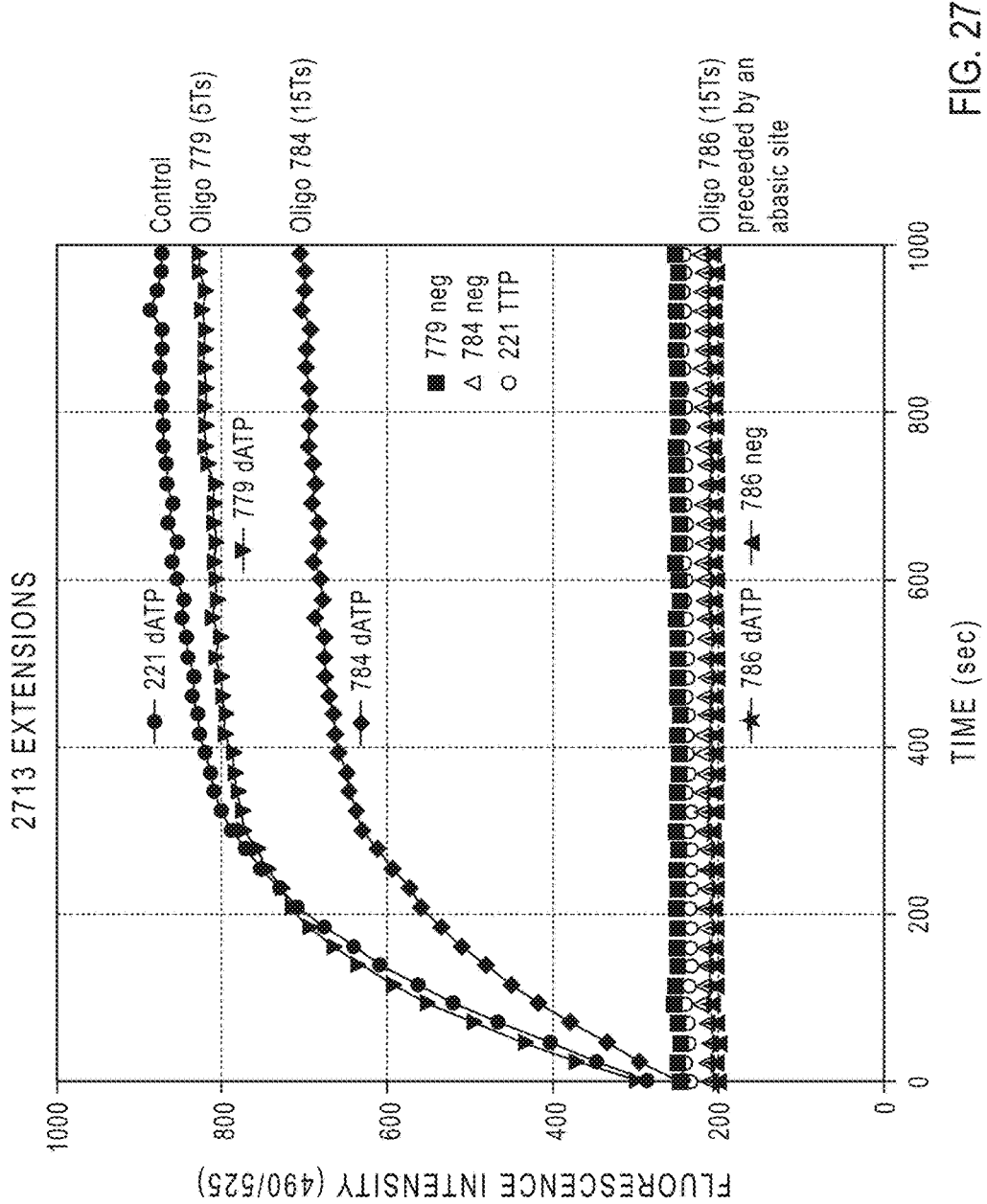

FIG. 27 provides comparative data of oligonucleotide substrates to polymerase extension.

DESCRIPTION

The following description of various exemplary embodiments is exemplary and explanatory only and is not to be construed as limiting or restrictive in any way. Other embodiments, features, objects, and advantages of the present teachings will be apparent from the description and accompanying drawings, and from the claims Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is explicitly or implicitly set forth herein that is contrary to or otherwise inconsistent with any definition set forth in the patents, patent applications, published applications, and other publications that are herein incorporated by reference, the definition and/or description set forth herein prevails over the definition that is incorporated by reference.

As used herein, the terms "comprise", "comprises", "comprising", "contain", "contains", "containing", "have", "having" "include", "includes", and "including" and their variants are not intended to be limiting, are inclusive or open-ended and do not exclude additional, unrecited additives, components, integers, elements or method steps. For example, a process, method, system, composition, kit, or apparatus that comprises a list of features is not necessarily limited only to those features but may include other features not expressly listed or inherent to such process, method, system, composition, kit, or apparatus.

The practice of the present subject matter may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation of synthetic polynucleotides, polymerization techniques, nucleic acid amplification or purification, chemical and physical analysis of polymer particles, nucleic acid sequencing and analysis, chemical and photo-crosslinking of substrates, conjugation chemistry, and the like. Specific illustrations of suitable techniques can be used by reference to the example herein below. Other equivalent conventional procedures can also be used. Such conventional techniques and descriptions can be found in standard laboratory manuals such as *Genome Analysis: A Laboratory Manual Series* (Vols. I-IV), *PCR Primer: A Laboratory Manual, and Molecular Cloning: A Laboratory Manual* (all from Cold Spring Harbor Laboratory Press), Hermanson, Bioconjugate Techniques, Second Edition (Academic Press, 2008); Merkus, Particle Size Measurements (Springer, 2009); Rubinstein and Colby, Polymer Physics (Oxford University Press, 2003); and the like.

The term "complementary" and its variants, as used herein with reference to two or more nucleic acid sequences, refer to any nucleic acid sequences (e.g., portions of target nucleic acid molecules and primers) that can undergo cumulative base pairing at two or more individual corresponding positions in antiparallel orientation, as in a hybridized duplex. Optionally there can be "complete" or "total" complementarity between a first and second nucleic acid sequence where each nucleotide in the first nucleic acid sequence can undergo a stabilizing base pairing interaction with a nucleotide in the corresponding antiparallel position on the second nucleic acid sequence (however, the term "complementary" by itself can include nucleic acid sequences that are not completely complementary over their entire length); "partial" complementarity describes nucleic acid sequences in which at least 20%, but less than 100%, of the residues of one nucleic acid sequence are complementary to residues in the other nucleic acid sequence. In some embodiments, at least 50%, but less than 100%, of the residues of one nucleic acid sequence are complementary to residues in the other nucleic acid sequence. In some embodiments, at least 70%, 80%, 90% or 95%, but less than 100%, of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence. "Noncomplementary" describes nucleic acid sequences in which less than 20% of the residues of one nucleic acid sequence are complementary to residues in the other nucleic acid sequence. A "mismatch" is present at any position in the two opposed nucleotides are not complementary. Complementary nucleotides include nucleotides that are efficiently incorporated by DNA polymerases opposite each other during DNA replication under physiological conditions. In a typical embodiment, complementary nucleotides can form base pairs with each other, such as the A-T/U and G-C base pairs formed through specific Watson-Crick type hydrogen bonding between the nucleobases of nucleotides and/or polynucleotides at positions antiparallel to each other. The complementarity of other artificial base pairs can be based on other types of hydrogen bonding and/or hydrophobicity of bases and/or shape complementarity between bases.

The term "hybridize" and its variants, as used herein with reference to two or more nucleic acid molecules, refer to the process whereby any nucleic acid sequences within the two nucleic acid molecules (e.g., any portions of target nucleic acid molecules and primers) undergo cumulative base pairing at two or more individual corresponding positions in antiparallel orientation, as in a hybridized duplex. Optionally there can be "complete" or "total" hybridization between a first and second nucleic acid molecule where each nucleotide in the first nucleic acid sequence can undergo a stabilizing base pairing interaction with a nucleotide in the corresponding antiparallel position on the second nucleic acid sequence; however, the term "hybridize" by itself can include base pairing between nucleic acid sequences that are not completely complementary over their entire length. "Partial" hybridization describes the process whereby two nucleic acid sequences undergo cumulative base pairing at two or more individual corresponding positions in antiparallel orientation, in which at least 20%, but less than 100%, of the residues of one nucleic acid sequence are complementary to residues in the other nucleic acid sequence. In some embodiments, hybridization includes base pairing between two nucleic acid sequences, where at least 50%, but less than 100%, of the residues of one nucleic acid sequence are base paired with corresponding residues in the other nucleic acid sequence. In some embodiments, at least 70%, 80%, 90% or 95%, but less than 100%, of the residues of one nucleic acid sequence are base paired with corresponding residues in the other nucleic acid sequence. Sequences are said to be "substantially hybridized" when at least 85% of the residues of one nucleic acid sequence participate in cumulative at two or more individual corresponding positions with corresponding residues in the other nucleic acid sequence in antiparallel orientation. In situations where one nucleic acid molecule is substantially longer than the other (or where the two nucleic acid molecule include both substantially complementary and substantially non-complementary regions), the two nucleic acid molecules can be described as "hybridized" even when portions of either or both nucleic acid molecule can remain unhybridized. "Unhybridized" describes nucleic acid sequences in which less than 20% of the residues of one nucleic acid sequence are complementary to residues in the other nucleic acid sequence. In some embodiments, base pairing can occur according to some conventional pairing paradigm, such as the A-T/U and G-C base pairs formed through specific Watson-Crick type hydrogen bonding between the nucleobases of nucleotides and/or polynucleotides positions antiparallel to each other; in other embodiments, base pairing can occur through any other paradigm whereby base pairing proceeds according to established and predictable rules.

As used herein, the term "sequencing" and its variants comprise obtaining sequence information from a nucleic acid strand, typically by determining the identity of at least some nucleotides (including their nucleobase components) within the nucleic acid molecule. While in some embodiments, "sequencing" a given region of a nucleic acid molecule includes identifying each and every nucleotide within the region that is sequenced, in some embodiments "sequencing" comprises methods whereby the identity of only some of the nucleotides in the region is determined, while the identity of some nucleotides remains undetermined or incorrectly determined. Any suitable method of sequencing may be used. In an exemplary embodiment, sequencing can include label-free or ion based sequencing methods. In some embodiments, sequencing can include labeled or dye-containing nucleotide or fluorescent based nucleotide sequencing methods. In some embodiments, sequencing can include cluster-based sequencing or bridge sequencing methods.

As used herein, the phrase "next generation sequencing" refers to sequencing technologies having increased throughput as compared to traditional Sanger- and capillary electrophoresis-based approaches, for example with the ability to generate hundreds of thousands or millions of relatively small sequence reads at a time. Some examples of next generation sequencing techniques include, but are not limited to, sequencing by synthesis, sequencing by ligation, and sequencing by hybridization. Examples of next generations sequencing methods include pyrosequencing as used by 454 Corporation, Illumina's Solexa system, the SOLiD™ (Sequencing by Oligonucleotide Ligation and Detection) system (Life Technologies Inc.), and Ion Torrent Sequencing systems such as the Personal Genome Machine or the Proton Sequencer (Life Technologies Inc).

The term "template nucleic acid", "template polynucleotide", "target nucleic acid" "target polynucleotide", "template strand" and variations refer to a nucleic acid strand that serves as the basis nucleic acid for generating a complementary nucleic acid strand. The sequence of the template nucleic acid can be complementary to the sequence of the complementary strand. The template nucleic acid can be subjected to nucleic acid analysis, including sequencing and composition analysis. The template nucleic acids can be isolated in any form, including chromosomal, genomic, organellar (e.g., mitochondrial, chloroplast or ribosomal), recombinant molecules, cloned, amplified, cDNA, RNA such as precursor mRNA or mRNA, oligonucleotides, whole genomic DNA, obtained from fresh frozen paraffin embedded tissue, needle biopsies, cell free circulating DNA, or any type of nucleic acid library. The target nucleic acid molecules may be isolated from any source including from organisms such as prokaryotes, eukaryotes (e.g., humans, plants and animals), fungus, and viruses; cells; tissues; normal or diseased cells or tissues, body fluids including blood, urine, serum, lymph, tumor, saliva, anal and vaginal secretions, amniotic samples, perspiration, and semen; environmental samples; culture samples; or synthesized nucleic acid molecules prepared using recombinant molecular biology or chemical synthesis methods. The template nucleic acid can be chemically synthesized to include any type of nucleic acid analog.

The term "complementary nucleic acid", "complement polynucleotide", "nucleic acid having a sequence complementary to a template strand", and variations refer to a nucleic acid strand that can be generated using a template nucleic acid as a basis nucleic acid. The complement nucleic acid can have a sequence that is complementary to the sequence of the template strand. The complement nucleic acid can be subjected to nucleic acid analysis, including sequencing and composition analysis.

The terms "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, 100, 150, or 200 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent hybridization conditions.

As used herein, the term "extend", "extending", "extension" and its variants, when used in reference to a nucleic acid molecule, refers to incorporation or attachment of nucleotides to the nucleic acid molecule. Extension of a nucleic acid molecule or a primer can include attachment or incorporation of natural nucleotides and/or nucleotide analogs. Such extension can optionally be performed in a template-dependent fashion. Any suitable method of extending a nucleic acid molecule may be used.

The concept of label-free nucleic acid sequencing, including ion-based nucleic acid sequencing, is described in more detail in the following references: Rothberg et al, U.S. Patent Publication Nos. 2009/0026082, 2009/0127589, 2010/0301398, 2010/0300895, 2010/0300559, 2010/0197507, and 2010/0137143, which are incorporated by reference herein in their entireties. Briefly, in such nucleic acid sequencing applications, nucleotide incorporations are determined by detecting the presence of natural byproducts of polymerase-catalyzed nucleic acid synthesis reactions, including hydrogen ions, polyphosphates, PPi, and Pi (e.g., in the presence of pyrophosphatase).

In a typical embodiment of ion-based nucleic acid sequencing, nucleotide incorporations are detected by detecting the presence and/or concentration of hydrogen ions generated by polymerase-catalyzed nucleic acid synthesis reactions, including for example primer extension reactions. In one embodiment, templates that are operably bound to a primer and a polymerase and that are situated within reaction chambers (such as the microwells disclosed in Rothberg et al, cited above), are subjected to repeated cycles or flows of polymerase-catalyzed nucleotide addition to the primer ("adding step") followed by washing ("washing step"). In some embodiments, such templates may be attached as clonal populations to a solid support, such as a microparticle, bead, or the like, and said clonal populations are loaded into reaction chambers. As used herein, "operably bound" means that a primer is annealed to a template so that the primer can be extended by a polymerase and that a polymerase is bound to such primer-template duplex, or in close proximity thereof so that primer extension takes place whenever nucleotides are supplied.

In each adding step of the cycle, the polymerase extends the primer by incorporating added nucleotide in a template-dependent fashion, such that the nucleotide is incorporated only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. In some embodiments, the production of hydrogen ions is proportional to (e.g., monotonically related) to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, is proportional to the number of contiguous identical complementary bases. If the next base in the template is not complementary to the added nucleotide, then no incorporation occurs and no hydrogen ion is released. In some embodiments, after each step of adding a nucleotide, a washing step is performed, in which an unbuffered wash solution at a predetermined pH is used to remove the nucleotide of the previous step in order to prevent misincorporations in later cycles. In some embodiments, after each step of adding a nucleotide, an additional step may be performed wherein the reaction chambers are treated with a nucleotide-destroying agent, such as apyrase, to eliminate any residual nucleotides remaining in the chamber, thereby minimizing the probability of spurious extensions in subsequent cycles. In some embodiments, the treatment may be included as part of the washing step itself.

In one exemplary embodiment, different kinds (or "types") of nucleotides are added sequentially to the reaction chambers, so that each reaction is exposed to the different nucleotide types one at a time. For example, nucleotide types can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired. In some embodiments, nucleotides can be added to the reaction chamber in a known order. In some embodiments, nucleotides can be added to the reaction chamber in a fixed (repeating cycle) or random order, optionally where the identity of each nucleotide is known prior to addition to the reaction chamber.

Figure 4:
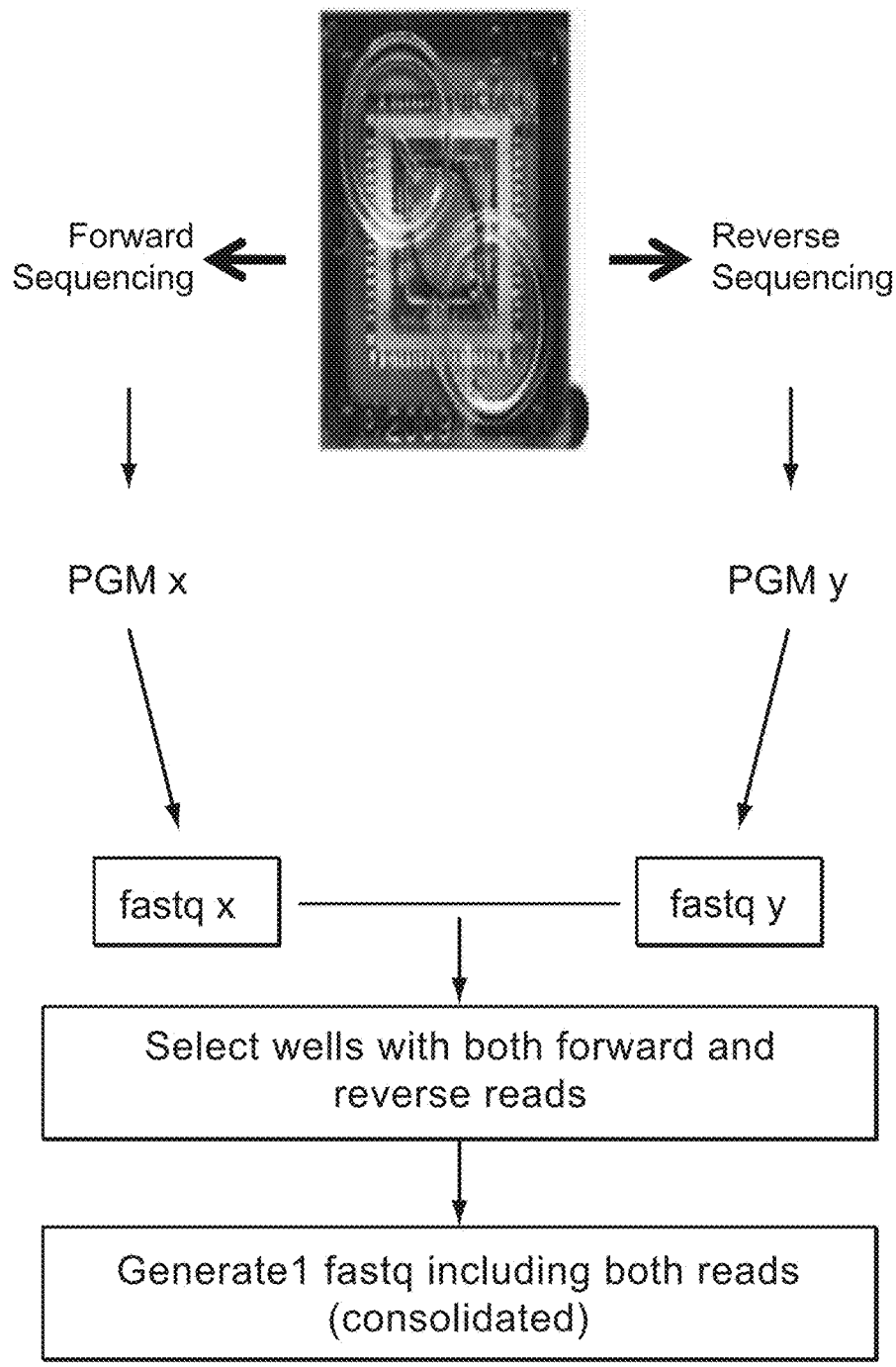
FIG. 4 is a schematic depicting an exemplary embodiment of a paired-end sequencing workflow method according to the disclosure.

In some embodiments, the disclosed methods can be used to provide bi-directional sequencing of a template strand in an ion-based sequencing system, such as the Ion Torrent PGM™ sequencer or Proton Sequencer (Life Technologies, Carlsbad, Calif.). In some embodiments, sequencing accuracy can be improved according to methods, compositions, kits and apparatuses of the disclosure. For example, sequencing data using exemplary paired end sequencing methods according to the disclosure result in increased sequencing accuracy as compared to single end sequencing reactions. While not wishing to be bound or limited by the following, it is proposed that paired end sequencing reactions allow for increased accuracy by consolidating the data obtained from both the forward and reverse reads (FIG. 4). Consolidation of paired end data (i.e., fastq x and fastq y) allows for the identification of nucleotide incorporation which is readily resolved by comparing the nucleotide incorporation data of the forward read with the overlapping reverse read. The issue of sequencing accuracy becomes more prominent as a polymerase moves further away from the sequencing start (or initiation) site. Polymerases are inherently more likely to mis-incorporate a nucleotide or dissociate from the nucleic acid strand to be sequenced as the distance from the start site increases, particularly once the distance reaches one hundred or more nucleotides. Thus, the paired-end sequencing methods, kits, processes and compositions according to the disclosure are well suited for both short (less than 200 base pairs) and long read (i.e., greater than 200 base pairs, 300 base pairs, 400 base pairs, 500 base pairs, and longer) nucleic acid sequencing. In some embodiments, the disclosure generally relates to methods, compositions, kits, systems and apparatuses for improving nucleic acid sequencing accuracy. In some embodiments, the disclosure generally relates to methods, compositions, kits, systems and apparatuses for improving long read nucleic acid sequencing accuracy. For example, in some embodiments the disclosure relates generally to a method for sequencing a template strand in both directions using an ion-based sequencing system, comprising contacting a template strand with a first primer that is attached to a support (also referred to herein as a "support-linked first primer"). The first support-linked primer can include a sequence that is substantially complementary to a corresponding sequence in the nucleic acid template. The contacting can be performed under hybridizing conditions, such that the template strand hybridizes to the support-linked first primer. Typically, the first primer is linked to the support at or near the 5' end, while the 3' end of the support-linked first primer remains available for hybridization and/or template-dependent extension by a polymerase. The support-linked first primer optionally hybridizes to the nucleic acid template at or near the 3' end of the template. The method can further include extending the support-linked first primer in a template-dependent fashion, thereby forming an extended first primer product (EFPP), which is also linked to the support. The extended first primer product typically includes a sequence that is substantially complementary to a sequence of the template strand, and the extended first primer product can be hybridized to the template strand to form a first nucleic acid duplex.

The method can further include removing the template via melting or degradation. In some embodiments, the first primer (and as a result, the extended first primer product) is linked to the support, such that melting or degradation of the duplex formed by the template and the extended first primer product allows removal and separation of the template strand, generating an extended first primer product that is linked to the support.

In some embodiments, the support-linked first primer includes a nicking site that can be recognized and nicked by a nicking agent. Following extension of the first primer, the nicking site will be included in the resulting extended first primer product.

In some embodiments, the method further includes contacting the support-linked extended first primer product with a second primer under hybridizing conditions so that the second primer can hybridize to the extended first primer product. The second primer optionally hybridizes to the extended first primer product at or near the 3' end of the extended first primer product. In some embodiments, the method further includes extending the second primer using a polymerase, thereby forming an extended second primer product (ESPP). In a typical embodiment, the second primer is extended towards the support, thereby generating an ESPP whose 3' end points towards the surface of the support.

Optionally, extending the second primer can include sequencing by synthesis. For example, the extending can include detecting incorporation of each (or some) of the nucleotides during the extension, and/or determining the identity of each (or some) of the nucleotides during the extension. In a typical embodiment, the nucleic acid duplex is bound to the support within a microwell of an ion-based sequencing system (e.g., Ion Torrent PGM™ system), where the well is operationally associated with a FET capable of sensing the presence of nucleotide incorporation byproducts. The four different nucleotide types (A, C, G and T) are each contacted serially with the second primer under nucleotide polymerization conditions; only nucleotides that are complementary to the next base in the extended first primer product (EFPP) will be incorporated into the second primer by the polymerase, and such nucleotide incorporation is detecting by detecting the presence of nucleotide incorporation byproducts (e.g., hydrogen ions) using the FET to obtain a first sequencing read.

In some embodiments, the EFPP includes a nicking site that can be recognized and nicked by a nicking agent. For example, the nicking site can be present in the first primer itself, such that following extension of the first primer, the nicking site will be included in the resulting extended first primer product. Typically, the second primer is extended past the nicking site within the EFPP, so that the ESPP will include sequence that is complementary to the nicking site in the EFPP.

The method can further include nicking the extended first primer product at the nicking site using a suitable nicking agent. In some embodiments, the nicking agent can include one or more nickases. In some embodiments, the nicking agent can include one or more site-specific nickases or restriction enzymes. In some embodiments, the nicking agent can specifically nick the template strand while leaving the extended first primer product or complementary strand unaffected.

The method can further include degrading the EFPP using a suitable degrading agent. In a typical embodiment, the degrading includes contacting a nucleic acid duplex including the nicked EFPP hybridized to the ESPP with a 5' to 3' exonuclease, and degrading a portion of the EFPP from the 5' end of the nick via 5' to 3' exonuclease digestion, while leaving a portion ("residual portion") of the EFPP substantially intact or undegraded. This residual portion typically includes the 3' end of the nick plus associated "upstream" sequence that is linked at or near the primer, and remains hybridized to a portion of an ESPP. Such digestion can render a portion of the ESPP single-stranded. A portion of the ESPP can remain hybridized to the residual portion of the EFPP.

In embodiments where the extending includes ion-based sequencing by synthesis, the nicking agent and/or the degrading agent can be added directly to the ion based sequencing system. For example, in some embodiments, nicking enzymes and degrading agents can be added directly to the Ion chip within a PGM™ sequencer. Alternatively, the Ion Chip can be placed in a Paired-End module configured to allow such reagent exchange during the sequencing.

In a typical embodiment, the degrading does not affect the ESPP because the ESPP is modified or treated so that it is resistant to the degrading. For example, in some embodiments the second primer used to synthesize the ESPP can be resistant to digestion by the degrading agent, so that the ESPP is not digested by the degrading agent.

In some embodiments, the method can further include extending the residual portion of the EFPP after the degrading. The residual portion of the EFPP remains hybridized to the ESPP and therefore can be extended in a template-dependent manner. In some embodiments, extending the residual portion of the EFPP can include sequencing by synthesis, thereby obtaining a second sequencing read in the opposite direction from the first. Typically, the extending can include the use of one or more polymerases such as, but not limited to Klenow, DNA polymerase I, and T4 DNA polymerase. For example, the extending can be performed in a microwell of an ion-based sequencing system (e.g., Ion Torrent PGM™ sequencer and Proton™ sequencer) and include detecting incorporation of each (or some) of the nucleotides during the extension, and/or determining the identity of each (or some) of the nucleotides during the extension using the PGM™ or Proton™ sequencer. In some embodiments, a removal or wash step is carried out prior to extension of the residual portion of the EFPP but after extension of the extended first primer product.

In some embodiments, the template strand is directly linked to the support or surface, such that there is no need for hybridization to a support-linked primer in order to link the template (or its complement) to the support or surface. In such embodiments, the process can be simplified to include only two separate primer extension steps, rather than the three steps described above.

In some embodiments, any one or more of the nucleic acid molecules referred to herein (including without limitation the first primer, the second primer, the template strand, the first primer extension product and the second primer extension product) can be linked, or can be modified to support linkage, to a surface or solid support. For example, in some embodiments the nucleic acid molecule can be linked to one member of a binding pair, while the surface or support can be linked to the other member of the binding pair. As used herein, the term "binding pair" and its variants refers to two molecules, or portions thereof, which have a specific binding affinity for one another and typically will bind to each other in preference to binding to other molecules. Typically but not necessarily some or all of the structure of one member of a specific binding pair is complementary to some or all of the structure possessed by the other member, with the two members being able to bind together specifically by way of a bond between the complementary structures, optionally by virtue of multiple noncovalent attractions. The two members of a binding pair are referred to herein as the "first member" and the "second member" respectively.

The following may be mentioned as non-limiting examples of molecules that can function as a member of a specific binding pair, without this being understood as any restriction: thyroxin-binding globulin, steroid-binding proteins, antibodies, antigens, haptens, enzymes, lectins, nucleic acids, repressors, oligonucleotides, polynucleotides, protein A, protein G, avidin, streptavidin, biotin, complement component C1q, nucleic acid-binding proteins, receptors, carbohydrates, complementary nucleic acid sequences, and the like. Examples of specific binding pairs include without limitation: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; and an oligonucleotide or polynucleotide and its corresponding complement.

As used herein, the term "biotin moiety" and its variants comprises biotin (cis-hexahydro-2-oxo-1H-thieno[3,4]imidazole-4-pentanoic acid) and any derivatives and analogs thereof, including biotin-like compounds. Such compounds include, for example, biotin-e-N-lysine, biocytin hydrazide, amino or sulfhydryl derivatives of 2-iminobiotin and biotinyl-∈-aminocaproic acid-N-hydroxysuccinimide ester, sulfosuccinimideiminobiotin, biotinbromoacetylhydrazide, p-diazobenzoyl biocytin, 3-(N-maleimidopropionyl)biocytin, and the like. "Biotin moiety" also comprises biotin variants that can specifically bind to an avidin moiety.

The term "biotinylated" and its variants, as used herein, refer to any covalent or non-covalent adduct of biotin with other moieties such as biomolecules, e.g., proteins, nucleic acids (including DNA, RNA, DNA/RNA chimeric molecules, nucleic acid analogs and peptide nucleic acids), proteins (including enzymes, peptides and antibodies), carbohydrates, lipids, etc.

The terms "avidin" and "avidin moiety" and their variants, as used herein, comprises the native egg-white glycoprotein avidin, as well as any derivatives, analogs and other non-native forms of avidin, that can specifically bind to biotin moieties. In some embodiments, the avidin moiety can comprise deglycosylated forms of avidin, bacterial streptavidins produced by selected strains of *Streptomyces*, e.g., *Streptomyces avidinii*, to truncated streptavidins, and to recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin®, Captavidin®, Neutravidin® and Neutralite Avidin®. All forms of avidin-type molecules, including both native and recombinant avidin and streptavidin as well as derivatized molecules, e.g. nonglycosylated avidins, N-acyl avidins and truncated streptavidins, are encompassed within the terms "avidin" and "avidin moiety". Typically, but not necessarily, avidin exists as a tetrameric protein, wherein each of the four tetramers is capable of binding at least one biotin moiety.

As used herein, the term "biotin-avidin bond" and its variants refer to a specific linkage formed between a biotin moiety and an avidin moiety. Typically, a biotin moiety can bind with high affinity to an avidin moiety, with a dissociation constant ($K_d$) typically in the order of $10^{-14}$ to $10^{-15}$ mol/L. Typically, such binding occurs via non-covalent interactions.

For example, a nucleic acid molecule can be amino-modified for attachment to a surface or support (e.g., a microparticle or a planar surface). In some embodiments, an amino-modified nucleic acid molecule can be attached to a surface that is coated with a carboxylic acid. In some embodiments, an amino-modified nucleic acid can be reacted with EDC (or EDAC) for attachment to a carboxylic acid coated surface (with or without NHS).

In some embodiments, a nucleic acid molecule can be modified to attach to one member of a binding pair (e.g., biotin), and thus bind to a surface or support including a second member of the binding pair. In some embodiments, a biotinylated nucleic acid molecule can be attached to another member of a binding pair (e.g., avidin-like, such as streptavidin) which is attached to a surface or support. In some embodiments, the template strand can be linked to a solid support. In some embodiments, the support can be an array, sphere, particle, microparticle, filter, gel or bead. In some embodiments, the particle can be an Ion Sphere™ Particle (Life Technologies, CA). In some embodiments, the support can be a planar surface such as a slide, groove or channel. In some embodiments, the support can be concave, convex, or any combination thereof, such as an array surface or plurality of flowcells. In some embodiments, the support can be a reaction chamber or microwell. In some embodiments, the support can include a surface with a texture such as an etching or passivation layer. In some embodiments, a support can be made from materials such as glass, borosilicate glass, silica, quartz, fused quartz, mica, polyacrylamide, plastic polystyrene, polycarbonate, polymethacrylate (PMA), polymethyl methacrylate (PMMA), polydimethylsiloxane (PDMS), silicon, germanium, graphite, ceramics, silicon, semiconductor fabrics, high refractive index dielectrics, crystals, gels, polymers, or films (e.g., films of gold, silver, aluminum, or diamond). In some embodiments, template nucleic acids linked to a support, optionally linked through one or more primers, can be arranged in a random or ordered array on the support.

In some embodiments, the support can be modified to enhance attachment of a nucleic acid molecule to the support and/or enhance sequencing throughput from a nucleic acid molecule attached or operably bound to the support. For example, the support can be modified to include a plurality of primers attached to its surface that are operably bound to at least some portion of a template nucleic acid molecule to be sequenced (e.g., FIG. 2, Primer B). In some embodiments, the support can be modified to include a plurality of primers partially-embedded within the support that are operably bound to at least some portion of a template nucleic acid molecule to be sequenced. In some embodiments, the support can be modified to include a plurality of primers anchored to the outer surface of the support and operably bound to at least some portion of a template nucleic acid molecule to be sequenced (e.g., FIG. 3, Primer B). In some embodiments, the support can include a particle which can optionally include a porous, permeable or scaffolded particle.

In some embodiments, a plurality of primers can be attached or immobilized to a support at their 5' end. In some embodiments, the 5' end of one or more of the plurality of primers attached or immobilized to the support can be modified to enhance sequencing throughput and/or accuracy. For example, the 5' end of one or more primers immobilized on a support can be modified to enhance resistance to enzymatic degradation. In some embodiments, the 5' end of one or more primers immobilized on a support can have enhanced resistance to exonuclease activity. For example, the 5' end of one or more primers immobilized on a support can have enhanced resistance to exonuclease activity as compared to the 5' end of a comparable non-modified immobilized primer. In some embodiments, the 5' end of one or more primers immobilized on a support can be modified to protect the 5' end of the primer from deterioration which can lead to template loss or reduction of sequencing throughput when conducting "reverse" reads. In some embodiments, the 5' end of one or more primers immobilized on a support can be modified to include one or more phosphorothioates. For example, a primer immobilized on a support can include one, two, three, four, five, six, seven or more phosphorothioates. In some embodiments, the 5' end of one or more primers immobilized on a support can be modified to include a polyethylene glycol (PEG) linker. In some embodiments, the 5' end of one or more primers immobilized on a support can be modified to include a single stranded region of about 5 nucleotides to about 15 nucleotides. In some embodiments, the 5' end of one or more primers immobilized on a support can be modified to include a hairpin structure. In some embodiments, the 5' end of one or more primers immobilized on a support can be modified to include an abasic site. In some embodiments, the 5' end of one or more primers immobilized on a support can be modified to include one or more locked nucleic acids. The phrase "locked nucleic acid" (LNA) as used herein refers to a modified RNA nucleotide in which the ribose is modified with an extra bridge connecting the 2' oxygen and 4' carbon. A locked nucleic acid can be resistant to cleavage by Exonuclease III. In some embodiments, the 5' end of one or more primers immobilized on a support can be modified to include one or more 2'-OMe RNA residues. 2'-OMe RNA residues possess a methyl group at the 2'-OH residue of the ribose molecule that protects against nuclease degradation.

In some embodiments, the 5' end of one or more primers immobilized on a support can include one or more of a single stranded region of about 5 nucleotides to about 15 nucleotides, a phosphorothioate, a PEG linker, a hairpin structure, an abasic site, a 2'-OMe residue or a combination thereof.

In some embodiments, a template strand can be directly attached to a support. In some embodiments, one or more primers (e.g., FIG. 2, Primer B) can attach or link the template strand or the extended primer product to the support. In some embodiments, a primer attached to the support can be linked to the template strand by a ligase. In some embodiments, one or more primers attached to the support can contain a modification such as a photolabile group that allows attachment of the template strand or the extended primer product to the support. In some embodiments, an extended primer product can be photo-crosslinked to the support, while the template strand is degraded, thereby generating a single-stranded extended primer product attached to the support. In some embodiments, a primer attached to the support can include an aminated residue.

In some embodiments, the disclosure relates generally to methods, compositions, systems, apparatuses and kits for obtaining sequence information from a nucleic acid molecule. Optionally, such sequence information can be obtained in one or both directions (e.g., a "forward" and/or "reverse" direction) from a nucleic acid strand. In some embodiments, sequence information can be obtained in a first orientation, optionally followed by obtaining sequencing information in a second orientation that is reversed relative to the first orientation. In some embodiments, sequence information can be obtained in one or both directions from a template strand. In some embodiments, such sequencing can be referred to as "bi-directional" sequencing. Bi-directional sequencing can optionally include sequencing at least some portion of each strand of a nucleic acid duplex. In some embodiments, sequence information can be first obtained as a "forward" read which can include sequencing from the distal end of a support bound template nucleic acid molecule. In some embodiments, a second or serial sequencing reactions can be performed to obtain a "reverse" read of the initial support bound nucleic acid molecule, which can optionally include sequencing from the proximal end. In some embodiments, bi-directional sequencing can be performed as a distal sequencing reaction followed by a proximal sequencing reaction. In some embodiments, one or more of the "forward" or "reverse" sequencing reactions can be repeated one or more times to improve sequencing throughput and/or accuracy. For example, in some embodiments a "forward" read can be repeated by degrading or separating an extended primer product from the template nucleic acid molecule and re-applying and hybridizing a first primer to the template nucleic acid molecule, followed by primer extension. In some embodiments, the separating can include a denaturing treatment such as, but not limited to, an enzymatic, thermal or chemical degradation. In some embodiments, the extended primer product can be separated from the template nucleic acid molecule by treatment with sodium hydroxide. In some embodiments, the extended primer product can be separated from the template nucleic acid molecule by heat. In some embodiments, the "forward" read can be repeated as desired, by re-applying and hybridizing a sequencing primer to the nucleic acid molecule to be sequenced. The re-applied sequencing primer can be extended, for example under polymerization conditions in the presence of a polymerase and dNTPs.

In some embodiments a "reverse" read can be repeated by degrading or separating the template nucleic acid molecule (that is substantially complementary to the extended first primer product) to produce one or more single-stranded regions within the extended first primer product. In some embodiments, the separating can include an enzymatic, thermal or chemical treatment. In some embodiments, the degrading can include one or more enzymes that remove, digests, or nicks one or more nucleotides incorporated into the nucleic acid molecule that is substantially complementary to the extended first primer product. In some embodiments, the one or more degrading enzymes can include a nicking enzyme, optionally in combination with an exonuclease. In some embodiments, the degrading can further include an endonuclease. In some embodiments, bi-directional sequencing of a template nucleic acid molecule can optionally be performed as a first proximal sequencing reaction coupled with a second distal sequencing reaction. In some embodiments, bi-directional sequencing of a template nucleic acid molecule can optionally be performed as a first distal sequencing reaction coupled with a second proximal sequencing reaction.

In some embodiments, the disclosure relates generally to obtaining sequence information from a nucleic acid strand, comprising: hybridizing an existing nucleic acid molecule (frequently referred to as a "primer") to the nucleic acid strand to be sequenced (frequently referred to as the "template"), and extending the primer via template-dependent nucleotide incorporation using a polymerase. In some embodiments, the primer can be extending under polymerization conditions using natural or analog nucleotides, including nucleotides having a label or fluorescent proprieties. In some embodiments, the primer can be extended under polymerization conditions using nucleotides that are label-free. In some embodiments, sequencing information can be obtained by sequencing at least some portion of the extended first primer product. In some embodiments, sequencing information can be obtained for substantially all of the extended first primer product.

In some embodiments, a first primer (also frequently referred to as a "forward" primer) is hybridized to the template strand and extended, thereby obtaining sequence information in the "forward" direction (frequently referred to as a "forward" read) and generating an extended first primer molecule (frequently referred to herein as the "complement" or "extended first primer product") that is substantially complementary to the template strand over at least some portion of their respective lengths. In some embodiments, the phrase "substantially complementary to the template strand" when used in reference to an extended primer product refers to a situation where at least 85% of the residues of the extended primer product are complementary to the template strand. In some embodiments, the forward primer can be fully extended (to generate a fully extended primer product) when hybridized to a nucleic acid molecule in the presence of a polymerase and dNTPs. In some embodiments, some or all of the nucleotides incorporated into the extended first primer product are sequenced to provide sequence information.

It is well known in the art that extension of a nucleic acid molecule generally includes contacting the nucleic acid molecule with a polymerase and nucleotides, under nucleotide incorporation conditions. Generally, a polymerase is bound to, or is in close proximity to, the nucleic acid molecule to facilitate attachment or incorporation of nucleotides to the nucleic acid molecule. Typically, a polymerase extends the nucleic acid molecule by incorporating a nucleotide if the next base in the nucleic acid molecule is the complement of the added nucleotide. If there is one complementary base, there is one incorporation, if two, there are two incorporations, if three, there are three incorporations, and so on. In an exemplary embodiment, the polymerase includes any enzyme, or fragment or subunit thereof, which can catalyze incorporation of nucleotides and/or nucleotide analogs. In some embodiments, extension reactions can be conducted using a DNA or RNA polymerase enzyme. In some embodiments, the DNA polymerase can be a thermostable polymerase. In some embodiments, a polymerase can include a high fidelity polymerase. In an exemplary embodiment, a polymerase can be a naturally-occurring polymerase, recombinant polymerase, mutant polymerase, variant polymerase, fusion or otherwise engineered polymerase, chemically modified polymerase, synthetic molecules, or analog, derivative or fragment thereof. In some embodiments, a thermostable polymerase includes a recombinant polymerase, mutant polymerase, variant polymerase, fusion or otherwise engineered polymerase, chemically modified polymerase, derivative or fragment of one or more of the following thermostable polymerases: Taq polymerase (from *Thermus aquaticus*), Tfi polymerase (from *Thermus filiformis*), Pfu polymerase (from *Pyrococcus furiosus*), Tth (from *Therms thermophilus*), Pow polymerase (from *Pyrococcus woesei*), Tli polymerase (from *Thermococcus litoralis*), Pol I and II polymerases (from *Pyrococcus abyssi*), Pab (from *Pyrococcus abyssi*), Bst polymerase (from *Bacillus stearothermophilus*), Tli polymerase, 9° N polymerase, and phi29 polymerase.

Typical conditions for nucleic acid extension can include reactions conditions of about 25° C.-80° C. In some embodiments, extension can include modulating the extension conditions. Modulating can optionally include: increasing or decreasing the enzyme concentration; increasing or decreasing the nucleotide concentration; increasing or decreasing a cation concentration; increasing or decreasing a reaction temperature, reaction time and/or pH, and the like. The modulating can include increasing or decreasing the rate of the reaction, increasing or decreasing the yield of product of the reaction, and the like. In some embodiments, extension reactions can optionally include a sequencing reaction thereby obtaining sequence information from a nucleic acid strand, typically by determining the identity of at least some nucleotides within the nucleic acid molecule being extended.

In some embodiments, extension can be performed in the presence of appropriate buffers and/or nucleotides (including nucleotide analogs or biotinylated nucleotides). In some embodiments, an appropriate buffer can optionally include a detergent and/or an additive. For example, an appropriate buffer can optionally include one or more detergents such as, but not limited to, Tween, SDS, Triton, and the like. In some embodiments, an additive can include a polymer compound comprising a homo-polymeric and hetero-polymeric compound. In some embodiments, a polymer compound comprises a chain of two or more tetrahydrapyrrole monomers. In some embodiments, a tetrahydrapyrrole monomer comprises a five-membered heterocyclic ring. In some embodiments, in a chain of tetrahydropyrrole rings, one or more tetrahydropyrrole rings comprise a nitrogen atom reacted with a carbonyl or carboxylic acid compound. In some embodiments, a polymer compound comprises polyvinylpyrrolidone (e.g., povidone or crospovidone), poly(4-vinylphenol), and vinylpyrrolidone/vinyl acetate copolymer (e.g., copovidone). In some embodiments, a polymer compound comprises two or more monomers of N-vinyl-pyrrolidone, including modified polymers thereof. Modified polymers of poly(N-vinyl-pyrrolidone) comprise monofunctionalized (e.g., hydroxyl or carboxy end group), side-chain conjugates (e.g., poly- and multifunctional side chains), and grafted copolymers. In some embodiments, polyvinylpyrrolidone includes various molecular weight polymers including average molecular weights of about 5 kD-55 kD, for example 10 kD, 29 kD, 40 kD, and 55 kD molecular weight compounds. In some embodiments, an additive such as polyvinylpyrrolidone (PVP) can be present in an appropriate buffer at about 0.1-8%, or about 1-2%, or about 2-3%, or about 3-4%, or about 4-5%, or about 5-6%, or about 6-7%, or about 8-10%.

In some embodiments, an appropriate buffer can include one or more reducing agents such as, but not limited to, dithiothreitol (DTT), tris(2-carboxyethyl)phosphine (TCEP), and the like. In some embodiments, a reducing agent such as DTT or TCEP can be present in an appropriate buffer at about 0.1-8%, or about 1-2%, or about 2-3%, or about 3-4%, or about 4-5%, or about 5-6%, or about 6-7%, or about 8-10%.

In some embodiments, the methods, kits, compositions and apparatuses of the disclosure further include sequencing the extended first primer product. Such sequencing can optionally include hybridizing a second primer to the extended first primer product and extending the second primer via template-dependent nucleotide incorporation using a polymerase, thereby obtaining sequence information in the "reverse" direction (frequently referred to as a "reverse" read of the template) and generating an extended second primer molecule (frequently referred to herein as the "template copy" or "extended second primer product") that is substantially identical to the template strand over at least some portion of their respective lengths. In some embodiments, sequencing information of the reverse read can be obtained by sequencing at least some portion of the extended second primer product. In some embodiments, sequencing information of the reverse read can be obtained for substantially all of the extended second primer product.

In some embodiments, the methods of the disclosure further include introducing at least one nick or gap into one or more nucleic acid molecules selected from the group consisting of: the first primer, the second primer, the template strand, the first extended primer product and the second extended primer product. As used herein, the term "nick" and its variants refers to any discontinuity in a nucleic acid strand where there is no phosphodiester bond between any two adjacent nucleotides of the strand.

The nick can include one free 3' end and one free 5' end. In some embodiments, the nicking includes introducing a nick including a free 5' end and a free 3' end into the template strand. In some embodiments, the free 5' end can include a 5' phosphate group. The free 3' end can optionally include a hydroxyl group.

In some embodiments, the nicking includes contacting a nucleic acid duplex and nicking one or both strands of the duplex. For example, the nicking can include contacting a duplex including the template strand hybridized to the extended first primer product with a nicking agent under nicking conditions, thereby introducing one or more nicks into at least one strand of the duplex. In some embodiments, the introducing includes nicking one strand of the duplex, but not both strands of the duplex. For example, in some embodiments the template strand is nicked while the extended first primer product is not nicked. In some embodiments, both strands of the duplex are nicked, but are different positions along each strand, such that there is no double-stranded break introduced into the duplex.

In some embodiments, the nicking includes using a nicking agent to introduce nicks at random and/or multiple positions within a nucleic acid molecule. In some embodiments, the nicking includes using a nicking agent to introduce nicks at defined and preselected sites within the nucleic acid molecule, for example within a specific sequence (site-specific nicking). In some embodiments, a nicking agent can include an enzyme, light or chemical compound. For example, site-specific nicking can be performed using a site-specific nicking enzyme.

Any suitable method of nicking a nucleic acid molecule may be used. Methods of nicking nucleic acid molecules are well known in the art. For example, it is well known that nicking of nucleic acid molecules generally includes contacting the nucleic acid molecule with a nicking agent under nicking conditions. For example, nicking of a nucleic acid molecule can include nicking the nucleic acid molecule by enzymatic, photo cleaving (e.g., light) or chemical methods. In an exemplary embodiment, nicking can be conducted using a nicking enzyme. In some embodiments, a nicking enzyme can be a naturally-occurring enzyme, recombinant enzyme, mutant enzyme, variant enzyme, fusion or otherwise engineered enzyme, chemically modified enzyme, synthetic molecule, or analog, derivative or fragment thereof. In some embodiments, nicking can be coupled with an enzyme that couples a 5'→3' polymerization/degradation reaction, such as $E.$ $coli$ DNA polymerase I, $Thermus$ $aquaticus$ DNA polymerase, or T4 DNA polymerase. Typical conditions for enzymatic nicking can include reaction temperatures of about 0° C.-45° C. In some embodiments, a nicking reaction can be conducted for about 1, 2, 3, 4, 5, 6, 7, 8, 9, 10, 11, 12, 13, 14, 15, 16, 17, 18, 19, 20 or 30 minutes. A nicking reaction can be terminated or slowed by increasing the temperature, decreasing the temperature, altering the pH, altering the ions present, altering the salt conditions present, and/or addition of a chelating agent. In some embodiments, nicking can include modulating the nicking method. Modulating can optionally include: increasing or decreasing the nicking agent concentration; increasing or decreasing a cation concentration; increasing or decreasing a reaction temperature, reaction time and/or pH, and the like. The modulating can include increasing or decreasing the rate of the reaction, increasing or decreasing the yield of product of the reaction, and the like. In some embodiments, nicking can be performed in the presence of appropriate buffers and/or nucleotides (including nucleotide analogs or biotinylated nucleotides). In some embodiments, the appropriate buffer can optionally include a detergent and/or an additive. For example, a buffer can optionally include one or more detergents such as, but not limited to, TWEEN-20, SDS, TRITON, and the like. In some embodiments, an additive can include a polymer compound comprising a homo-polymeric and hetero-polymeric compound. In some embodiments, a polymer compound comprises a chain of two or more tetrahydrapyrrole monomers. In some embodiments, a tetrahydrapyrrole monomer comprises a five-membered heterocyclic ring. In some embodiments, in a chain of tetrahydropyrrole rings, one or more tetrahydropyrrole rings comprise a nitrogen atom reacted with a carbonyl or carboxylic acid compound. In some embodiments, a polymer compound comprises polyvinylpyrrolidone (e.g., povidone or crospovidone), poly(4-vinylphenol), and vinylpyrrolidone/vinyl acetate copolymer (e.g., copovidone). In some embodiments, a polymer compound comprises two or more monomers of N-vinyl-pyrrolidone, including modified polymers thereof. Modified polymers of poly(N-vinyl-pyrrolidone) comprise monofunctionalized (e.g., hydroxyl or carboxy end group), side-chain conjugates (e.g., poly- and multifunctional side chains), and grafted copolymers. In some embodiments, polyvinylpyrrolidone includes various molecular weight polymers including average molecular weights of about 5 kD-55 kD, for example 10 kD, 29 kD, 40 kD, and 55 kD molecular weight compounds. In some embodiments, an additive (e.g., polyvinylpyrrolidone (PVP)) can be present in the buffer at about 0.1-8%, or about 1-2%, or about 2-3%, or about 3-4%, or about 4-5%, or about 5-6%, or about 6-7%, or about 7-8%. In some embodiments, the appropriate buffer can include a reducing agent such as, but not limited to DTT, TCEP, and the like. In some embodiments, nicking can include translation of the nick to a new position along the nucleic acid molecule. In some embodiments, translation of a nick can include a nick translation reaction. Methods for performing nick translation reactions are known to those of skill in the art (Rigby, P. W. et al. (1977), J. Mol. Biol. 113, 237).

In some embodiments, methods for nicking nucleic acid molecules can include nicking the nucleic acid molecule using a nicking enzyme. In some embodiments, nicking enzymes include any enzyme having endonuclease activity, with or without exonuclease activity. In some embodiments, nicking enzymes include any enzyme that can catalyze nicking one or both strands of a single stranded nucleic acid molecule or of a double-stranded nucleic acid duplex. In some embodiments, nicking enzymes include any enzyme that can catalyze introducing a nick at random positions in one or both strands of a double-stranded nucleic acid. In some embodiments, nicking enzymes include any enzyme that can introduce one or more nicks at random (or nearly random) positions in either strand of a nucleic acid duplex. In some embodiments, nicking enzymes include any enzyme that can introduce one or more nicks in a non-specific sequence manner at any position in either strand of a nucleic acid duplex. In some embodiments, nucleic acid nicking enzymes include any wild-type or mutant deoxyribonucleases I (DNase I) enzyme isolated from any organism or tissue, or isolated as a recombinant enzyme. In some embodiments, a DNase I can be isolated from bovine. In some embodiments, a DNase I can be isolated from pancreas.

In some embodiments, the nicking enzyme can be a DNase from a family Virionaceae, such as genus *Vibrio*, which includes *Vibrio vulnificus*. In some embodiments, the nicking enzyme can be a Vvn polymerase. In some embodiments, the nicking enzyme can be a DNA polymerase from *Vibrio cholera* (Focareta and Manning 1987 Gene 53(1):31-400, or an NucM polymerase from *Erwinia chrysanthemi* (Moulard 1993 Mol. Microbiol. 8)4):685-695, or an Endo I polymerase from *E. coli* (Jekel 1995 Gene 154(1):55-59, or a Dns or DnsH polymerase from *Aeromonas hydrophila* (Chang 1992 Gene 122(1):175-180, Dodd 1999 FEMS Microbiol. Lett. 173:41-46, and Wang 2007 Nucleic Acids Research 35:584-594). In some embodiments, the nicking enzyme can be a DNase from a family Enterobacteriaceae, such as a genus *Serratia*, which includes *Serratia marcescens* (Benzonase™, U.S. Pat. No. 5,173,418).

In some embodiments, the nicking enzyme exhibits little or no preference for nicking nucleic acids at sequences having a high or low GC % content, including nucleic acids having about 0-10%, or about 10-25%, or about 25-40%, or about 40-55%, or about 55-70%, or about 70-85%, or about 85-100% GC % content.

In some embodiments, a site-specific nicking enzyme can be used to nick the nucleic acid molecule. Many site-specific nicking enzymes are known in the art. For example, New England BioLabs Inc., provides a variety of site-specific nicking enzymes including Nt.CviPII, Nb.BsmI, Nb.BbvCI, Nb.BsrDI, Nb.BtsI, Nt.BsmAI, Nt.BbvCI, Nt.BspQI, Nt.AlwI and Nt.BstNBI. As an example, the enzyme Nt.BbvCI nicks the sequence CC^TCAGC at the site denoted by the carrot. This particular sequence can provides a 5-base "key" sequence that indicates the start of a sequence read. In another example, the enzyme AscI nicks the sequence GG^CGCGCC at the site denoted by the carrot. This particular sequence can provide a 6-base "key" sequence that indicates the start of a sequence read. In yet another example, the enzyme NotI nicks the sequence GC^GGCCGC at the site denoted by the carrot. This particular sequence can provide a 6-base "key" sequence that indicates the start of a sequence read. In another example, the enzyme AsiSI nicks the sequence GCGAT^CGC at the site denoted by the carrot. This particular sequence can provide a 3-base "key" sequence that indicates the start of a sequence read.

In some embodiments, the nicking enzyme can be Nt.CviPII, Nb.BsmI, Nb.BbvCI, Nb.BsrDI, Nb.BtsI, Nt.BsmAI, Nt.BbvCI, Nt.BspQI, Nt.Alwi, or Nt.BstNBI. In some embodiments, the nicking enzyme is incubated at defined temperature for defined period with the nucleic acid molecule (or duplex) to be nicked. In a typical embodiment, the nicking enzyme is incubated with the nucleic acid molecule (or duplex) for about 5 minutes to about 30 minutes at 37° C. In some embodiments, the nicking enzyme is incubated with the nucleic acid molecule for about 5 minutes to about 30 minutes at about 50° C. In some embodiments, the nicking enzyme is incubated with the nucleic acid molecule for about 5 minutes to about 30 minutes at about 65° C. In some embodiments, the nicking enzyme can be heat inactivated after nicking and does not require a buffer exchange or clean up step, prior to advancing the method.

In some embodiments, the one or more nucleic acid molecule (e.g., the first primer, the second primer, the template strand, the first extended primer product and the second extended primer product) can include at least one scissile linkage which can be cleavable. In some embodiments, a scissile linkage can be cleavable with an enzyme, photochemical or chemical treatment. In some embodiments, the scissile linkage can be located at any position within the one or more nucleic acid molecules, including at or near a terminal end or in an interior portion of the one or more nucleic acid molecules.

In some embodiments, conditions suitable for cleaving a scissile linkage can include a pH range of about 4-10, or about 5-9, or about 6-8. In some embodiments, conditions suitable for cleaving a scissile linkage can include a temperature range of about 15-60° C., or about 20-55° C., or about 25-50° C., or about 24-45° C., or about 22-40° C., or about 20-35° C.

In some embodiments, a scissile linkage can include at least one phosphorothioate linkage. In some embodiments, a phosphorothioate linkage can be cleavable with a metal compound (Vyle 1992 Biochemistry 31:3012-3018; Sontheimer 1999 Methods 18:29-37; and Mag, 1991 Nucleic Acids Research 19:1437-1441). In some embodiments, a metal compound can include silver (Ag), mercury (Hg), copper (Cu), manganese (Mn), zinc (Zn), cadmium (Cd) or iodide ($I_2$). In some embodiments, a phosphorothioate linkage can be cleaved with a water-soluble salt that provides Ag+, Hg++, Cu++, Mn++, Zn+ or Cd+ anions. Salts that provide ions of other oxidation states can be used for nucleic acid cleavage. For example, a phosphorothioate linkage can be cleaved with a silver-containing salt, such as silver nitrate ($AgNO_3$). Double stranded DNA substrates containing a single phosphorothioate bond at the 5' end were found to be susceptible to T7 gene 6 exonuclease digestion; while comparable substrates containing four phosphorothioates were found to be resistant under the same conditions (Nikiforov 1994 Genome Research 3:285-291.

In some embodiments, a scissile linkage can include at least one acid-labile linkage. An example of an acid-labile linkage includes a phosphoramidate linkage. In some embodiments, a phosphoramidate linkage can be hydrolysable under acidic conditions, including mild acidic conditions (Shchepinov 2001 Nucleic Acids Research 29:3864-3872; Mag 1992 Tetrahedron Letters 33:7319-7322). In some embodiments, conditions suitable for cleaving a phosphoramidate linkage can include trifluoroacetic acid and a temperature range of about 15-45° C., or about 20-40° C., or about 25-35° C., or about 27-30° C.

In some embodiments, a scissile linkage can include at least one photolabile internucleosidic linkage. For example, a photolabile linkage can include an o-nitrobenzyl (Pillai 1987 in "Organic Photochemistry" ed. Padwa N Y; Walker 1988 Journal of Am. Chem. Soc. 110:7170-7177), or an o-nitrobenzyloxymethyl or p-nitrobenzyloxymehtyl group. Other examples of photolabile linkages or groups include dimethoxybenzoin carbonates (Pirrung and Bradley 1995 Journal Org. Chem. 60:1116-1117), ortho-nitrophenylethyl-type carbonates and ortho-nitrophenylethyl-type sulfonates (Hasan 1997 Tetrahedron 53:4247-4264; Giegrich 1998 Nucleosides and Nucleotides 17:1987-1996; and U.S. Pat. Nos. 5,763,599 and 6,153,744). In some embodiments, a photolabile group can be joined to a 5' or 3'-hydroxyl group of a nucleoside moiety. In some embodiments, a photolabile linkage can be cleaved with light, including short wavelength light such as UV irradiation. For example, a photolabile linkage can be cleaved with light having a wavelength of about 333-550 nm. In some embodiments, conditions suitable for cleaving a scissile linkage can include an ultraviolet photochemical reaction.

In some embodiments, a scissile linkage can include an apurinic tetrahydrofuran site. An apurinic tetrahydrofuran site can be cleavable with an endonuclease, including an endonuclease IV or apurinic/apyrimidinic endonuclease (e.g., AP endo, HAP1, Apex or Ref1).

In some embodiments, a scissile site can include at least one uracil base. In some embodiments, a uracil base can be cleaved with a uracil DNA glycosylase (UDG) (also referred to as uracil N glycosylase) or formamidopyridine [fapy]-DNA glycosylase. In some embodiments, the exemplary bi-directional sequencing methods can optionally include a template strand possessing one or more uracil located along the length of the template strand to be cleaved. For example, a first primer can be hybridized to the template strand possessing one or more uracil along its length; the first primer can be extended via template-dependent nucleotide incorporation using a polymerase and dNTPs. The resulting extended primer product/template duplex can undergo UDG digestion to create one or more nicks along the template strand. The nicks can be treated (for example, with one or more enzymes such as an endonuclease and/or an exonuclease) to degrade portions of the template strand creating one or more single stranded regions within the extended first primer product. In some embodiments, the degrading reaction can be performed or modulated by an enzyme possessing strand displacement activity and/or 5'-3' exonuclease activity. Optionally, the single stranded regions can be extended in the presence of a polymerase and dNTPs to create an extended product (that is substantially complementary to the first primer product over at least some portion of their respective lengths). The disclosed methods can therefore include a process for performing bi-directional sequencing.

In some embodiments, the disclosure relates generally to methods for generating single-stranded polynucleotides. In some embodiments, the disclosure provides methods for generating single-stranded nucleic acids. In some embodiments, the method includes hybridizing a first primer to a nucleic acid molecule, extending the first primer via polymerization under polymerization conditions, thereby forming an extended first primer product that is complementary to a portion of the nucleic acid molecule, introducing a nick into a portion of the nucleic acid molecule that is hybridized to the extended first primer product, where the nick includes a free 5' end and a free 3' end in the nucleic acid molecule; and degrading the nucleic acid molecule from the free 5' end of the nick using a degrading agent, thereby generating substantially single-stranded extended primer products. In some embodiments, the single-stranded extended primer products can be further separated from the nucleic acid molecules, for example by sodium hydroxide or heat treatment. In some embodiments, the method includes introducing a nick in a template strand hybridized to a first extended primer product, degrading a portion of the template strand with a strand displacement activity or degrading agent, thereby generating a substantially single stranded polynucleotide, where a portion of the extended first primer product remains hybridized to an undegraded portion of the template strand. Optionally, the method can further include treating the extended primer product with a separation agent to separate the extended primer product from the undegraded portion of the template strand. In some embodiments, the separated extended primer product can be captured, for example with a binding partner or capture probe, and sequenced. In some embodiments, the captured extended primer product can be hybridized to a second primer and sequenced under polymerization conditions in the presence of a polymerase and dNTPs. In some embodiments, the sequencing can include obtaining sequencing information from some or all of the nucleotides incorporated during the first primer extension and/or the extension of the single-stranded regions within the extended first primer product. In some embodiments, sequencing can occur when a template strand is attached to a support such as, but not limited to a solid support. In some embodiments, the support can include a bead, microsphere, nanopore, well, trough, groove, channel, flowcell, microwell, slide or other attachment surface.

In some embodiments, the method includes introducing a nick into the template strand hybridized to the first extended primer product, degrading a portion of the template strand with a degrading agent, thereby generating a substantially single stranded polynucleotide. In some embodiments, the introducing includes nicking the template strand at one or more sites in the template strand, and then digesting the template strand from at least one nick to form a single-stranded region.

In some embodiments, the introducing includes nicking a nucleic acid molecule, for example a template strand, and then moving the position of the nick using one or more nick translating enzymes. The nick translation enzyme can include any enzyme that can move the position of the at least one nick to a new position along the nucleic acid strand. In some embodiments, moving the position of the nicks can be catalyzed by one or more enzymes in the presence of a plurality of nucleotides. In some embodiments, moving the position of the at least one nick can include performing a nick translation reaction. In some embodiments, an enzyme that catalyzes nick translation includes an enzyme that couples a 5'→3' polymerization/degradation reaction, or an enzyme that couples a 5→3' polymerization/strand displacement reaction. In some embodiments, a nick translation reaction can be catalyzed by any nucleic acid polymerase having a 5→3' nucleotide polymerization activity and a 5→3' exonuclease activity. In some embodiments, a nick translation reaction can be catalyzed by any nucleic acid polymerase lacking a 3→5' exonuclease activity. In some embodiments, a nick translation reaction can be catalyzed by any DNA polymerase. In some embodiments, a nick translation reaction can be catalyzed by any Family A DNA polymerase (also known as pol I family) or any Family B DNA polymerase. In some embodiments, a nick translation reaction can be catalyzed by Klenow fragment. In some embodiments, a nick translation reaction can be catalyzed by *E. coli* Polymerase I. In some embodiments, a nick translation reaction can be catalyzed by one or more thermostable enzymes having 5→3' nucleotide polymerization activity and a 5→3' exonuclease activity. In some embodiments, a nick translation thermostable enzyme includes Taq polymerase (from Therms *aquaticus*), Tfi polymerase (from *Thermus filiformis*), Pfu polymerase (from *Pyrococcus furiosus*), Tth (from *Thermus thermophilus*), Pow polymerase (from *Pyrococcus woesei*), Tli polymerase (from *Thermococcus litoralis*), Pol I and II polymerases (from *Pyrococcus abyssi*), and Pab (from *Pyrococcus abyssi*), or a fragment thereof capable of catalyzing the nick translation reaction.

In some embodiments, a nick translation reaction can be catalyzed by one or more enzymes that couples a 5' to 3' DNA polymerization and strand displacement reaction. In some embodiments, a strand displacing polymerase includes Taq polymerase, Tfi polymerase, Bst polymerase (from *Bacillus stearothermophilus*), Tli polymerase, 9° N polymerase, and phi29 polymerase, or a fragment thereof capable of catalyzing a DNA polymerization and strand displacement reaction.

In some embodiments, a nick translation reaction can be catalyzed by a combination of a helicase and a DNA polymerase.

In some embodiments, performing any one or more of the hybridization reaction, nicking reaction, degrading reaction or nick translation reaction can include modulating the reaction. Modulating can optionally include: increasing or decreasing an enzyme concentration; by increasing or decreasing the nucleotide concentration; by increasing or decreasing the cation concentration; by increasing or decreasing a reaction temperature, reaction time and/or pH, and the like. The modulating can include increasing or decreasing the rate of the reaction, increasing or decreasing the yield of product of the reaction, and the like.

In some embodiments, the method further includes degrading at least one nucleic acid molecule at any point in time during the sequencing process. As used herein, the term "degrading" and its variants refer to any process whereby the physical integrity of at least some portion of a nucleic acid strand is disrupted sufficiently that a polymerase cannot process along that portion of the nucleic acid strand. In some embodiments, "degrading" can include treating the nucleic acid molecule to be degraded with a degrading agent. In some embodiments "degrading" can include disruption of the 5'-3' phosphodiester bonds between any two or more contiguous nucleotides within the region that is degraded. In some embodiments, "degrading" includes processes whereby the phosphodiester bonds remain intact while the base pairing interactions of any two or more contiguous nucleotides within the degraded region with corresponding residues in another nucleic acid strand are disrupted, or the physical integrity of the degraded region is otherwise undermined. In some embodiments, the degrading agent can be site-specific to a site within the nucleic acid; for example, the degrading agent may cleave the nucleic acid molecule in a site-specific manner. In some embodiments, the nucleic acid molecule to be degraded, which can include the template molecule, an extended primer product, or both, can include a site that is selectively recognized by the degrading agent; optionally, the site can also be cleaved or otherwise degraded by the degrading agent. In some embodiments, the degrading agent can include a restriction enzyme, and the nucleic acid molecule to be degraded can include a restriction recognition site. In some embodiments, the degrading can include degrading a portion of at least one strand within a nucleic acid duplex. In some embodiments, the degrading includes degrading a portion of at least one strand of duplex after the strand has been nicked. The degrading can include using a degrading agent to disrupt the integrity of the nucleic acid strand. The degrading agent can optionally bind to the 5' end of a nick within the nucleic acid strand and degrade the nucleic acid strand in the 5' to 3' direction. Alternatively, the degrading agent can optionally bind to the 3' end of a nick within the nucleic acid strand and degrade the nucleic acid strand in the 3' to 5' direction. In some embodiments, a degrading agent is added to a nucleic acid duplex formed via hybridization of the extended first primer product and the nucleic acid template. In some embodiments, the degrading agent degrades one or more free 5'ends present within the nucleic acid duplex.

In some embodiments, the degrading agent is an enzyme that is capable of degrading a nucleic acid molecule via exonucleolytic digestion, either in the 3' to 5' direction, or the 5' to 3' direction, or both. For example, the enzyme can be Exonuclease I or Exonuclease III, which possess 3' to 5' exonuclease activity. For example, the enzyme can be T5 or T7 exonuclease, which possesses 5' to 3' exonuclease activity. In a typical embodiment, a duplex including the template strand hybridized to the first extended primer product is nicked within the template strand and contacted with a 5' to 3' exonuclease (e.g., T5 or T7 exonuclease), which binds to the 5' end of the nick within the template strand and degrades a portion of the template strand located 3' of the nick, where the degradation occurs in the 5' to 3' direction.

In some embodiments, the method includes degrading at least a portion of the template strand prior to extending the second primer. In some embodiments, the degrading is performed before or after hybridizing the second primer to the extended first primer product. In some embodiments, the degradation reaction can be modulated by: increasing or decreasing an enzyme concentration; by increasing or decreasing the cation concentration; by increasing or decreasing a reaction temperature, reaction time and/or pH, and the like.

In some embodiments, the method includes displacing at least a portion of the template strand prior to extending the second primer. In some embodiments, the displacing is performed before or after hybridizing the second primer to the extended first primer product. In some embodiments, the displacing reaction can be performed or modulated by an enzyme possessing strand displacement activity and/or 5'-3' exonuclease activity.

In some embodiments, a primer can be treated with chain-terminating nucleotide such as ddATP, ddGTP, ddCTP or ddTTP to prevent continued extension of the primer. In this example, the addition of a chain-terminating nucleotide which lacks a 3'-OH group required for the formation of a phosphodiester bond with an adjacent nucleotide, can inhibit further forward primer extension. In some embodiments, the primer can be treated with apyrase or phosphatase after the polymerase fill-in or primer extension step. In some embodiments, the primer is substantially resistant to degradation, or includes a nucleic acid sequence that is substantially resistant to degradation. For example, a primer can include at least one locked nucleic acid (LNA). A locked nucleic acid can be resistant to cleavage or degradation by a degrading agent (e.g., exonuclease). In another example, a primer can include at least one phosphorothioate linkage. A phosphorothioate linkage can be resistant to exonuclease cleavage (e.g., exonuclease III). In another example, a primer can include at least one nuclease-resistant linkage. In some embodiments, a nuclease-resistant primer can be hybridized to the template strand.

Generally, the nucleic acid obtained by extension of a first primer and/or a second primer can be sequenced using one or more enzymes. In a typical embodiment, the enzyme is a polymerase. In some embodiments, the sequencing reaction can be modulated by: increasing or decreasing an enzyme concentration; by increasing or decreasing the nucleotide concentration; by increasing or decreasing the cation concentration; by increasing or decreasing a reaction temperature, reaction time and/or pH, and the like. In some embodiments, sequencing reactions can be performed in the presence of appropriate buffers. In some embodiments, a sequencing buffer can optionally include a detergent and/or an additive. For example, the buffer can include one or more detergents such as, but not limited to, TWEEN-20, SDS, TRITON, and the like. In some embodiments, the sequencing buffer can include an additive such as, but not limited to, polyvinylpyrrolidone (e.g., povidone or crospovidone), poly (4-vinylphenol), and vinylpyrrolidone/vinyl acetate copolymer (e.g., copovidone). In some embodiments, the additive can include two or more monomers of N-vinyl-pyrrolidone, including modified polymers thereof. Modified polymers of poly(N-vinyl-pyrrolidone) comprise monofunctionalized (e.g., hydroxyl or carboxy end group), side-chain conjugates (e.g., poly- and multifunctional side chains), and grafted copolymers. In some embodiments, polyvinylpyrrolidone includes various molecular weight polymers including average molecular weights of about 5 kD-55 kD, for example 10 kD, 29 kD, 40 kD, and 55 kD molecular weight compounds. In some embodiments, an additive (e.g., polyvinylpyrrolidone (PVP)) can be present in the buffer at about 0.1-8%, or about 1-2%, or about 2-3%, or about 3-4%, or about 4-5%, or about 5-6%, or about 6-7%, or about 7-8%. In some embodiments, a sequencing reaction can be conducted in the presence of one or more reducing agents such as dithiothreitol (DTT) or tris(2-carboxyethyl)phosphine (TCEP).

In some embodiments, the disclosure generally relates to methods for obtaining sequence information from a nucleic acid template linked to a support, including hybridizing a first primer to a template strand linked to a support, sequencing a portion of the nucleic acid template by synthesis, where the sequencing by synthesis includes extending the first primer via template-dependent nucleic acid synthesis, thereby forming an extended first primer product that is complementary to a portion of the nucleic acid template. In some embodiments, the method further includes introducing a nick into a portion of the template strand that is hybridized to the extended first primer product, where the nick includes a free 5' end and a free 3' end in the template strand, degrading a portion of the template strand from the free 5' end of the nick using a degrading agent, where a portion of the extended first primer remains hybridized to an undegraded portion of the template strand, and sequencing at least some of the single-stranded portion of the extended first primer by synthesis. In some embodiments, substantially all of the extended first primer product is sequenced. In some embodiments, substantially all of the single-stranded portion of the extended first primer is sequenced. In some embodiments, the first primer provides sequence information in a forward or first direction. In some embodiments, sequencing of the single-stranded portion of the extended first primer product provides sequencing information in a reverse or second direction. In some embodiments, the method provides a process by which to obtain bi-directional sequencing information from a template strand. In some embodiments, bi-directional sequencing can improve sequencing throughput and/or sequencing accuracy as compared to a single end sequencing reaction (e.g., a forward or reverse sequencing reaction). In some embodiments, bi-directional sequencing includes label-free or ion based sequencing. In some embodiments, bi-directional sequencing includes optically detectable or fluorescence based sequencing. In some embodiments, the template strand can be linked to the support through the 5' end of the template strand. In some embodiments, the template strand can be linked to the support through at least one nucleotide in the template strand that can be situated 5' of the nick site in the template. In some embodiments, the first primer is resistant to degradation by the degrading agent. In some embodiments, the extended first primer product is resistant to degradation by the degrading agent. In some embodiments, the degrading agent can include a 5'-3' exonuclease, and the degrading can further include digesting the template strand from the free 5' end of the nick using the 5'-3' exonuclease. In some embodiments, sequencing of at least some portion of the single-stranded portion of the extended first primer product can include extending the free 3' end of the nick via nucleic acid synthesis, thereby synthesizing a nucleic acid molecule that is complementary to at least some portion of the single-stranded portion of the extended first primer. In some embodiments, sequencing at least some of the single-stranded portion of the extended first primer product can include hybridizing a second or reverse primer to a sequence within the single-stranded portion of the extended first primer product, and extending the second or reverse primer using a polymerase. In some embodiments, the polymerase includes a thermostable DNA polymerase.

In some embodiments, the degrading agent can initiate degradation at the free 3' end of a nick. In some embodiments, the degrading agent can catalyze nucleic acid degradation (e.g., exonuclease activity) coupled with nucleotide polymerization. In some embodiments, the degrading agent can catalyze degrading coupled with nucleotide polymerization in a 5' to 3' direction. In some embodiments, the degrading agent can catalyze template-dependent nucleotide polymerization. In some embodiments, the degrading agent can generate a nucleic acid molecule that is at least partially complementary to the extended first primer. In some embodiments, the degrading agent includes a polymerase. In some embodiments, the order of polymerized nucleotides (e.g., catalyzed by the polymerase) can be monitored to determine the nucleotide sequence of the nucleic acid molecule. In some embodiments, the sequencing can comprise sequencing at least some of the single-stranded portion of the extended first primer. In some embodiments, the sequencing can comprise sequencing at least some of the single-stranded portion of the extended first primer product and can further include hybridizing a reverse primer to a sequence within the single-stranded portion of the extended first primer product, and extending the reverse primer using a polymerase.

In some embodiments, methods for nucleic acid sequencing include hybridizing a first primer to a distal end of a nucleic acid strand having a distal and proximal end, where the proximal end of the nucleic acid strand is linked to a solid support, extending the hybridized first primer in the direction of the proximal end of the nucleic acid strand and the solid support, thereby forming an extended first primer product that is complementary to a portion of the nucleic acid strand and obtaining a first sequencing read. In some embodiments, the method can further include introducing a site-specific nick into the proximal end of the nucleic strand hybridized to the extended first primer product, degrading a portion of the nucleic acid strand, thereby generating a single-stranded portion within the extended first primer product, where a portion of the extended first primer product remains hybridized to the nucleic acid strand and extending the single-stranded portion within the extended first primer product, thereby obtaining a second sequencing read. In some embodiments, extending is performed via template-dependent nucleic acid synthesis. In some embodiments, the first primer or the extended first primer product is nuclease resistant. In some embodiments, the solid support includes an Ion Sphere Particle (ISP). In some embodiments, the nucleic acid sequencing includes bi-directional sequencing. In some embodiments, the sequencing includes a first or forward sequencing read coupled with a second or reverse sequencing read. In some embodiments, the sequencing includes obtaining sequencing information that is reversed relative to sequencing information obtained in an anti-parallel orientation. In some embodiments, the nucleic acid sequencing is label-free or ion based sequencing. In some embodiments, introducing a site-specific nick is performed by an enzyme. In some embodiments, the site-specific nicking enzyme is a restriction enzyme. In some embodiments, extending the first primer or second primer is performed by a DNA polymerase. In some embodiments, the nucleic acid to be sequenced is a DNA, cDNA, RNA, mRNA, or DNA/RNA hybrid. In some embodiments, the nucleic acids to be sequenced are obtained from a laboratory, a morgue, a clinical specimen (e.g., FFPE or biopsies), a DNA database, a patient (e.g., a hair, blood or saliva sample), a living organism, or from the circulatory system of mammals (e.g., as cell-free circulating DNA).

In some embodiments, the methods for nucleic acid sequencing can further comprise consolidating the first and second sequencing reads (e.g. FIG. 4). In some embodiments, consolidating can comprise aligning the first and second sequencing reads against a reference sequence. In some embodiments, aligning the first and second sequencing reads against a reference sequence can determine the presence of deletions, insertions, variations, inversions, translocations, mutations or mismatches in the nucleic acid strand as compared to the reference sequence. In some embodiments, paired-end sequencing methods according to the disclosure can detect splice variants and fusion transcripts. In some embodiments, aligning the first and second sequencing read can identify the nature of the mutations, mismatches, insertions, deletions or variations in the nucleic acid strand.

For example, in some embodiments the disclosure relates generally to a method for obtaining sequence information from a nucleic acid template linked to a support in both directions, comprising: hybridizing a first primer including to a template strand linked to a support. The template strand can include a nicking site, for example a site specific nicking site. The first primer can then be used to prime extension in the "forward" direction, thereby sequencing a portion of the nucleic acid template by synthesis in the "forward" direction. The sequencing can include extending the first primer via template-dependent nucleic acid synthesis using a polymerase, thereby forming an extended first primer product that is complementary to a portion of the nucleic acid template. The extending optionally proceeds past nicking site in the template, such that the extended first primer product includes sequence that is complementary to the nicking site in the template strand. The extended first primer product can be hybridized to the nucleic acid template to form a first nucleic acid duplex, of which the template strand is linked to the support.

In some embodiments, the template nucleic acid strand can be an isolated DNA nucleic acid molecule. In some embodiments the template nucleic acid strand can include a nucleic acid molecule prepared from emulsion PCR or bridge PCR. In some embodiments, the template nucleic acid strand can be enzymatically prepared from high molecular weight DNA, for example using an Ion Xpress Plus Fragment Library Kit (Life Technologies, Part No. 4468987). In some embodiments, the template nucleic acid strand can be prepared from sheared DNA such as mechanically sheared DNA or chemically treated DNA such as formalin-fixed paraffin-embedded (FFPE) DNA. In some embodiments the template nucleic acid strand includes an insert length of between about 100 and about 500 base pairs. In some embodiments the template nucleic acid strand includes an insert length of greater than 500 base pairs, greater than 600 base pairs, or more. In some embodiments, the length of the template strand coupled with bi-directional sequencing allows for highly precise alignment of DNA reads of high quality (>1 gigabyte of data at AQ17). In some embodiments, the length of the template strand coupled with bi-direction sequencing allows for highly precise alignment of DNA reads of high quality (>1 gigabyte of data at AQ20)

in both the forward and/or reverse read (e.g., Example 22). In some embodiments, the first primer is referred to as the "forward" primer and the extended first primer product (EFPP) is referred to as the extended forward primer product. The sequencing can optionally include detecting a byproduct of at least one nucleotide incorporation. In some embodiments, detecting a byproduct of at least one nucleotide incorporation can be achieved using a field effect transistor (FET). In some embodiments, detecting a byproduct of at least one nucleotide incorporation can occur using an ion-sensitive field effect transistor (ISFET). In some embodiments, the byproduct of nucleotide incorporation can include a hydrogen ion, an inorganic pyrophosphate or an inorganic phosphate. In some embodiments, the sequencing can optionally include detecting the incorporation of an optically labeled nucleotide.

In some embodiments, the method further includes introducing a nick into the first nucleic acid duplex. Typically, the nick is introduced into a portion of the template strand that is hybridized to the extended first primer product. In some embodiments, introducing a nick into the first nucleic acid duplex can include nicking the nicking site in the template strand using a suitable nicking agent. For example, the nicking site in the template strand can be a site specific nicking site, and the nicking agent can be a nicking enzyme capable of nicking the site specific nicking site. Typically, the nick includes a free 5' end and a free 3' end.

In some embodiments, the method further includes degrading a portion of the template strand. The degrading agent can include a 5'-3' exonuclease, and the degrading further includes digesting the template strand from the free 5' end of the nick using the 5'-3' exonuclease. In a typical embodiment, the degrading includes degrading the template strand from the free 5' end of the nick in the 5' to 3' direction using a suitable degrading agent (e.g., a 5' to 3' exonuclease), while leaving intact or undegraded the 3' end of the nick and any nucleotides that are covalently linked to the free 3' end of the nick, either directly or through other nucleotides (such intact portion including the 3' end of the nick and any nucleotides covalently linked thereto being referred to as the "residual portion" of the template strand). In some embodiments, the degrading generates a single-stranded portion of the extended first primer product, wherein the residual portion of the template strand remains hybridized to a region within the extended first primer product. In some embodiments, a removal or wash step is carried out prior to extension of the single-strand portion of the template strand but after extension of the extended first primer product.

In some embodiments, the method further includes sequencing at least some of the single-stranded portion of the extended first primer product. Such sequencing can include extending the free 3' end of the nick via nucleic acid synthesis, thereby synthesizing a nucleic acid molecule that is complementary to at least some of the single-stranded portion of the extended first primer. For example, in a typical embodiment the residual portion of the template strand can be used to prime extension in the "reverse" direction, thereby sequencing a portion of the nucleic acid template by synthesis in the "reverse" direction. The sequencing by synthesis can include extending the residual portion of the template strand via template-dependent nucleic acid synthesis using a polymerase, thereby obtaining a "reverse" read of the template strand. Alternatively, in some embodiments sequencing at least some of the single-stranded portion of the extended first primer product can include use of a separate primer. For example, such sequencing can include hybridizing a reverse primer to a sequence within the single-stranded portion of the extended first primer, and extending the reverse primer using a polymerase. The sequencing can optionally include detecting a byproduct of at least one nucleotide incorporation using a field effect transistor (FET). In some embodiments, the method further comprises obtaining both a first (forward) and a second (reverse) sequencing read. In some embodiments, the method further comprises obtaining both a sense sequencing read and an antisense sequencing read. In some embodiments, the method includes sequencing in a first orientation, optionally followed by sequencing in an orientation that is reversed relative to the first sequencing read. In some embodiments, the first and second sequencing reads are aligned against a reference sample. In some embodiments, the first and second sequencing reads are aligned against a reference sample to determine the presence of variants in the first or second sequencing reads as compared to the reference sample. In some embodiments, the first and second reads are aligned to provide a de novo nucleic acid sequence. In some embodiments, the first and/or second sequencing reads can be used to determine the presence of one or more insertions, deletions, mismatches or other nucleotide errors in the first or second sequencing reads when compared against a reference sample. In some embodiments, the first and second sequencing reads are consolidated. In some embodiments, the consolidation process improves sequencing accuracy when compared to a non-consolidated sequencing read. In some embodiments, the consolidation process improves sequencing accuracy when compared to a single end sequencing read.

In some embodiments, the template strand is linked to the support through the 5' end of the template strand. In some embodiments, the template strand is linked to the support through at least one nucleotide in the template that is situated 5' of the nick site in the template.

In some embodiments, the first primer is resistant to degradation by the degrading agent. For example, where the degrading agent is T7 exonuclease, the first primer can include one or more nucleotides that are resistant to digestion by T7 exonuclease. In another example, where the degrading agent is T5 exonuclease, the first primer can include one or more nucleotides that are resistant to digestion by T5 exonuclease.

In some embodiments, additional components may be added to the bi-directional sequencing method such as, but not limited to, cations, salts, polypeptides, polymers, detergents, surfactants and excipients to optimize one or more of the steps. In some embodiments, additional components such as, but not limited to, cations, salts, polypeptides, polymers, detergents, surfactants and excipients can be added to one or more of the degrading, nicking, extension or sequencing steps.

In some embodiments, the sequencing and/or extension reactions can be optimized by one of ordinary skill in the art to achieve the desired sequencing information such as sequencing accuracy, yield, total throughput and/or nucleotide sequence information. In some embodiments, the sequencing throughput achieved in a bi-directional sequencing reaction (i.e., totality of forward and reverse reads) can exceed 1, 2, 3, or 4 gigabytes of data at AQ20. In some embodiments, the sequencing throughput achieved with a bi-directional sequencing reaction can exceed 1, 2, 3, or 4 gigabytes of data or more at AQ17.

In some embodiments, the disclosure relates generally to systems for sequencing nucleic acids, comprising: template nucleic acids, one or more primers, one or more polymerases, one or more degrading agents, and deoxyribonucleotide triphosphates. In some embodiments, the disclosure generally relates to systems for sequencing nucleic acids in a first (forward) and second (reverse) orientation. In some embodiments, the disclosure generally relates to systems for sequencing nucleic acids in a bi-directional orientation. In some embodiments, systems for sequencing nucleic acids further comprise one or more nicking enzymes. In some embodiments, systems for sequencing nucleic acids further comprise any combination of: buffers; cations; solid-supports; one or more nick translation enzymes, reagents for nucleic acid purification; reagents for nucleic acid amplification; endonuclease(s); kinase(s); phosphatase(s); and/or nuclease(s).

Provided herein are compositions for immobilizing a substantially complementary sequence such as, but not limited to, a sequencing primer in an orientation that is reversed compared to the orientation of the template strand.

Provided herein are primers comprising at least one functional sequence or site in any combination and in any order, including: a cleavage resistant site, a priming sequence, a cross-linking sequence, a restriction endonuclease recognition sequence, and/or a nicking endonuclease recognition sequence. The functional sequence or site permits nucleic acid manipulations, such as cleavage, primer extension, digestion, strand displacement or cross-linking. In some embodiments, the primers can function as a catalyst for primer extension reactions.

In some embodiments, the primers can be hybridized to the template strand. The various functional sequences or sites on the primers permit various nucleic acid manipulations that can be used to generate extended primer products that include a sequence substantially complementary the template strand with an orientation that is reversed compared to the template strand.

In some embodiments, the disclosure relates generally to kits for sequencing nucleic acids. In some embodiments, the disclosure relates generally to kits for sequencing nucleic acids in a first (forward) and second (reverse) orientation. In some embodiments, the disclosure relates generally to kits for improving sequencing accuracy. In some embodiments, the disclosure relates generally to kits for generating single-stranded nucleic acids. In some embodiments, the kits include any reagent that can be used to conduct nucleic acid sequencing. In some embodiments, kits for sequencing include any reagent that can be used to conduct nucleic acid sequencing in a bi-directional method.

In some embodiments, the disclosure relates generally to kits comprising a primer having an exonuclease resistant nucleotide sequence substantially complementary to the template nucleic acid to be sequenced, a polymerase, dNTPs, a nicking enzyme and a degrading enzyme. In some embodiments, the kit can further include a support and/or one or more primers or adaptors that can be used to link the template nucleic acid to the support. In some embodiments, the exonuclease resistant nucleotide sequence can include one, two, three, four, five or more phosphorothioate residues. In some embodiments, the kit can further include a support such as a bead, particle, microparticle, slide, array, and the like.

In some embodiments, the kits include any combination of: buffers; cations; one or more primers; one or more enzymes; one or more degrading agent(s); one or more nucleic acid nicking enzyme(s); one or more nick translation enzyme(s); one or more nucleotides; one or more deoxyribonucleotide triphosphates; reagents for nucleic acid purification; and/or reagents for nucleic acid amplification. In some embodiments, the kits include any combination of: endonuclease(s); exonuclease(s); polymerase(s); ligase(s); kinase(s); phosphatase(s); and/or nuclease(s).

Embodiments of the present teachings can be further understood in light of the following examples, which should not be construed as limiting the scope of the present teachings in any way. Although the present description described in detail certain exemplary embodiments, other embodiments are also possible and within the scope of the present invention. Variations and modifications will be apparent to those skilled in the art from consideration of the specification and figures and practice of the teachings described in the specification and figures, and the claims.

EXAMPLES

Example 1

Figure 1:
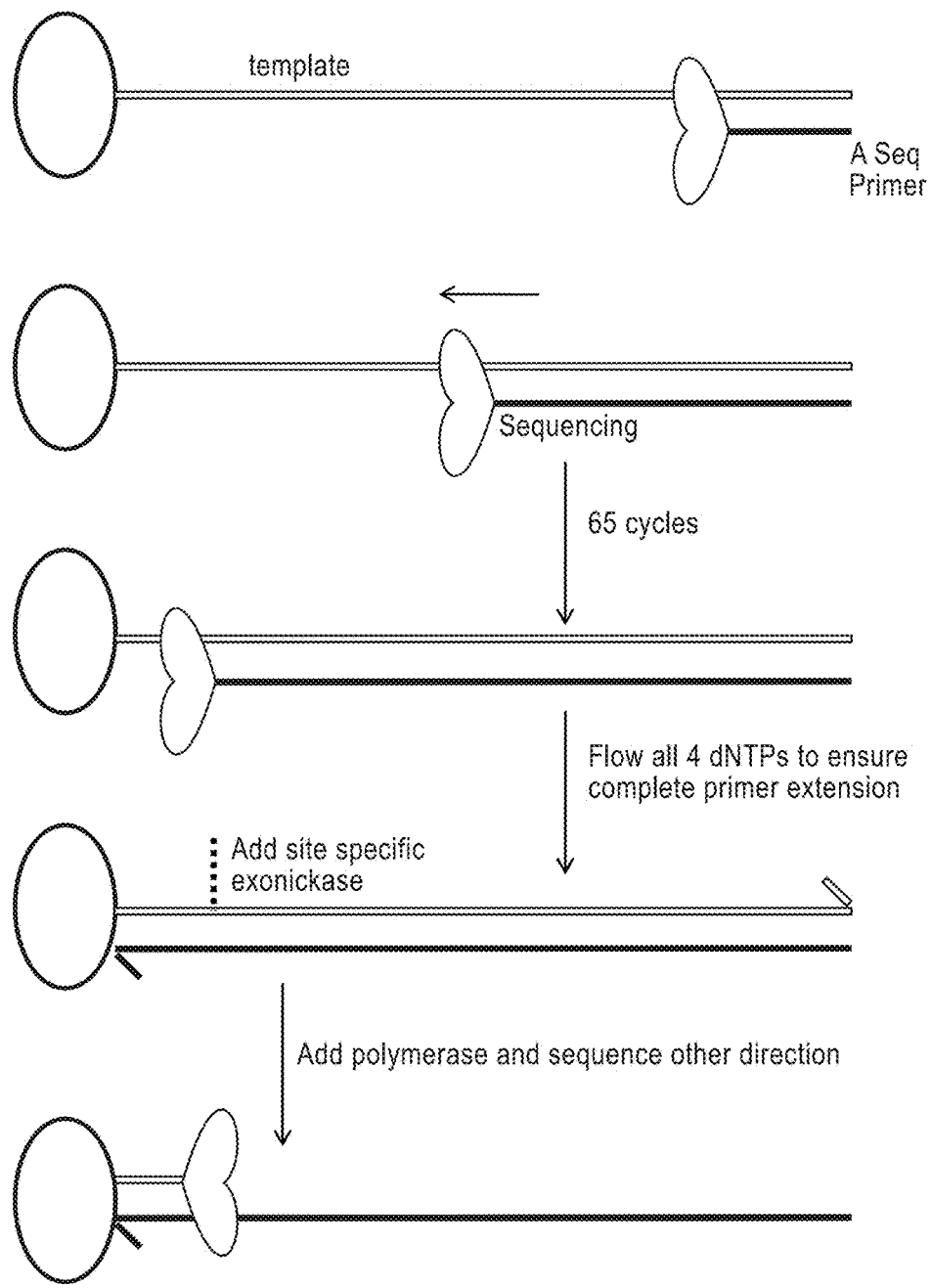
FIG. 1 is a schematic depicting an exemplary embodiment of a paired-end sequencing method according to the disclosure.

FIG. 1 depicts an exemplary embodiment according to the methods of the disclosure involving paired-end sequencing using an ion-based sequencing system. A nucleic acid template strand, which includes a site specific nicking site at or near the 5' end, is linked to a solid support (here, an Ion Sphere™ particle) through the 5' end of the template strand.

A "forward" sequencing primer (A Seq Primer) is hybridized to the 3' end of the template strand, and the hybridized primer:template system is placed within an Ion Chip, where the hybridized: template system is deposited in a microwell within the Ion Chip, which is then placed within the Ion Torrent PGM™ sequencing system (Life Technologies, CA). Nucleotides are then flowed serially into the Ion Chip, and the forward primer is extended via stepwise template-dependent nucleic acid incorporation using a polymerase to form an extended forward primer product. As each nucleotide is incorporated in a stepwise fashion into the extending forward primer, such incorporation is detected via the FET linked to the microwell in the Ion Chip, providing a "forward" sequencing read of the template strand. The forward primer is extended past the site specific nicking site in the template strand, and the resulting extended forward primer product therefore includes sequence complementary to the site-specific nicking site.

After the forward primer extension is completed (and the forward sequencing read is obtained), the Ion Chip is flushed with a solution including a nicking agent (here, a nicking enzyme that can cleave specifically at the site-specific nicking site within the template strand). Conditions are adjusted to facilitate nicking of the template strand at the site-specific nicking site in the template strand using the nicking agent (shown as site-specific exonickase).

After nicking is completed, the Ion Chip is flushed with a degrading agent (here, T7 exonuclease) that is capable of digesting the template strand from the 5' end of the nick in the 5' to 3' direction, leaving the 3' end of the nick and associated upstream template sequence intact while simultaneously creating a single-stranded region within the extended first primer product (the intact portion hereafter being referred to as the "residual portion" of the template strand). The residual portion remains hybridized to the complementary sequence in the extended forward primer product and also remains linked to the Ion Sphere™ particle at its 5' end. The residual portion of the template strand is then used to prime extension in the "reverse" direction to provide a "reverse" sequencing read. To sequence in the "reverse" direction, each of the four nucleotide types (A, C, G and T) are flushed serially into the Ion Chip, and any consequent nucleotide incorporation is detected using the FET that is operationally associated with the microwell including the Ion Sphere™ particle and associated nucleic acid molecule.

Typically, an exchange of reagents into the Ion Chip is preceded by a wash step to remove prior reagents (enzymes, nucleotides, etc) so that the succeeding reaction is not contaminated by reagents from prior steps.

Example 2

Figure 2:
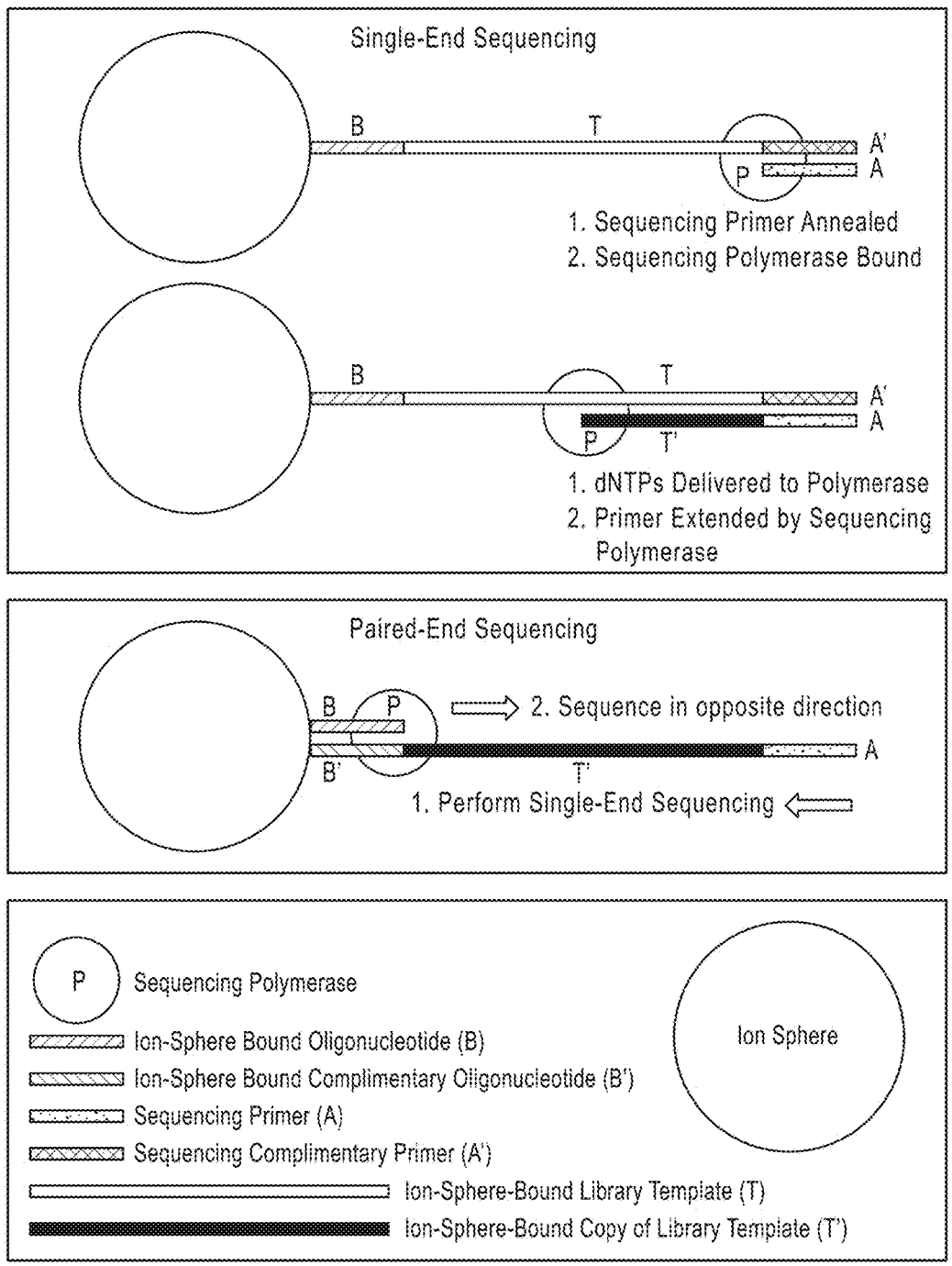
FIG. 2 is a schematic depicting an exemplary embodiment of a paired-end sequencing method according to the disclosure as compared to single-end sequencing.

FIG. 2 depicts an exemplary embodiment according to methods of the disclosure involving paired-end sequencing using an ion-based sequencing system. A nucleic acid template strand (T), which includes a site specific nicking site at or near the 5' end, is linked to a solid support (here, an Ion Sphere™ particle) through the 5' end of the template strand.

A "forward" sequencing primer (green primer (A)) is hybridized to the 3' end of the template strand (yellow primer complement (A')), and the hybridized primer:template system is placed within an Ion Chip, where the hybridized: template system is deposited in a microwell in the Ion Chip, which is placed within an Ion Torrent PGM™ sequencing system. A sequencing polymerase (P) is bound to the hybridized: template system. dNTPs are then flowed serially into the Ion Chip, and the forward primer is extended via stepwise template-dependent nucleic acid incorporation using a sequencing polymerase to form an extended forward primer product (T'). As each nucleotide is incorporated in a stepwise fashion into the extending forward primer, such incorporation is detected via the FET linked to the microwell in the Ion Chip, providing a "forward" sequencing read of the template strand.

After the forward primer extension is completed (and the forward sequencing read is obtained), the Ion Chip is flushed with a solution including a nicking agent (here, a nicking enzyme that can cleave specifically at a site-specific nicking site within the template strand). Conditions are adjusted to facilitate nicking of the template strand at the site-specific nicking site in the template strand using the nicking agent.

After nicking is completed, the Ion Chip is flushed with a degrading agent that is capable of digesting the template strand from the 5' end of the nick in the 5' to 3' direction, leaving the 3' end of the nick and associated upstream template sequence intact (the intact portion hereafter being referred to as the "residual portion" of the template strand (Ion-Sphere Bound Oligonucleotide)). The residual portion remains hybridized to the complementary sequence in the extended forward primer product and also remains linked to the Ion Sphere™ particle at its 5' end. The residual portion is then used to prime extension in the "reverse" direction to provide a "reverse" sequencing read. To sequence in the "reverse" direction, each of the four nucleotide types (A, C, G and T) are flushed serially into the Ion Chip, and any consequent nucleotide incorporation is detected using the FET that is operationally associated with the microwell including the Ion Sphere™ particle and associated nucleic acid. Typically, an exchange of reagents into the Ion Chip is preceded by a wash step to remove prior reagents (enzymes, nucleotides, etc) so that the succeeding reaction is not contaminated by reagents from prior steps.

Example 3

Figure 3:
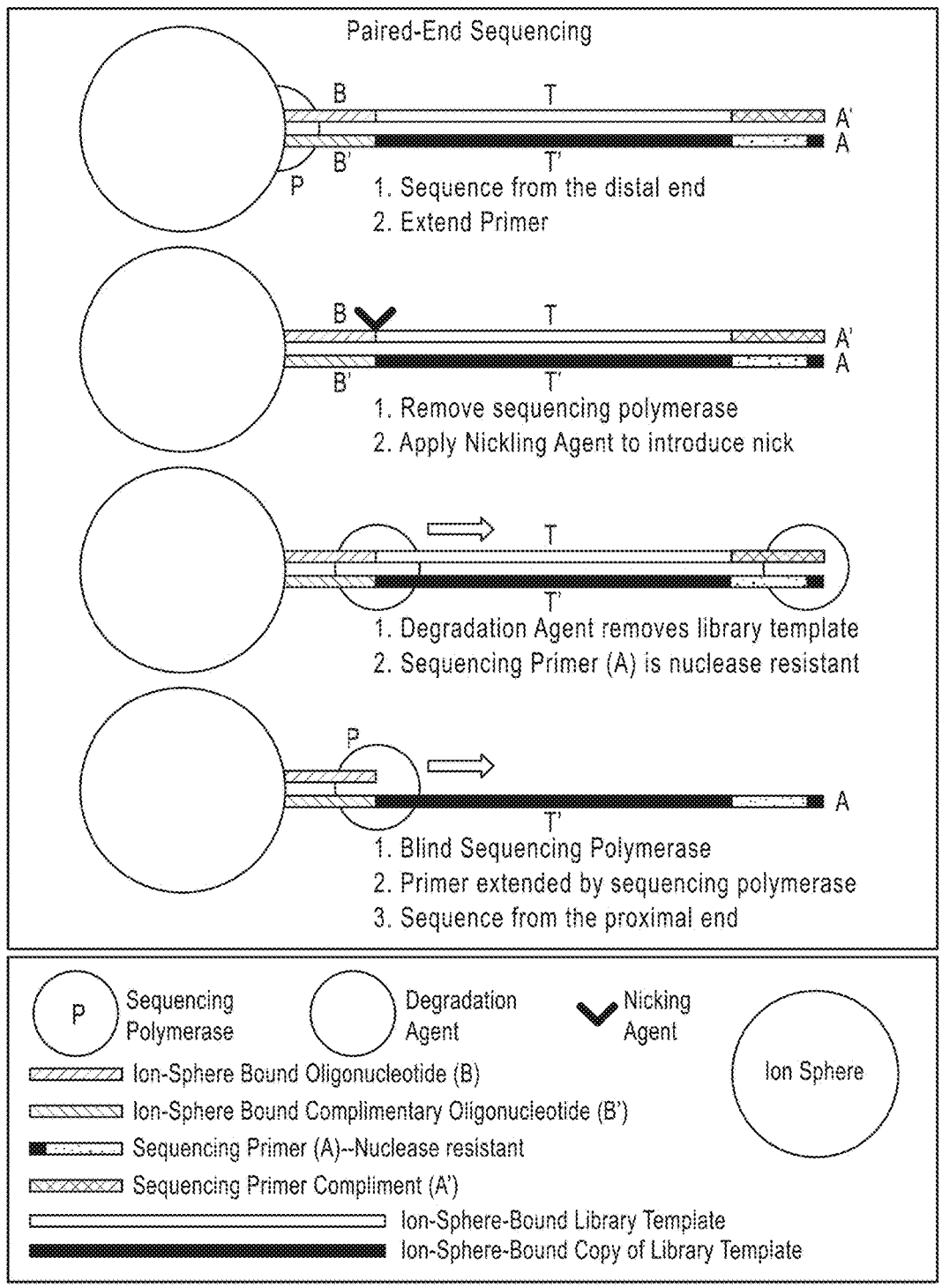
FIG. 3 is a schematic depicting an exemplary embodiment of a paired-end sequencing method according to the disclosure.

FIG. 3 depicts an exemplary embodiment according to the methods of the disclosure involving paired-end sequencing using an ion-based sequencing system. A nucleic acid template strand (T), which includes a site specific nicking site at or near the 5' end, is linked to a solid support (here, an Ion Sphere™ particle) through the 5' end of the template strand.

A "forward" sequencing primer (green primer (A)) is hybridized to the 3' end of the template strand (yellow primer complement (A')), and the hybridized primer:template system is deposited in a microwell within an Ion Chip, which is placed within an Ion Torrent PGM™ sequencing system. A sequencing polymerase (P) is bound to the hybridized: template system. dNTPs are then flowed serially into the Ion Chip, and the forward primer is extended via stepwise template-dependent nucleic acid incorporation using a sequencing polymerase to form an extended forward primer product (T'). As such, the extended forward primer product is sequenced from the distal end. As each nucleotide is incorporated in a stepwise fashion into the extending forward primer, such incorporation is detected via the FET linked to the microwell in the Ion Chip, providing a "forward" sequencing read of the template strand. The forward primer is extended past the site specific nicking site in the template strand (denoted by a carot), and the resulting extended forward primer product therefore includes sequence complementary to the site-specific nicking site.

After the forward primer extension is completed (and the forward sequencing read is obtained), the Ion Chip is flushed with a solution that removes the sequencing polymerase from the template and/or extended forward primer product. Conditions are adjusted to facilitate degradation of the template strand by applying a degrading agent (denoted as dark circle) to the Ion Chip. The degrading agent digests the template strand from the 5' end of the nick in the 5' to 3' direction, leaving the 3' end of the nick and associated upstream sequence intact (the intact portion hereafter being referred to as the "residual portion" of the template strand). The 3' sequencing primer attached to the extended primer product (A) (and optionally the ion-sphere bound oligonucleotides B and B') are resistant to the action of the degrading agent, i.e., are nuclease resistant. The residual portion of the template strand remains hybridized to the complementary sequence in the extended forward primer product and also remains linked to the Ion Sphere™ particle at its 5' end. A sequencing polymerase (P) is then added to the Ion Chip and the residual portion is then used to prime extension in the "reverse" direction to provide a "reverse" sequencing read. To sequence in the "reverse" direction, each of the four nucleotide types (A, C, G and T) are flushed serially into the Ion Chip, and any consequent nucleotide incorporation is detected using the FET that is operationally associated with the microwell including the Ion Sphere™ particle and associated nucleic acid. Typically, an exchange of reagents into the Ion Chip is preceded by a wash step to remove prior reagents (enzymes, nucleotides, etc) so that the succeeding reaction is not contaminated by reagents from prior steps. In this exemplary embodiment, the reverse read is sequenced from the proximal end.

Example 4

A paired-end library was made using the Ion Fragment Library Kit (Life Technologies, Part No. 4466464), hereby incorporated by reference in its entirety, essentially according to the protocols provided in the Ion Xpress™ Fragment Library Kit User Guide (Life Technologies, Part No. 4468987), hereby incorporated by reference in its entirety with the following modifications. E. coli genomic DNA was enzymatically digested using Ion Shear™ Reagents Kit (Life Technologies, Part No. 4468655) for 15 minutes at 37° C. to obtain a DNA fragment distribution between 75 and 200 bases. DNA fragments were then purified using Agencourt® AMPure® XP Reagent and ligated using DNA ligase at room temperature for 30 minutes to paired-end specific Ion Adapters (sold as a component of the Ion Fragment Library Kit (Life Technologies, Part No. 4466464), essentially according to the protocols provided in the Ion Xpress™ Fragment Library User Guide), which contain a Nt.BbvCI nick site and ligation to an Ion Torrent PGM™ key sequence on an alternative P1 primer (5-CCTCTC-TATGGGCAGTCGGTGATCCTCAGC-3 (SEQ ID NO: 1)). Size selection for 180 bp mean library size was performed on a Pippin Prep™ with 2% agarose cassette (Sage Science CSD-2010), essentially according to the manufacturer's instructions. The size selected DNA library was then purified, nick translated and amplified in a thermocycler for 7 cycles essentially according to the protocol of the Ion Xpress™ Fragment Library Kit User Guide. The amplified DNA was purified using Agencourt® AMPure® XP Reagent and the DNA was eluted from the beads to a new 1.5 ml LoBind Tube (Eppendorf).

An aliquot of the eluted DNA library sample was analyzed using the Agilent Technologies 2100 Bioanalyzer™ to ensure the library was of the expected size distribution. The library was quantitated to determine the library dilution that results in a concentration within the optimized target range for Template Preparation (e.g., PCR-mediated addition of library molecules onto Ion Sphere™ Particles). The DNA library is typically quantitated using an Ion Library Quantitation Kit (qPCR) (Life Technologies, Part No. 4468802) or Bioanalyzer™ (Agilent Technologies, Agilent 2100 Bioanalyzer) to determine the molar concentration of the library, from which the Template Dilution Factor is calculated. For example, instructions to determine the Template Dilution Factor by quantitative real-time PCR (qPCR) can be found in the Ion Library Quantitation Kit User Guide (Life Technologies, Part No. 4468986), hereby incorporated by reference in its entirety.

After quantification of the DNA library yield, the library was clonally amplified onto Ion Sphere™ Particles (ISPs) using the Ion Xpress™ Template Kit (Life Technologies, Part No. 4469001), hereby incorporated by reference in its entirety, essentially according to the protocols in the Ion Xpress™ Template Kit User Guide v2.0 (Life Technologies, Part No. 4469004), hereby incorporated by reference in its entirety, with the following exceptions. Double the input of recommended ISPs was used to increase overall yield. Enrichment for template positive ISPs was performed on an Ion OneTouch™ ES System (Life Technologies, Part No. 4467889) essentially according to the protocols of the Ion OneTouch™ Template Kit User Guide (Life Technologies, Part No. 4468660), hereby incorporated by reference in the their entireties. After completing the template positive enrichment step, 5 ul of 100 uM Seq Primer A (5-C*C*A*T*C*T*CATCCCTGCGTGTCTCCGAC-3, where *=phosphorothioate bond (SEQ ID NO: 2) was hybridized to 10 million template positive ISPs. The hybridized template positive ISPs where then sequenced on a Ion Torrent PGM™ sequencer (Life Technologies, Part No. 4462917), essentially according to the protocols provided in the Ion Sequencing Kit User Guide v2.0 (Life Technologies, Part No. 4468997), hereby incorporated by reference in its entirety, using Ion PGM™ Supplies Kit (Life Technologies, Part No. 4468996), Ion Sequencing Reagents Kit (Life Technologies, Part No. 4468995) and Ion PGM™ Reagents Kit (Life Technologies, Part No, 4468994). In this example, the template positive ISPs were applied to an Ion Torrent 314™ Chip (Life Technologies, Part No. 4462923) for sequencing.

Following initialization of the PGM sequencer and calibration, a first run (forward read) was performed on the 314™ chip. The 314™ experimental chip was removed from the Ion Torrent PGM™ sequencer and a dummy chip was put on the pariposer with the squid clamp shut. The insertion of the dummy chip allowed the PGM™ sequencer to maintain functionality between the two runs performed in this example, without resetting the overall system or run parameters.

100 ul of Enzyme Denaturation Solution (EDS) containing TE pH 8.0 (Sigma T9285), 2% SDS (Sigma L4522), and 50 mM NaCl (Sigma S-3014) was dispensed into the experimental 314™ chip, incubated for 1 minute at room temperature, and then removed from the 314™ chip flow cell. Three washes of 100 ul EDS followed. Next, the 314™ experimental chip was washed three times with 100 ul 1× Thermopol Buffer (New England BioLabs, Part No. B9004S). After the final wash, the remaining buffer was removed from the 314™ flow cell. 5 ul of Fill-in Solution (containing: 2 ul Sequencing Polymerase (sold as a component of the Ion Sequencing Reagents Kit, Life Technologies, Part No. 4468995), 4 ul dNTPs (1 ul of each dNTP sold as a component of the Ion Sequencing Reagents Kit, Life Technologies, Part No. 4468995), 2 ul Thermopol Buffer (New England BioLabs, Part No. B9004S) and 12 ul nuclease-free water) was added to the 314™ experimental chip and incubated at room temperature for 10 minutes with size 4 rubber gaskets covering both ports. The use of rubber gaskets was to ensure the solution did not evaporate. After incubation, 100 ul of EDS was dispensed into the 314™ experimental chip, incubated for 1 minute at room temperature and then removed from the 314™ flow cell. Three washes of 100 ul EDS followed. Next, the chip was washed three times with 100 ul 1× Buffer 4 (New England BioLabs, Part No. B7004S). After the final wash, the remaining buffer was removed from the 314™ flow cell.

5 ul of Single Stranding Solution (2 ul Buffer 4 (New England BioLabs, Part No. B7004S), 8 ul Nt.BbvCI (New England BioLabs, Part No. R0632L), 2 ul T7 Exonuclease (New England BioLabs, Part No. M0263L) and 8 ul nuclease-free water) was dispensed into the 314™ experimental chip and incubated for 30 minutes at room temperature, with size 4 rubber gaskets covering both ports. After incubation, 100 ul of EDS was dispensed into the 314™ experimental chip, incubated for 1 minute at room temperature, and then removed from the 314™ flow cell. Three washes of 100 ul EDS followed. Next, the chip was washed three times with 100 ul Annealing Buffer (sold as a component of the Ion PGM™ Reagents Kit, Life Technologies, Part No. 4468994). The annealing buffer was removed from the 314™ flow cell and 1 ul of Sequencing Polymerase (sold as a component of the Ion Sequencing Reagents Kit, Life Technologies, Part No. 4468995) diluted 1:5 in the Annealing Buffer, was added to the 314™ chip and incubated for 5 minutes at room temperature. Following incubation, the 314™ experimental chip was placed back into the PGM™ Sequencer. The second run (reverse read) was initiated and the squid wash step and wet load steps skipped.

After completion of the second run, the sequencing data for the first (forward) and second (reverse) run was obtained.

Example 5

The non-limiting, paired-end experiment described below generated two reads for each template on sequencing beads (Ion Sphere Particles™). One read is called the forward read and the other, the reverse read. Since both the forward and reverse reads are from the same DNA template molecule, the overlapping portions of the sequences are complementary. An initial pairing process determines if the forward and reverse reads overlap. Since the read sequences are obtained from two separate reactions, the first step is to establish a potential pair. If both sequencing reads are from the same microwell on the sequencing chip, they are considered a potential pair.

Next, the read sequences are aligned to a reference genome sequence (in this example, *E. coli* genomic DNA was used). The alignment of forward and reverse read sequences obtained from the PGM sequencing chip and compared to the reference sequence can be performed using any available alignment software (such as BLAST). The alignment output contains information about the starting and ending location of forward and reverse reads on the reference genome. This information determines whether the forward and reverse reads overlap based on the locations on the reference genome. The alignment output also contains information about mismatches, insertions, and deletions in the reads relative to the reference sequence. If the forward and reverse reads overlap, consolidation of paired-end reads occurs. This step requires reconstructing the original single sequence from both the forward and reverse reads, only if the reads overlap. If the forward and reverse reads do not overlap, reconstruction (or consolidation) of the original sequence was not performed.

Once the forward and reverse reads are found to overlap, both reads were consolidated into a single sequence read. In the consolidation process, the information about each reads mismatches, insertions, and deletions from alignment to the reference sequence are considered and the errors are corrected when sufficient information is available.

A "mismatch" refers to a difference in the sequence of bases from the Ion PGM™ sequencing read, as compared to the reference sequence. For example, if the reference sequence is an 'A' at a certain position, but the corresponding position in the forward or reverse read is 'T', 'C', or 'G', this is called a mismatch. An "insertion error" is defined herein as a base(s) not present in the reference sequence at the corresponding position(s); these are 'inserted' into the forward or reverse reads. A "deletion" is defined herein as a base 'deleted' from the forward and reverse reads, but is present in the reference sequence. The insertion and deletion errors can be collectedly called "indel". In the consolidation process in the overlapped regions from both forward and reverse reads, if the "indel" occurs only in one of the reads (but not in the other read), the sequence bases from the non-indel read are used for the consolidated read. If both reads showed the same indel at the same position, then the indel is retained in the consolidated read. If the indel occurs at the non-overlapped region, the indel is also retained in the consolidated read. The same principle applies to mismatches. For example, if a mismatch occurs only in one of the reads, but not in the other read from the pair, the sequenced base from the non-mismatched read is retained in the consolidated read. If mismatches occur in both reads, or in non-overlapping regions, they are retained in the consolidated read.

In this example, a paired-end library was prepared as disclosed in Example 4. Sequencing of forward and reverse reads was performed on a PGM™ Sequencer (Life Technologies, CA). The runs performed on the PGM™ sequencer were referred to as: ULT119 and ULT120. Data from the forward and reverse run is provided in Table 1, below.

TABLE 1

|  | Forward reads | Reverse reads | Total Reads |
|---|---|---|---|
| Run name | ULT119 | ULT120 |  |
| Pairable | 114,868 | 114,868 | 229,736 |

A total of 229,736 reads were obtained. The forward and reverse runs in each pair were adjusted to account of insertions, deletions, mismatches and total errors against a reference DNA sample (here, *E. coli*). Specifically, each paired-end read was consolidated to account for variations against the reference sequence. As a result, the number of consolidated reads for the above experiment was 92,665 reads. The data from the PGM sequencing runs can be found in FIGS. 5A, 5B, 6A, 6B, 7A, 7B, 8A, 8B and 9.

Figure 5A:
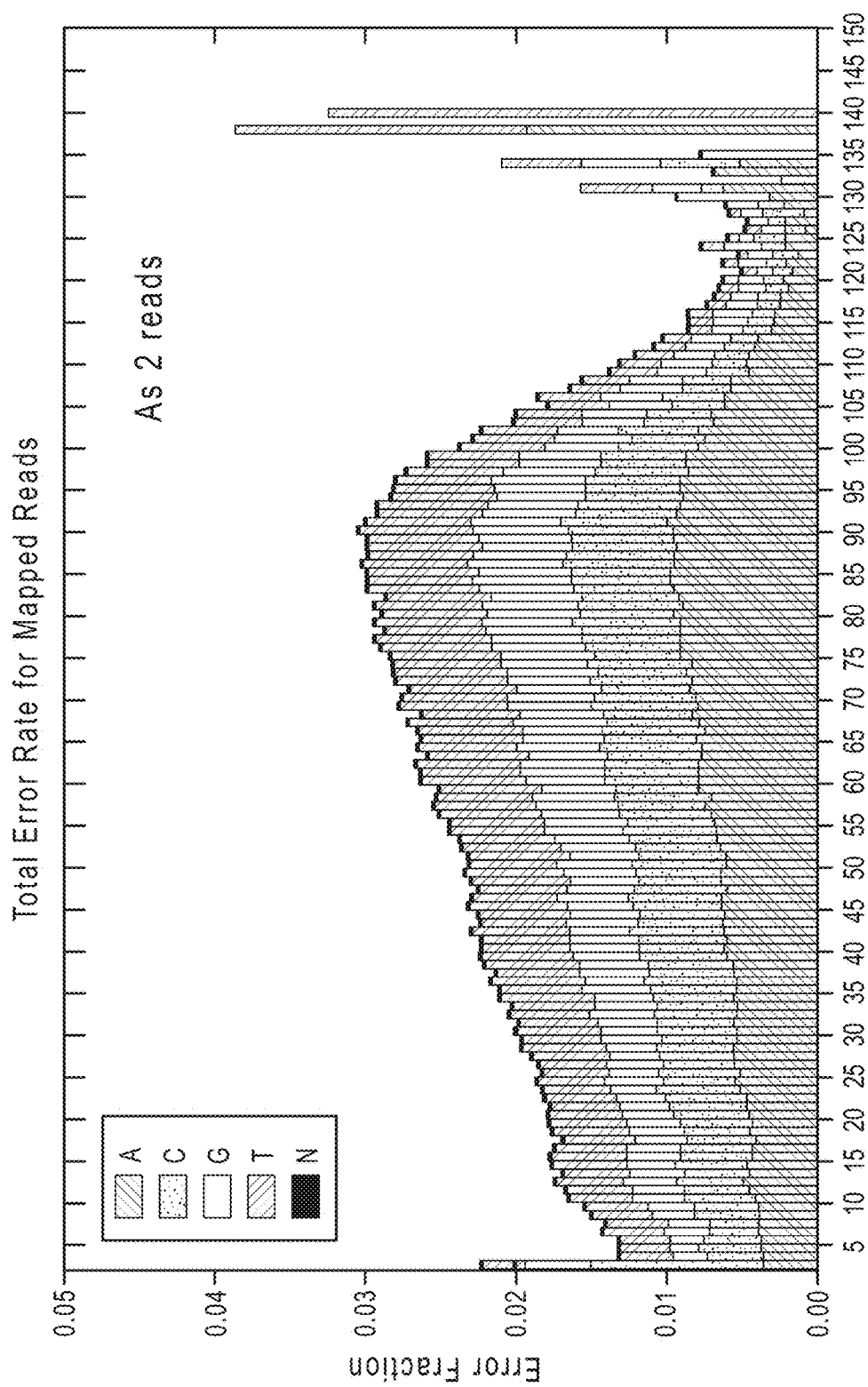
FIG. 5A is a graph disclosing total error rate for dual reads (2 reads) obtained using an exemplary paired-end sequencing method according to the disclosure.
Figure 5B:
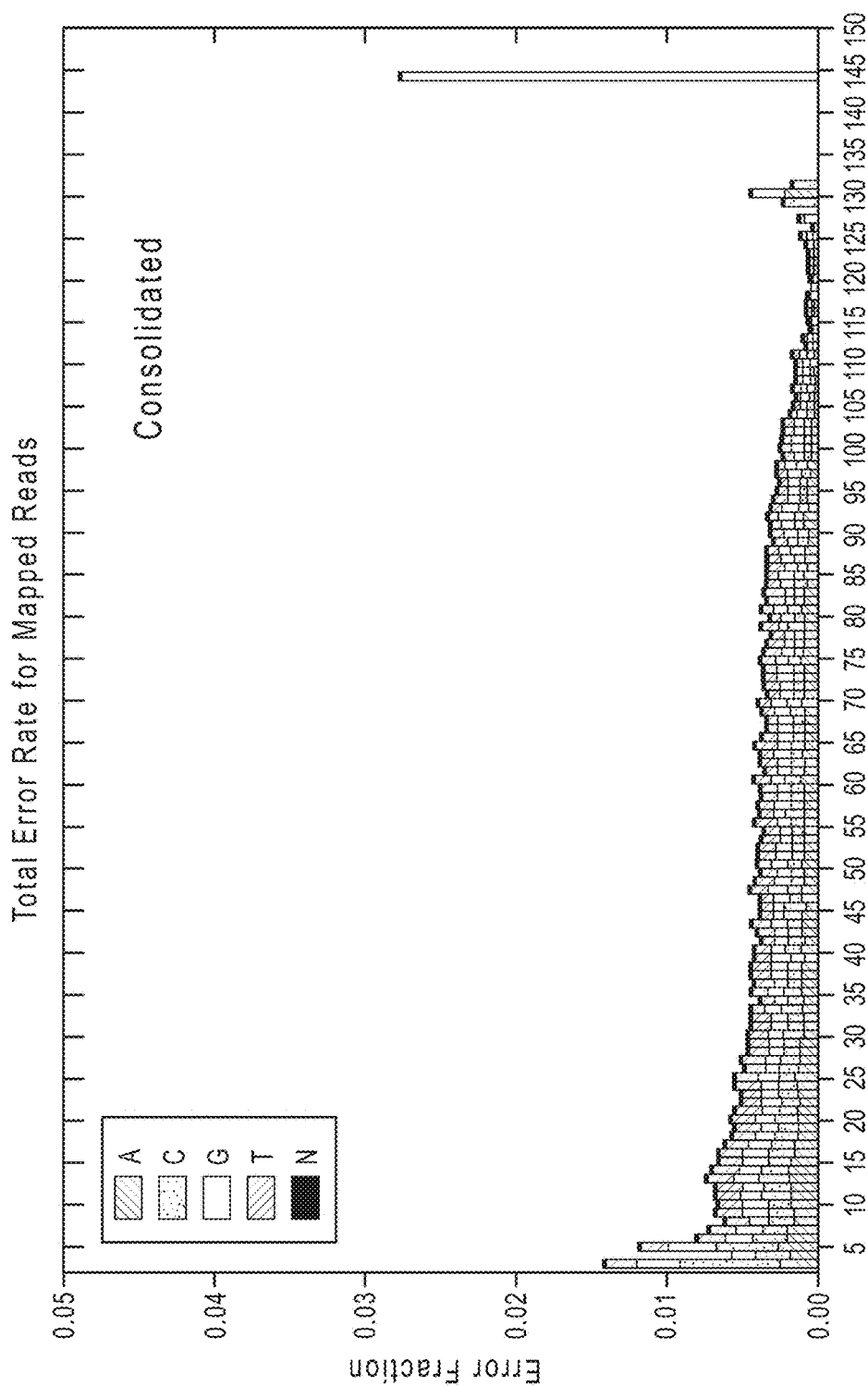
FIG. 5B is a graph disclosing consolidated reads obtained using an exemplary paired-end sequencing method according to the disclosure.

FIGS. 5A and 5B disclose the total error rate for mapped reads of ULT119 and ULT120 (as compared against the reference sample) as either a consolidate read (i.e., paired end sequencing) (FIG. 5B) or as two-reads (FIG. 5A).

Figure 6A:
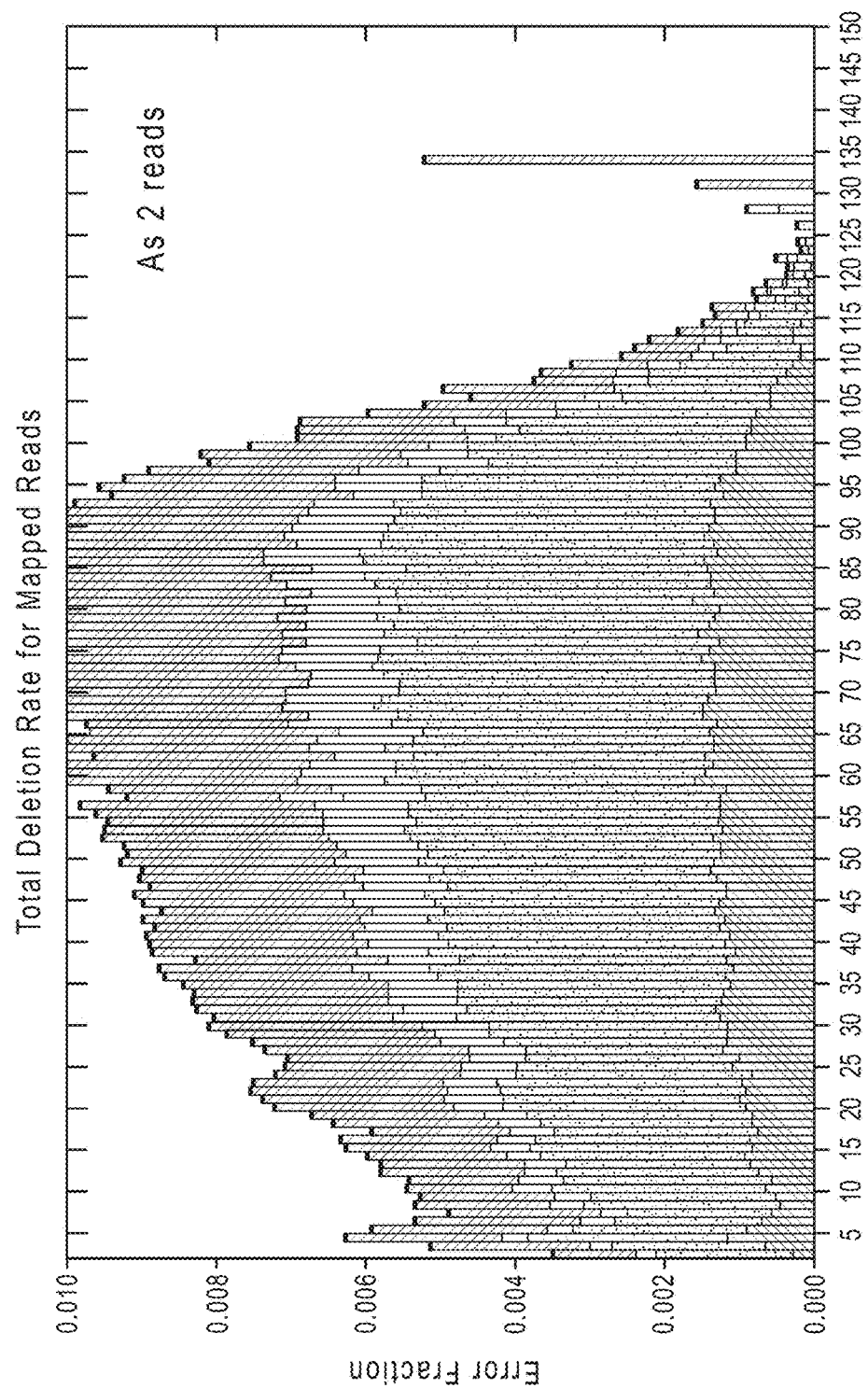
FIG. 6A is a graph disclosing total deletion rate for dual reads (2 reads) obtained using an exemplary paired-end sequencing method according to the disclosure.
Figure 6B:
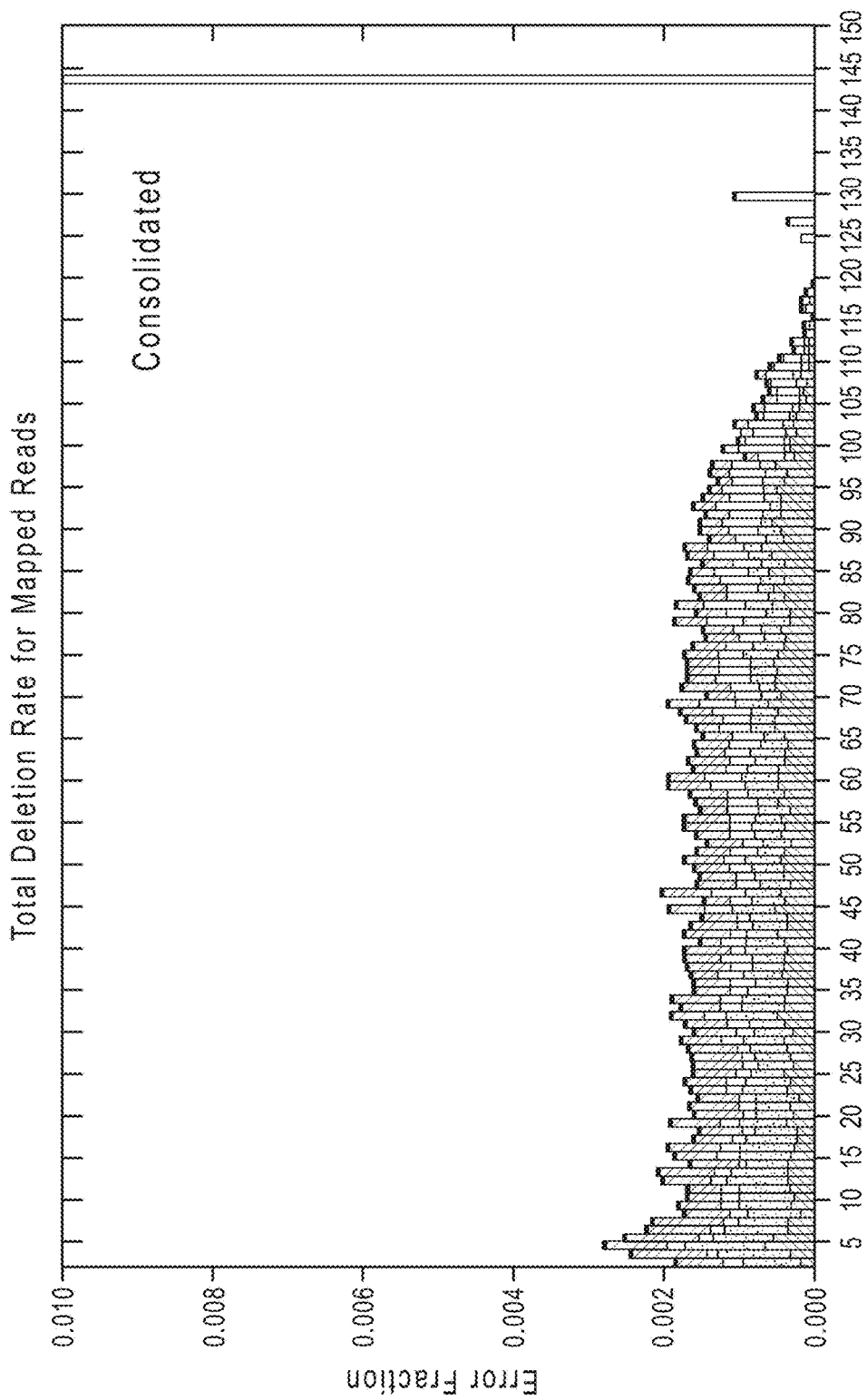
FIG. 6B is a graph disclosing consolidated reads obtained using an exemplary paired-end sequencing method according to the disclosure.

FIGS. 6A and 6B disclose the total deletion rate for mapped reads of ULT119 and ULT120 (as compared against the reference sample) as either a consolidate read (i.e., paired end sequencing) (FIG. 6B) or as two-reads (FIG. 6A).

Figure 7A:
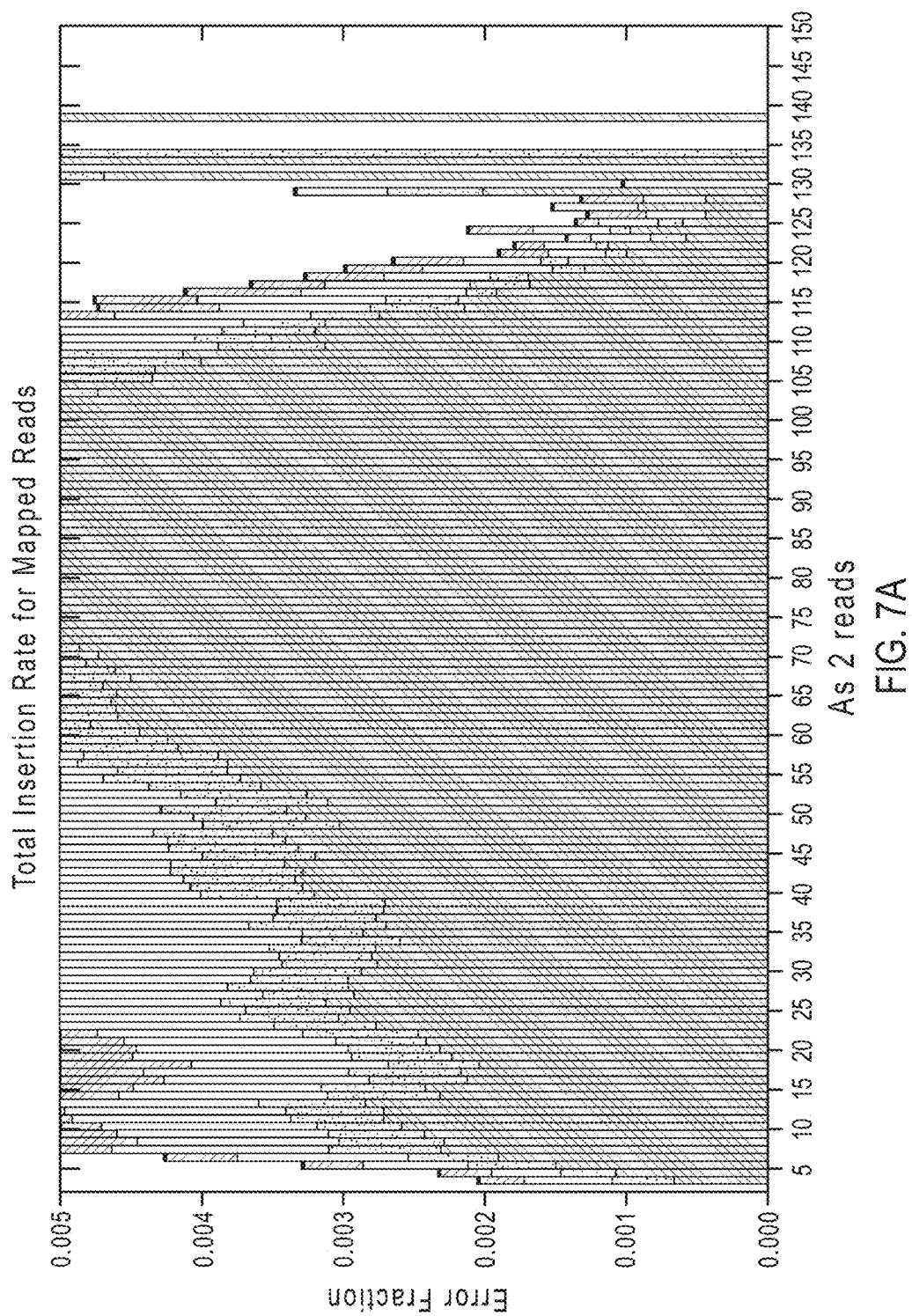
FIG. 7A is a graph disclosing total insertion rate for dual reads (2 reads) obtained using an exemplary paired-end sequencing method according to the disclosure.
Figure 7B:
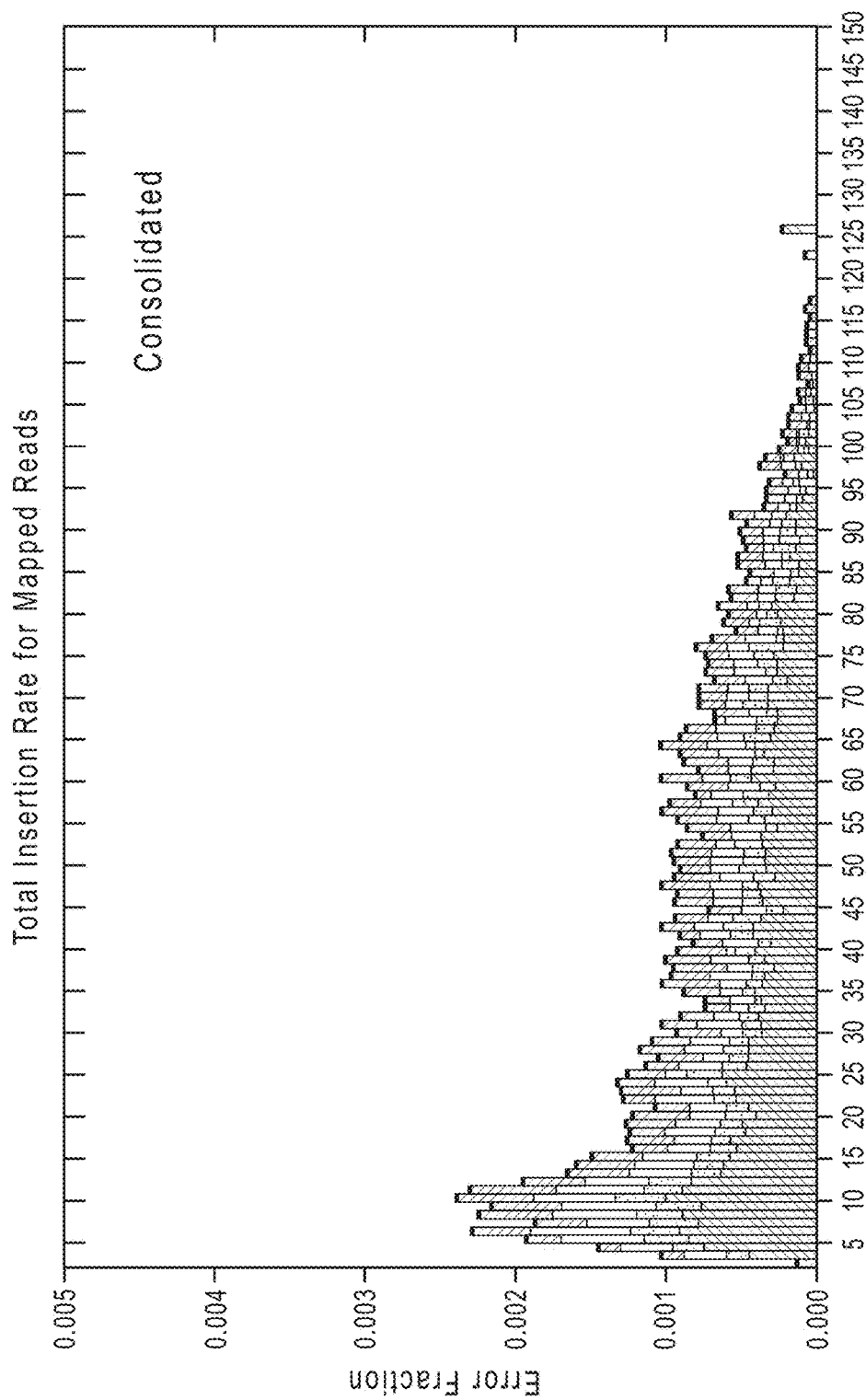
FIG. 7B is a graph disclosing total insertion rate for consolidated reads obtained using an exemplary paired-end sequencing method according to the disclosure.

FIGS. 7A and 7B disclose the total insertion rate for mapped reads of ULT119 and ULT120 (as compared against the reference sample) as either a consolidate read (i.e., paired end sequencing) (FIG. 7B) or as two-reads (FIG. 7A).

Figure 8A:
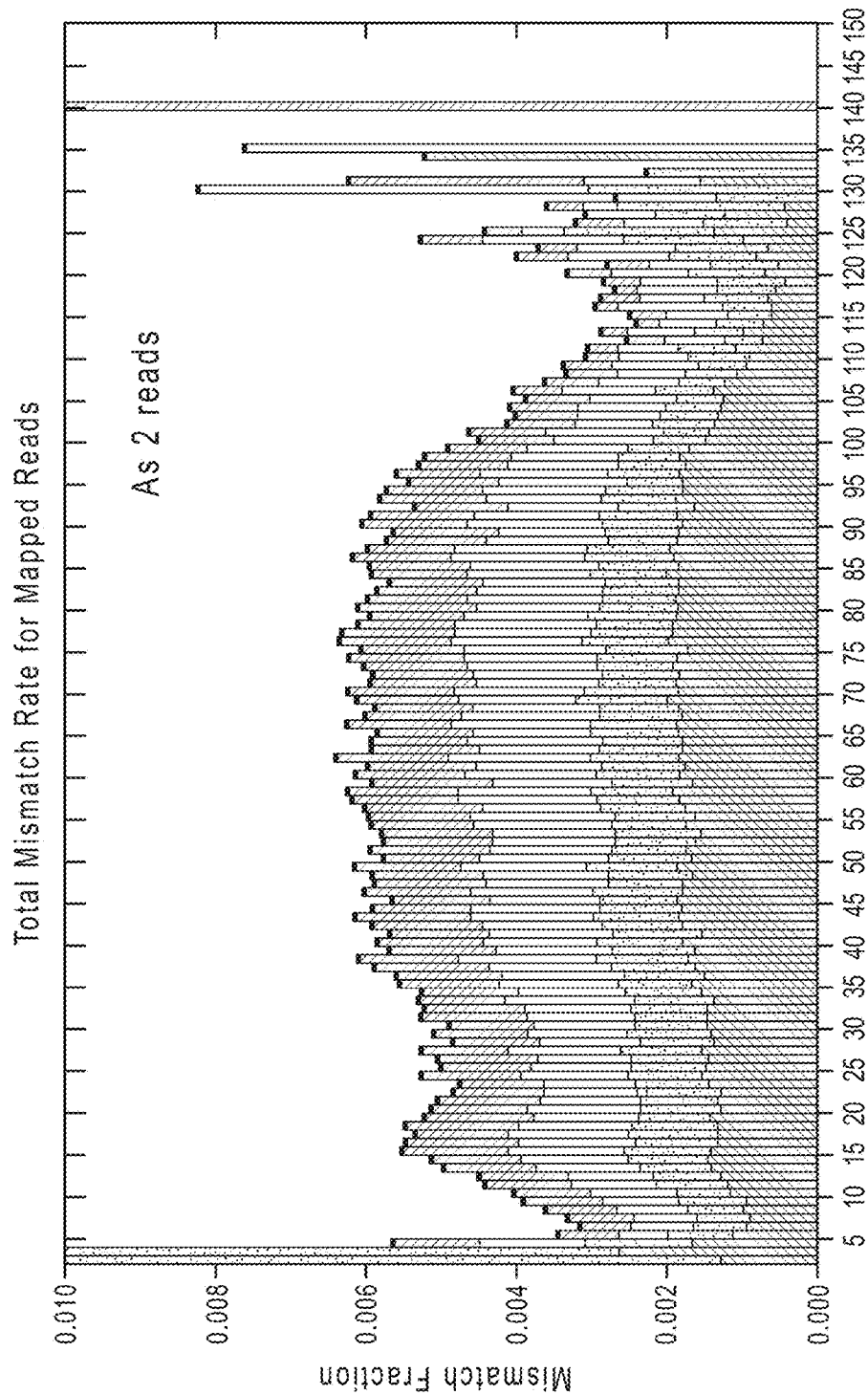
FIG. 8A is a graph disclosing total mismatch rate for dual reads (2 reads) obtained using an exemplary paired-end sequencing method according to the disclosure.
Figure 8B:
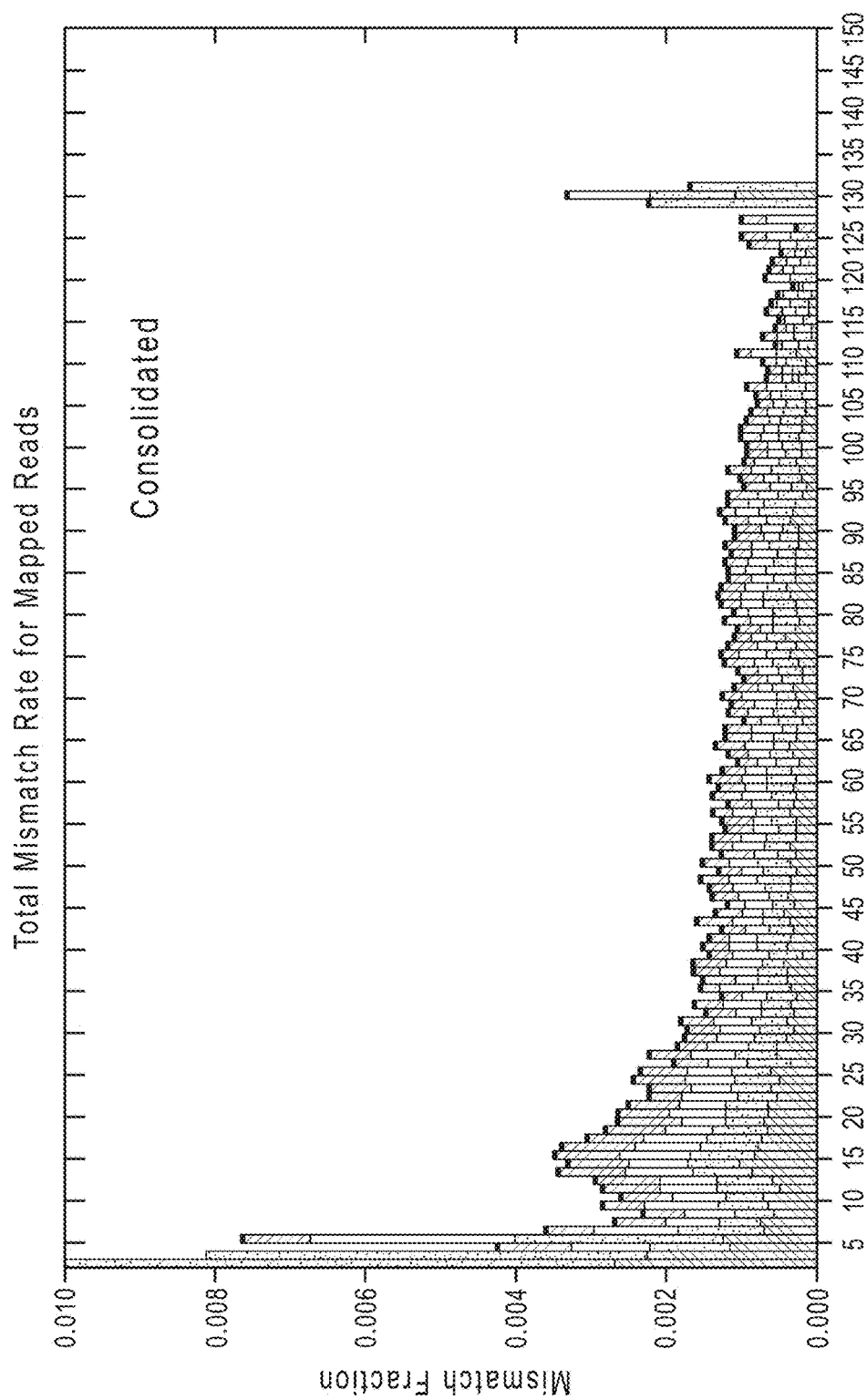
FIG. 8B is a graph disclosing total mismatch rate consolidated reads obtained using an exemplary paired-end sequencing method according to the disclosure.

FIGS. 8A and 8B disclose the total mismatch rate for mapped reads of ULT119 and ULT120 (as compared against the reference sample) as either a consolidate read (i.e., paired end sequencing) (FIG. 8B) or as two-reads (FIG. 8A).

FIG. 9 provides a graphical representation of sequencing data from runs ULT119 and ULT120. As can be seen, improved sequencing accuracy is obtained when consolidating paired-end reads. Therefore, one of the advantages of paired-end sequencing is to increase accuracy by consolidating information from both forward and reverse sequences.

Example 6

The non-limiting, paired-end experiment described below generated two reads for each template on sequencing beads (Ion Sphere Particles™). The steps for determining a pair, consolidating reads, and determining error rates as compared to a reference sequence, were performed as outlined in Example 5.

In this example, a paired-end library was prepared as disclosed in Example 4. Sequencing of forward and reverse reads was performed on a PGM™ Sequencer. The runs performed on the PGM™ sequencer were referred to as: BUT381 and CAR321. Data from the forward and reverse runs is provided in Table 2, below.

TABLE 2

|  | Forward reads | Reverse reads | Total Reads |
|---|---|---|---|
| Run name | BUT381 | CAR321 |  |
| Pairable | 76,619 | 76,619 | 153,238 |

A total of 153,238 reads were obtained. The forward and reverse runs in each pair were consolidated to account of insertions, deletions, mismatches and total errors against a reference DNA sample (here, *E. coli*). Specifically, each paired-end read was consolidated to account for variations against the reference sequence. As a result, the number of consolidated reads for the above experiment was 61,295 reads. The data from the PGM sequencing runs can be found in FIGS. 10A, 10B, 11A, 11B, 12A, 12B, 13A and 13B.

FIGS. 10A and 10B disclose the total error rate for mapped reads of BUT381 and CAR321 (as compared against the reference sample) as either a consolidate read (i.e., paired end sequencing) (FIG. 10B) or as two-reads (FIG. 10A).

FIGS. 11A and 11B disclose the total deletion rate for mapped reads of BUT381 and CAR321 (as compared against the reference sample) as either a consolidate read (i.e., paired end sequencing) (FIG. 11B) or as two-reads (FIG. 11A).

FIGS. 12A and 12B disclose the total insertion rate for mapped reads of BUT381 and CAR321 (as compared against the reference sample) as either a consolidate read (i.e., paired end sequencing) (FIG. 12B) or as two-reads (FIG. 12A).

FIGS. 13A and 13B disclose the total mismatch rate for mapped reads of BUT381 and CAR321 (as compared against the reference sample) as either a consolidate read (i.e., paired end sequencing) (FIG. 13B) or as two-reads (FIG. 13A).

Table 3 provides a summary of both experiments disclosed in Examples 5 and 6. As can be seen, an improved accuracy is obtained when consolidating paired-end reads. Therefore, one advantage of paired-end sequencing is to increase sequencing accuracy by consolidating information from both forward and reverse sequences. Overall, a 3-4 fold increase in sequencing accuracy was observed in these experiments when consolidating paired-end reads.

TABLE 3

|  | As 2 reads | Consolidated | As 2 reads | Consolidated |
|---|---|---|---|---|
| Total Base | 20,372,929 | 10,300,696 | 13,448,227 | 7,240,160 |
| Deletion | 163,472 | 15,988 | 82,084 | 14,178 |
| Insertion | 175,237 | 8,782 | 76,168 | 4,397 |
| Mismatch | 195,984 | 50,544 | 105,428 | 32,176 |
| Total Error | 534,693 | 75,314 | 263,680 | 50,751 |
| Base Accuracy | 97.4% | 99.3% | 98% | 99.3% |

Overall, 3-4 fold increase in accuracy

Example 7

Variant Assessment

In this example, the ability for variant calling after error correction and consolidation was assessed using an exemplary paired end sequencing method according to the disclosure. A total of 6,263 substitutions were simulated into an *E. coli* reference sample (here, a DH10B reference sample). Sequencing runs were performed on a PGM™ sequencer using an Ion Chip, according to Example 4. Once the forward and reverse runs were complete, the runs were consolidated to obtain paired-end information using the simulated substitution *E. coli* sample as the reference sample. The consolidation process of both the forward and reverse runs was performed as described in Examples 5 and 6.

Table 4 provides a summary of the PGM™ run data obtained for UTL119 and UTL120 using the simulated substituted reference sample. Table 5 provides a summary of the PGM™ run data obtained for BUT381 and CAR321 using the simulated substituted reference sample.

As can be seen, the consolidation process in both independent experiments retained the ability for variant calling.

TABLE 4

ULT119 & ULT120

|  | Number of Bases | Percent | Avg Coverage |
|---|---|---|---|
| No Coverage | 1174 |  | 0 |
| Non Ref | 3158 | 62% | 3.08 |
| As Ref | 1931 | 38% | 1.44 |

TABLE 5

BUT381 & CAR321

|  | Number of Bases | Percent | Avg Coverage |
|---|---|---|---|
| No Coverage | 1990 |  | 0 |
| Non Ref | 2283 | 53% | 2.70 |
| As Ref | 1990 | 47% | 1.36 |

Example 8

In this exemplary example, a paired-end library was prepared as follows:

Prepare the Paired-End Adaptor Mixture

Paired-End Adaptor oligonucleotides were created to form a paired-end adapter mixture for use in the library preparation. Paired-end P1 Adaptor oligonucleotide 1 and 2 contain an Nt.BbvCl nick site, while Adaptor A oligonucleotides 1 and 2 complete the adaptors mixture. All oligonucleotides were HPLC purified and subjected to sodium salt exchange.

```
Paired-end P1        5'-CCTCTCTATGGGCAGTCG
Adapter oligo 1      GTGATCCTCAGC-3'
                     SEQ ID NO: 1

Paired-end P1        5'-GCTGAGGATCACCGACTG
Adapter oligo 2      CCCATAGAGAGGTT-3'
                     SEQ ID NO: 3

Adapter A            5'-CCATCTCATCCCTGCGTG
oligo 1              TCTCCGACTCAG-3'
                     SEQ ID NO: 4

Adapter A            5'-CTGAGTCGGAGACACGCA
oligo 2              GGGATGAGATGG*T*T-3'
                     SEQ ID NO: 5
```

The following paired-end sequencing primer was ordered and purified as above.

5'-C*C*A*T*CTCATCCCTGCGTGTCTCCGAC-3', wherein * denotes a phosphorothioate bond. (SEQ ID NO: 6)

Prepare Enzyme Denaturation Solution

An enzyme denaturing solution (EDS) was prepared as follows for use in the paired-end library. 1.3 ml of EDS was used per sequencing reaction: TE pH 8.0; 2% SDS; 50 mM NaCl.

Prepare the Paired-End Adaptors Mixture

Each Adaptor oligonucleotide was diluted to a concentration of 100 um with Y µl of nuclease-free water, determined as follows:

$X$ nmole oligo/100 nmole×1000=$Y$ µl of nuclease-free water

The following reactions were prepared in separate sterile tubes:

|  | Tube 1 | Tube 2 |
| --- | --- | --- |
| Paired-end P1 Adapter oligo 1 (100 µM) | 50 µL | — |
| Paired-end P1 Adapter oligo 2 (100 µM) | 50 µL | — |
| A Adapter oligo 1 (100 µM) | — | 50 µL |
| A Adapter oligo 2 (100 µM) | — | 50 µL |
| T4 DNA Ligase Buffer (5X) | 25 µL | 25 µL |

Each tube was heated using a thermal cycler as follows:
A) Heat at 90° C. for 2 minutes
B) Cool to room temperature (~120 minutes)

Equal volumes of each adaptor were combined into a single tube to form a complete adaptor mixture at a final concentration of about 20 µM. The complete adaptor mixture was then stored at −20° C. until ready to progress to the next step.

Library Preparation: Substitute the Paired-End Adaptors Mixture

A non-barcoded library was prepared as essentially described in the Ion Xpress™ Plus gDNA and Amplicon Library Preparation User Guide (Life Technologies, Part No. 4471989), except the standard adaptors of the Ion Xpress™ Plus Library Kit were substituted with the adaptor mixture prepared above. The library was prepared essentially according to the protocol outlined in the above Library Preparation User Guide, which is incorporated herein in its entirety.

Perform Standard Forward Sequencing

A standard sequencing protocol was performed as essentially described in the Ion Sequencing 200 Kit User Guide (Life Technologies, Part No. 4471998), which is incorporated herein in its entirety, except that the standard sequencing primer was substituted for the paired-end sequencing primer, prepared above. The paired-end sequencing primer was added to the Ion Sphere Particles (ISPs) as follows:

|  | Volume per chip | |
| --- | --- | --- |
| Component | Ion 314 ™ Chip | Ion 316 ™ Chip |
| Paired-end Sequencing Primer | 5 µL | 12 µL |
| Enriched ISPs in Annealing Buffer | 8 µL | 15 µL |
| Total volume | 13 µL | 27 µL |

The standard sequencing protocol was then performed as essentially outlined in the Sequencing Kit User Guide.

Denature the Sequencing Polymerase

After the sequencing run was complete, the Ion chip was removed from the PGM™ System and placed on a grounding plate or in an Ion centrifuge adapter/rotor bucket. While the Ion chip was removed, a dummy (used) chip was clamped into the PGM.

100 µL of EDS was applied into the loading port on the Ion chip. The Chip was then incubated at room temperature for 1 minute. After incubation, the chip was washed three times with 100 µL of EDS: for each wash, 100 µL of EDS was added to the loading port and then removed.

A 1× NEBuffer 2 was prepared by diluting the stock buffer 1:10 with nuclease-free water. The chip was then washed three times with 100 µL of 1× NEBuffer 2.

Fill in the Sequence

An extension solution was prepared as follows:

|  | Volume per chip | |
| --- | --- | --- |
| Component | Ion 314 ™ Chip | Ion 316 ™ Chip |
| Nuclease-free water | 14 µL | 56 µL |
| 10 mM dNTPs (prepare a 1:4 dilution of stock dNTPs from the Ion Xpress ™ Template 200 Kit) | 2 µL | 8 µL |
| 10X NEBuffer 2 | 2 µL | 8 µL |
| DNA Polymerase I, Large (Klenow) Fragment | 2 µL | 2 µL |
| Total | 20 µL | 80 µL |

The following volumes of extension solution were applied to the loading port of the respective chip.
Ion 314™ Chip: 15 µl (~5 µl overflow in flow cell wells)
Ion 316™ Chip: 75 µl (~25 µl overflow in flow cell wells)

The chip was then transferred to a covered heating block (at 25° C.) containing a 50 ml tube cap filled with deionized water (to prevent evaporation) and incubated for 10 minutes. After which, 100 ul of EDS was loaded into the loading port, and incubated at room temperature for 1 minute. After incubation, as much liquid as possible was removed from the loading port. The chip was then washed 3 times with 100 µl of EDS. A 1× NEBuffer 4 was prepared by diluting the stock buffer 1:10 with nuclease-free water. The chip was then washed three times with 100 µL of 1× NEBuffer 4.

Denature the Template

A second strand solution was prepared as outlined below.

|  | Volume per chip | |
| --- | --- | --- |
| Component | Ion 314 ™ Chip | Ion 316 ™ Chip |
| Nuclease-free water | 42 µL | 168 µL |
| NEBuffer 4 (1x) | 6 µL | 24 µL |
| Nt.BbvCl | 6 µL | 24 µL |
| T7 Exonuclease | 6 µL | 24 µL |
| Total | 60 µL | 240 µL |

The following amounts of the second strand solution was dispensed into the respective Chip.
Ion 314™ Chip: 15 µl (~5 µl overflow in flow cell wells)
Ion 316™ Chip: 75 µl (~25 µl overflow in flow cell wells)

The chip was placed on a 1.5 ml freezer rack half filled with deionized water and incubated at room temperature for 20 minutes. The fluid in the chip was replaced from the loading port, and the second strand solution was re-applied to the chip for a second and third time, with the respective incubation times for a total incubation time of 60 minutes. After the final incubation, residual liquid was removed from the chip and 100 µl of EDs was applied to the loading port. The chip was incubated at room temperature for 1 minute, after which the EDS solution was removed from the chip. The chip was subsequently washed 3 times with 100 µl of EDS.

The chip was then washed 3 times with 100 µl of annealing buffer from the Ion Sequencing 200 Kit.

The sequencing polymerase from the Ion Sequencing 200 Kit was diluted in annealing buffer as shown below:

| Component | Volume per chip | |
| --- | --- | --- |
| | Ion 314 ™ Chip | Ion 316 ™ Chip |
| Sequencing Polymerase | 1.5 μL | 6 μL |
| Annealing Buffer | 6 μL | 24 μL |
| Total volume | 7.5 μL | 30 μL |

Any residual annealing buffer from the wash steps was removed from the chip, and the diluted sequencing polymerase was applied (in full volume) to the loading port and incubated at room temperature for 5 minutes. During incubation, the sequencing key for the PGM system was altered as shown below:

A) From the main screen, press Options.
B) Press Advanced.
C) Press Change "Library Key Sequence".
D) Enter the new key sequence: TCAGC.
E) Press Back to return to the main screen.

Following incubation, the dummy (used) chip was removed from the PGM system and the prepared paired-end sequencing chip was loaded. The sequencing experiment was initiated via pressing "experiment" on the PGM system. During the chip check, the "wetload" box was unchecked. The chip washing and loading steps provided in the Ion Sequencing 200 Kit were also obviated to proceed directly to selecting the experimental configuration and performance of the sequencing run.

Example 9

In this exemplary embodiment, a paired-end library was prepared as follows:

Prepare the Paired-End Adaptor Mixture

Paired-End Adaptor oligonucleotides were created to form a paired-end adapter mixture for use in the library preparation. Paired-end P1 Adaptor oligonucleotide 3 and 4 contain an Nt.BbvCI nick site, while Adaptor A oligonucleotides 3 and 4 complete the adaptors mixture. All oligonucleotides were HPLC purified and subjected to sodium salt exchange. In the oligonucleotides * denotes a phosphorothioate bond. In the oligonucleotides "Y" denotes a C or a T nucleotide at that position.

```
Paired-end P1     5'-CCACTACGCCTCCGCTTT
Adapter oligo 3   CCTCTCTATGGGCAGTCGGTG
                  ATCCTCAGC-3'
                  SEQ ID NO: 7

Paired-end P1     5'-GCTGAGGATCACCGACTG
Adapter oligo 4   CCCATAGAGAGGAAAGCGGAG
                  GCGTAGYGG*T*T-3'
                  SEQ ID NO: 8

Adapter A         5'-CCATCTCATCCCTGCGTG
oligo 3           TCTCCGACTCAG-3'
                  SEQ ID NO: 4
```

```
Adapter A         5'-CTGAGTCGGAGACACGCA
oligo 4           GGGATGAGATGG*T*T-3'
                  SEQ ID NO: 5
```

The following paired-end sequencing primer was ordered and purified as above.
5'-C*C*A*T*CTCATCCCTGCGTGTCTCCGAC-3' (SEQ ID NO: 6), wherein * denotes a phosphorothioate bond.

Prepare Enzyme Denaturation Solution

An enzyme denaturing solution (EDS) was prepared as follows for use in the paired-end library: 10×TE pH 8.0 (5 ml), 20% SDS (5 ml) and 50 mM NaCl (0.5 ml) to a total of 50 ml in nuclease-free water. Final concentration: 1×TE pH 8.0, 2% SDS and 50 mM NaCl. 1.3 ml of EDS was used per sequencing reaction.

Prepare the Paired-End Adaptors Mixture

Each Adaptor oligonucleotide was diluted to a concentration of 100 um with Y μl of nuclease-free water, determined as follows:

$X$ nmole oligo/100 nmole×1000=$Y$ μl of nuclease-free water

The following reactions were prepared in separate sterile tubes:

| | Tube 1 | Tube 2 |
| --- | --- | --- |
| Paired-end P1 Adapter oligo 3 (100 μM) | 50 μL | — |
| Paired-end P1 Adapter oligo 4 (100 μM) | 50 μL | — |
| A Adapter oligo 3 (100 μM) | — | 50 μL |
| A Adapter oligo 4 (100 μM) | — | 50 μL |
| T4 DNA Ligase Buffer (5X) | 25 μL | 25 μL |

Each tube was heated using a thermal cycler as follows:
A) Heat at 90° C. for 2 minutes
B) Cool to room temperature (~120 minutes)

Equal volumes of each adaptor were combined into a single tube to form a complete adaptor mixture at a final concentration of about 20 μM. The complete adaptor mixture was then stored at −20° C. until ready to progress to the next step.

Library Preparation: Substitute the Paired-End Adaptors Mixture

A non-barcoded library was prepared as essentially described in the Ion Plus Fragment Library Kit (Life Technologies, Part No. 4471252), except the standard adaptors of the Ion Plus Fragment Library Kit were substituted with the adaptor mixture prepared above. The library was prepared essentially according to the protocol outlined in the above Library Preparation User Guide, which is incorporated herein in its entirety.

Template Preparation

A standard template protocol was performed as essentially described in the Ion Template Kit User Guide (Life Technologies, Part No. 4469004), which is incorporated herein in its entirety.

Perform Standard Forward Sequencing

A standard sequencing protocol was performed as essentially described in the Ion Sequencing 200 Kit User Guide (Life Technologies, Part No. 4471998), which is incorporated herein in its entirety, except that the standard sequencing primer was substituted for the paired-end sequencing primer, prepared above. The paired-end sequencing primer was added to the Ion Sphere Particles (ISPs) as follows:

| Component | Volume per chip | |
|---|---|---|
| | Ion 314™ Chip | Ion 316™ Chip |
| Paired-end Sequencing Primer | 5 µL | 12 µL |
| Enriched ISPs in Annealing Buffer | 8 µL | 15 µL |
| Total volume | 13 µL | 27 µL |

The standard sequencing protocol was then performed as essentially outlined in the Sequencing Kit User Guide.

Denature the Sequencing Polymerase

After the sequencing run was complete, the Ion chip was removed from the PGM™ System and placed on a grounding plate or in an Ion centrifuge adapter/rotor bucket. While the Ion chip was removed, a dummy (used) chip was clamped into the PGM.

100 µL of EDS was applied into the loading port on the Ion chip. The Chip was then incubated at room temperature for 1 minute. After incubation, the chip was washed once with 100 µL of EDS; the EDS was added to the loading port and then removed.

A 1× NEBuffer 2 was prepared by diluting the stock buffer 1:10 with nuclease-free water. The chip was then washed three times with 100 µL of 1× NEBuffer 2.

Fill in the Sequence

An extension solution was prepared as follows:

| Component | Volume per chip | |
|---|---|---|
| | Ion 314™ Chip | Ion 316™ Chip |
| Nuclease-free water | 14 µL | 56 µL |
| 10 mM dNTPs (prepare a 1:4 dilution of stock dNTPs from the Ion Xpress™ Template 200 Kit) | 2 µL | 8 µL |
| 10X NEBuffer 2 | 2 µL | 8 µL |
| DNA Polymerase I, Large (Klenow) Fragment | 2 µL | 2 µL |
| Total | 20 µL | 80 µL |

The following volumes of extension solution were applied to the loading port of the respective chip.

Ion 314™ Chip: 15 µl (~5 µl overflow in flow cell wells)
Ion 316™ Chip: 75 µl (~25 µl overflow in flow cell wells)

The chip was then transferred to a covered heating block (at 25° C.) containing a 50 ml tube cap filled with deionized water (to prevent evaporation) and incubated for 10 minutes. After which, 100 ul of EDS was loaded into the loading port, and incubated at room temperature for 1 minute. After incubation, as much liquid as possible was removed from the loading port. A 1× NEBuffer 4 was prepared by diluting the stock buffer 1:10 with nuclease-free water. The chip was then washed three times with 100 µL of 1× NEBuffer 4.

Denature the Template

A second strand solution was prepared as outlined below.

| Component | Volume per chip | |
|---|---|---|
| | Ion 314™ Chip | Ion 316™ Chip |
| Nuclease-free water | 42 µL | 168 µL |
| NEBuffer 4 (1x) | 6 µL | 24 µL |

-continued

| Component | Volume per chip | |
|---|---|---|
| | Ion 314™ Chip | Ion 316™ Chip |
| Nt.BbvCI | 6 µL | 24 µL |
| T7 Exonuclease | 6 µL | 24 µL |
| Total | 60 µL | 240 µL |

The following amounts of the second strand solution was dispensed into the respective Chip.

Ion 314™ Chip: 15 µl (~5 µl overflow in flow cell wells)
Ion 316™ Chip: 75 µl (~25 µl overflow in flow cell wells)

The chip was placed on a 1.5 ml freezer rack half filled with deionized water and incubated at room temperature for 20 minutes. The fluid in the chip was replaced from the loading port, and the second strand solution was re-applied to the chip for a second and third time, with the respective incubation times for a total incubation time of 60 minutes. After the final incubation, residual liquid was removed from the chip and 100 µl of EDS was applied to the loading port. The chip was then washed 3 times with 100 µl of annealing buffer from the Ion Sequencing 200 Kit.

The sequencing polymerase from the Ion Sequencing 200 Kit was diluted in annealing buffer as shown below:

| Component | Volume per chip | |
|---|---|---|
| | Ion 314™ Chip | Ion 316™ Chip |
| Sequencing Polymerase | 1.5 µL | 6 µL |
| Annealing Buffer | 6 µL | 24 µL |
| Total volume | 7.5 µL | 30 µL |

Any residual annealing buffer from the wash steps was removed from the chip, and the diluted sequencing polymerase was applied (in full volume) to the loading port and incubated at room temperature for 5 minutes. During incubation, the sequencing key for the PGM system was altered as shown below:

F) From the main screen, press Options.
G) Press Advanced.
H) Press Change "Library Key Sequence".
I) Enter the new key sequence: TCAGC.
J) Press Back to return to the main screen.

Following incubation, the dummy (used) chip was removed from the PGM system and the prepared paired-end sequencing chip was loaded. The sequencing experiment was initiated via pressing "experiment" on the PGM system. During the chip check, the "wetload" box was unchecked. The chip washing and loading steps provided in the Ion Sequencing 200 Kit were also obviated to proceed directly to selecting the experimental configuration and performance of the sequencing run.

Example 10

In this non-limiting example, a paired-end library was prepared as follows:

Prepare the Paired-End Adaptor Mixture

Paired-End Adaptor oligonucleotides were created to form a paired-end adapter mixture for use in the library preparation. Paired-end P1 Adaptor oligonucleotide 3 and 4 contain an Nt.BbvCI nick site, while Adaptor A oligonucleotides 3 and 4 complete the adaptors mixture. All oligonucleotides were HPLC purified and subjected to sodium salt exchange. In the oligonucleotides "Y" denotes a C or a T nucleotide at that position.

| Paired-end P1 Adapter oligo 3 | 5'-CCACTACGCCTCCGCTTT CCTCTCTATGGGCAGTCGGTG ATCCTCAGC-3' SEQ ID NO: 7 |
|---|---|
| Paired-end P1 Adapter oligo 4 | 5'-GCTGAGGATCACCGACTG CCCATAGAGAGGAAAGCGGAG GCGTAGYGG*T*T-3' SEQ ID NO: 8 |
| Adapter A oligo 3 | 5'-CCATCTCATCCCTGCGTG TCTCCGACTCAG-3' SEQ ID NO: 4 |
| Adapter A oligo 4 | 5'-CTGAGTCGGAGACACGCA GGGATGAGATGG*T*T-3' SEQ ID NO: 5 |

The following paired-end sequencing primer was ordered and purified as above.

5'-C*C*A*T*CTCATCCCTGCGTGTCTCCGAC-3' (SEQ ID NO: 6), wherein * denotes a phosphorothioate bond. In the oligonucleotides * denotes a phosphorothioate bond.

Prepare Enzyme Denaturation Solution

An enzyme denaturing solution (EDS) was prepared as follows for use in the paired-end library: 10×TE pH 8.0 (5 ml), 20% SDS (5 ml) and 50 mM NaCl (0.5 ml) to a total of 50 ml in nuclease-free water. Final concentration: 1×TE pH 8.0, 2% SDS and 50 mM NaCl. 1.3 ml of EDS was used per sequencing reaction.

Prepare the Paired-End Adaptors Mixture

Each Adaptor oligonucleotide was diluted to a concentration of 100 um with Y μl of nuclease-free water, determined as follows:

$X$ nmole oligo/100 nmole×1000=$Y$ μl of nuclease-free water

The following reactions were prepared in separate sterile tubes:

|  | Tube 1 | Tube 2 |
|---|---|---|
| Paired-end P1 Adapter oligo 3 (100 μM) | 50 μL | — |
| Paired-end P1 Adapter oligo 4 (100 μM) | 50 μL | — |
| A Adapter oligo 3 (100 μM) | — | 50 μL |
| A Adapter oligo 4 (100 μM) | — | 50 μL |
| T4 DNA Ligase Buffer (5X) | 25 μL | 25 μL |

Each tube was heated using a thermal cycler as follows:
A) Heat at 90° C. for 2 minutes
B) Cool to room temperature (~120 minutes)

Equal volumes of each adaptor were combined into a single tube to form a complete adaptor mixture at a final concentration of about 20 μM. The complete adaptor mixture was then stored at −20° C. until ready to progress to the next step.

Library Preparation: Substitute the Paired-End Adaptors Mixture

A non-barcoded library was prepared as essentially described in the Ion Plus Fragment Library Kit (Life Technologies, Part No. 4471252), except the standard adaptors of the Ion Plus Fragment Library Kit were substituted with the adaptor mixture prepared above. The library was prepared essentially according to the protocol outlined in the above Library Preparation User Guide, which is incorporated herein in its entirety.

Template Preparation

A standard template protocol was performed as essentially described in the Ion Template Kit User Guide (Life Technologies, Part No. 4469004), which is incorporated herein in its entirety.

Perform Standard Forward Sequencing

A standard sequencing protocol was performed as essentially described in the Ion Sequencing 200 Kit User Guide (Life Technologies, Part No. 4471998), which is incorporated herein in its entirety, except that the standard sequencing primer was substituted for the paired-end sequencing primer, prepared above. The paired-end sequencing primer was added to the Ion Sphere Particles (ISPs) as follows:

|  | Volume per chip | |
|---|---|---|
| Component | Ion 314 ™ Chip | Ion 316 ™ Chip |
| Paired-end Sequencing Primer | 5 μL | 12 μL |
| Enriched ISPs in Annealing Buffer | 8 μL | 15 μL |
| Total volume | 13 μL | 27 μL |

The standard sequencing protocol was then performed as essentially outlined in the Sequencing Kit User Guide.

Denature the Sequencing Polymerase

After the sequencing run was complete, the Ion chip was removed from the PGM™ System and placed on a grounding plate or in an Ion centrifuge adapter/rotor bucket. While the Ion chip was removed, a dummy (used) chip was clamped into the PGM.

100 μL of EDS was applied into the loading port on the Ion chip. The Chip was then incubated at room temperature for 1 minute.

A 1× NEBuffer 2 was prepared by diluting the stock buffer 1:10 with nuclease-free water. The chip was then washed three times with 100 μL of 1× NEBuffer 2.

Fill in the Sequence

An extension solution was prepared as follows:

|  | Volume per chip | |
|---|---|---|
| Component | Ion 314 ™ Chip | Ion 316 ™ Chip |
| Nuclease-free water | 14 μL | 56 μL |
| 10 mM dNTPs (prepare a 1:4 dilution of stock dNTPs from the Ion Xpress ™ Template 200 Kit) | 2 μL | 8 μL |
| 10X NEBuffer 2 | 2 μL | 8 μL |
| DNA Polymerase I, Large (Klenow) Fragment | 2 μL | 2 μL |
| Total | 20 μL | 80 μL |

The following volumes of extension solution were applied to the loading port of the respective chip.

Ion 314™ Chip: 15 μl (~5 μl overflow in flow cell wells)
Ion 316™ Chip: 75 μl (~25 μl overflow in flow cell wells)

The chip was then transferred to a covered heating block (at 25° C.) containing a 50 ml tube cap filled with deionized water (to prevent evaporation) and incubated for 10 minutes. After which, 100 ul of EDS was loaded into the loading port, and incubated at room temperature for 1 minute. After incubation, as much liquid as possible was removed from the loading port. A 1× NEBuffer 4 was prepared by diluting the stock buffer 1:10 with nuclease-free water. The chip was then washed three times with 100 μL of 1× NEBuffer 4.

Denature the Template

A second strand solution was prepared as outlined below.

|  | Volume per chip | |
| --- | --- | --- |
| Component | Ion 314 ™ Chip | Ion 316 ™ Chip |
| Nuclease-free water | 42 μL | 168 μL |
| NEBuffer 4 (1x) | 6 μL | 24 μL |
| Nt.BbvCI | 6 μL | 24 μL |
| T7 Exonuclease | 6 μL | 24 μL |
| Total | 60 μL | 240 μL |

The following amounts of the second strand solution was dispensed into the respective Chip.

Ion 314™ Chip: 15 μl (~5 μl overflow in flow cell wells)
Ion 316™ Chip: 75 μl (~25 μl overflow in flow cell wells)

The chip was placed on a 1.5 ml freezer rack half filled with deionized water and incubated at room temperature for 20 minutes. The fluid in the chip was replaced from the loading port, and the second strand solution was re-applied to the chip for a second and third time, with the respective incubation times for a total incubation time of 60 minutes. After the final incubation, residual liquid was removed from the chip and 100 μl of EDS was applied to the loading port. The chip was incubated at room temperature for 1 minute, after which the EDS solution was removed from the chip.

The chip was then washed 3 times with 100 μl of annealing buffer from the Ion Sequencing 200 Kit.

The sequencing polymerase from the Ion Sequencing 200 Kit was diluted in annealing buffer as shown below:

|  | Volume per chip | |
| --- | --- | --- |
| Component | Ion 314 ™ Chip | Ion 316 ™ Chip |
| Sequencing Polymerase | 1.5 μL | 6 μL |
| Annealing Buffer | 6 μL | 24 μL |
| Total volume | 7.5 μL | 30 μL |

Any residual annealing buffer from the wash steps was removed from the chip, and the diluted sequencing polymerase was applied (in full volume) to the loading port and incubated at room temperature for 5 minutes. During incubation, the sequencing key for the PGM system was altered as shown below:

K) From the main screen, press Options.
L) Press Advanced.
M) Press Change "Library Key Sequence".
N) Enter the new key sequence: TCAGC.
O) Press Back to return to the main screen.

Following incubation, the dummy (used) chip was removed from the PGM system and the prepared paired-end sequencing chip was loaded. The sequencing experiment was initiated via pressing "experiment" on the PGM system. During the chip check, the "wetload" box was unchecked. The chip washing and loading steps provided in the Ion Sequencing 200 Kit were also obviated to proceed directly to selecting the experimental configuration and performance of the sequencing run.

Example 11

In this non-limiting example, a paired-end library was prepared as follows.

Prepare the Paired-End Adaptor Mixture

Paired-End Adaptor oligonucleotides were created to form a paired-end adapter mixture for use in the library preparation. Paired-end P1 Adaptor oligonucleotide 3 and 4 contain an Nt.BbvCl nick site, while Adaptor A oligonucleotides 3 and 4 complete the adaptors mixture. All oligonucleotides were HPLC purified and subjected to sodium salt exchange. In the oligonucleotides * denotes a phosphorothioate bond. In the oligonucleotides "Y" denotes a C or a T nucleotide at that position.

| Paired-end P1 Adapter oligo 3 | 5'-CCACTACGCCTCCGCTTT CCTCTCTATGGGCAGTCGGTG ATCCTCAGC-3' SEQ ID NO: 7 |
| --- | --- |
| Paired-end P1 Adapter oligo 4 | 5'-GCTGAGGATCACCGACTG CCCATAGAGAGGAAAGCGGAG GCGTAGYGG*T*T-3' SEQ ID NO: 8 |
| Adapter A oligo 3 | 5'-CCATCTCATCCCTGCGTG TCTCCGACTCAG-3' SEQ ID NO: 4 |
| Adapter A oligo 4 | 5'-CTGAGTCGGAGACACGCA GGGATGAGATGG*T*T-3' SEQ ID NO: 5 |

The following paired-end sequencing primer was ordered and purified as above.

5'-C*C*A*T*CTCATCCCTGCGTGTCTCCGAC-3' (SEQ ID NO: 6), wherein * denotes a phosphorothioate bond.

Prepare Enzyme Denaturation Solution

An enzyme denaturing solution (EDS) was prepared as follows for use in the paired-end library: 10×TE pH 8.0 (5 ml), 20% SDS (5 ml) and 50 mM NaCl (0.5 ml) to a total of 50 ml in nuclease-free water. Final concentration: 1×TE pH 8.0, 2% SDS and 50 mM NaCl. 1.3 ml of EDS was used per sequencing reaction.

Prepare Additive Solution

A 4% or 8% polyvinylpyrrolidone solution (PVP) was prepared as follows for use in the paired-end library. Dissolve 0.4 grams of PVP40 into 4.8 ml of nuclease-free water to a total volume of 5 ml (8% solution) or dissolve 0.2 grams of PVP40 into 4.8 ml of nuclease-free water to a total volume of 5 ml (4% solution).

Prepare the Paired-End Adaptors Mixture

Each Adaptor oligonucleotide was diluted to a concentration of 100 um with Y μl of nuclease-free water, determined as follows:

$X$ nmole oligo/100 nmole×1000=$Y$ μl of nuclease-free water

The following reactions were prepared in separate sterile tubes:

|  | Tube 1 | Tube 2 |
| --- | --- | --- |
| Paired-end P1 Adapter oligo 3 (100 μM) | 50 μL | — |
| Paired-end P1 Adapter oligo 4 (100 μM) | 50 μL | — |

|  | Tube 1 | Tube 2 |
| --- | --- | --- |
| A Adapter oligo 3 (100 μM) | — | 50 μL |
| A Adapter oligo 4 (100 μM) | — | 50 μL |
| T4 DNA Ligase Buffer (5X) | 25 μL | 25 μL |

Each tube was heated using a thermal cycler as follows:

A) Heat at 90° C. for 2 minutes

B) Cool to room temperature (~120 minutes)

Equal volumes of each adaptor were combined into a single tube to form a complete adaptor mixture at a final concentration of about 20 μM. The complete adaptor mixture was then stored at −20° C. until ready to progress to the next step.

Library Preparation: Substitute the Paired-End Adaptors Mixture

A non-barcoded library was prepared as essentially described in the Ion Plus Fragment Library Kit (Life Technologies, Part No. 4471252), except the standard adaptors of the Ion Plus Fragment Library Kit were substituted with the adaptor mixture prepared above. The library was prepared essentially according to the protocol outlined in the above Library Preparation User Guide, which is incorporated herein in its entirety.

Template Preparation

A standard template protocol was performed as essentially described in the Ion Template Kit User Guide (Life Technologies, Part No. 4469004), which is incorporated herein in its entirety.

Perform Standard Forward Sequencing

A standard sequencing protocol was performed as essentially described in the Ion Sequencing 200 Kit User Guide (Life Technologies, Part No. 4471998), which is incorporated herein in its entirety, except that the standard sequencing primer was substituted for the paired-end sequencing primer, prepared above. The paired-end sequencing primer was added to the Ion Sphere Particles (ISPs) as follows:

|  | Volume per chip | |
| --- | --- | --- |
| Component | Ion 314™ Chip | Ion 316™ Chip |
| Paired-end Sequencing Primer | 5 μL | 12 μL |
| Enriched ISPs in Annealing Buffer | 8 μL | 15 μL |
| Total volume | 13 μL | 27 μL |

The standard sequencing protocol was then performed as essentially outlined in the Sequencing Kit User Guide.

Denature the Sequencing Polymerase

After the sequencing run was complete, the Ion chip was removed from the PGM™ System and placed on a grounding plate or in an Ion centrifuge adapter/rotor bucket. While the Ion chip was removed, a dummy (used) chip was clamped into the PGM.

100 μL of EDS was applied into the loading port on the Ion chip. The Chip was then incubated at room temperature for 1 minute.

A 1× NEBuffer 2 was prepared by diluting the stock buffer 1:10 with nuclease-free water. An additive, PVP, was also added to the buffer to a final concentration of 0.4%. The chip was then washed three times with 100 μL of 1× NEBuffer 2 containing PVP.

Fill in the Sequence

An extension solution was prepared as follows:

|  | Volume per chip | |
| --- | --- | --- |
| Component | Ion 314™ Chip | Ion 316™ Chip |
| Nuclease-free water | 12 μL | 48 μL |
| 10 mM dNTPs (prepare a 1:4 dilution of stock dNTPs from the Ion Xpress™ Template 200 Kit) | 2 μL | 8 μL |
| PVP 0.4% | 2 μL | 8 μL |
| 10X NEBuffer 2 | 2 μL | 8 μL |
| DNA Polymerase I, Large (Klenow) Fragment | 2 μL | 8 μL |
| Total | 20 μL | 80 μL |

The following volumes of extension solution were applied to the loading port of the respective chip.

Ion 314™ Chip: 15 μl (~5 μl overflow in flow cell wells)

Ion 316™ Chip: 75 μl (~25 μl overflow in flow cell wells)

The chip was then transferred to a covered heating block (at 25° C.) containing a 50 ml tube cap filled with deionized water (to prevent evaporation) and incubated for 10 minutes. After which, 100 ul of EDS was loaded into the loading port, and incubated at room temperature for 1 minute. After incubation, as much liquid as possible was removed from the loading port. A 1× NEBuffer 4 was prepared by diluting the stock buffer 1:10 with nuclease-free water. An additive, PVP, was also added to the buffer to a final concentration of 0.4%. The chip was then washed three times with 100 μL of 1× NEBuffer 4 containing PVP.

Denature the Template

A second strand solution was prepared as outlined below.

|  | Volume per chip | |
| --- | --- | --- |
| Component | Ion 314™ Chip | Ion 316™ Chip |
| Nuclease-free water | 42 μL | 168 μL |
| NEBuffer 4 (1x) | 6 μL | 24 μL |
| Nt.BbvCI | 6 μL | 24 μL |
| T7 Exonuclease | 6 μL | 24 μL |
| Total | 60 μL | 240 μL |

The following amounts of the second strand solution was dispensed into the respective Chip.

Ion 314™ Chip: 15 μl (~5 μl overflow in flow cell wells)

Ion 316™ Chip: 75 μl (~25 μl overflow in flow cell wells)

The chip was placed on a 1.5 ml freezer rack half filled with deionized water and incubated at room temperature for 20 minutes. The fluid in the chip was replaced from the loading port, and the second strand solution was re-applied to the chip for a second and third time, with the respective incubation times for a total incubation time of 60 minutes. After the final incubation, residual liquid was removed from the chip and 100 μl of EDS was applied to the loading port. The chip was incubated at room temperature for 1 minute, after which the EDS solution was removed from the chip.

The chip was then washed 3 times with 100 μl of annealing buffer from the Ion Sequencing 200 Kit.

The sequencing polymerase from the Ion Sequencing 200 Kit was diluted in annealing buffer as shown below:

| Component | Volume per chip | |
|---|---|---|
| | Ion 314 ™ Chip | Ion 316 ™ Chip |
| Sequencing Polymerase | 1.5 μL | 6 μL |
| Annealing Buffer | 6 μL | 24 μL |
| Total volume | 7.5 μL | 30 μL |

Any residual annealing buffer from the wash steps was removed from the chip, and the diluted sequencing polymerase was applied (in full volume) to the loading port and incubated at room temperature for 5 minutes. During incubation, the sequencing key for the PGM system was altered as shown below:

P) From the main screen, press Options.
Q) Press Advanced.
R) Press Change "Library Key Sequence".
S) Enter the new key sequence: TCAGC.
T) Press Back to return to the main screen.

Following incubation, the dummy (used) chip was removed from the PGM system and the prepared paired-end sequencing chip was loaded. The sequencing experiment was initiated via pressing "experiment" on the PGM system. During the chip check, the "wetload" box was unchecked. The chip washing and loading steps provided in the Ion Sequencing 200 Kit were also obviated to proceed directly to selecting the experimental configuration and performance of the sequencing run.

Example 12

In this non-limiting example, a paired-end library was prepared as follows.

Prepare the Paired-End Adaptor Mixture

Paired-End Adaptor oligonucleotides were created to form a paired-end adapter mixture for use in the library preparation. Paired-end P1 Adaptor oligonucleotide 3 and 4 contain an Nt.BbvCI nick site, while Adaptor A oligonucleotides 3 and 4 complete the adaptors mixture. All oligonucleotides were HPLC purified and subjected to sodium salt exchange. In the oligonucleotides * denotes a phosphorothioate bond. In the oligonucleotides "Y" denotes a C or a T nucleotide at that position.

| | |
|---|---|
| Paired-end P1 Adapter oligo 3 | 5'-CCACTACGCCTCCGCTTT CCTCTCTATGGGCAGTCGGTG ATCCTCAGC-3' SEQ ID NO: 7 |
| Paired-end P1 Adapter oligo 4 | 5'-GCTGAGGATCACCGACTG CCCATAGAGAGGAAAGCGGAG GCGTAGYGG*T*T-3' SEQ ID NO: 8 |
| Adapter A oligo 3 | 5'-CCATCTCATCCCTGCGTG TCTCCGACTCAG-3' SEQ ID NO: 4 |
| Adapter A oligo 4 | 5'-CTGAGTCGGAGACACGCA GGGATGAGATGG*T*T-3' SEQ ID NO: 5 |

The following paired-end sequencing primer was ordered and purified as above.

5'-C*C*A*T*CTCATCCCTGCGTGTCTCCGAC-3' (SEQ ID NO: 6), wherein * denotes a phosphorothioate bond.

Prepare Enzyme Denaturation Solution

An enzyme denaturing solution (EDS) was prepared as follows for use in the paired-end library: 10×TE pH 8.0 (5 ml), 20% SDS (5 ml) and 50 mM NaCl (0.5 ml) to a total of 50 ml in nuclease-free water. Final concentration: 1×TE pH 8.0, 2% SDS and 50 mM NaCl. 1.3 ml of EDS was used per sequencing reaction.

Prepare the Paired-End Adaptors Mixture

Each Adaptor oligonucleotide was diluted to a concentration of 100 um with Y μl of nuclease-free water, determined as follows:

$X$ nmole oligo/100 nmole×1000=$Y$ μl of nuclease-free water

The following reactions were prepared in separate sterile tubes:

| | Tube 1 | Tube 2 |
|---|---|---|
| Paired-end P1 Adapter oligo 3 (100 μM) | 50 μL | — |
| Paired-end P1 Adapter oligo 4 (100 μM) | 50 μL | — |
| A Adapter oligo 3 (100 μM) | — | 50 μL |
| A Adapter oligo 4 (100 μM) | — | 50 μL |
| T4 DNA Ligase Buffer (5X) | 25 μL | 25 μL |

Each tube was heated using a thermal cycler as follows:

A) Heat at 90° C. for 2 minutes
B) Cool to room temperature (~120 minutes)

Equal volumes of each adaptor were combined into a single tube to form a complete adaptor mixture at a final concentration of about 20 μM. The complete adaptor mixture was then stored at −20° C. until ready to progress to the next step.

Library Preparation: Substitute the Paired-End Adaptors Mixture

A non-barcoded library was prepared as essentially described in the Ion Plus Fragment Library Kit (Life Technologies, Part No. 4471252), except the standard adaptors of the Ion Plus Fragment Library Kit were substituted with the adaptor mixture prepared above. The library was prepared essentially according to the protocol outlined in the above Library Preparation User Guide, which is incorporated herein in its entirety.

Template Preparation

A standard template protocol was performed as essentially described in the Ion Template Kit User Guide (Life Technologies, Part No. 4469004), which is incorporated herein in its entirety.

Perform Standard Forward Sequencing

A standard sequencing protocol was performed as essentially described in the Ion Sequencing 200 Kit User Guide (Life Technologies, Part No. 4471998), which is incorporated herein in its entirety, except that the standard sequencing primer was substituted for the paired-end sequencing primer, prepared above. The paired-end sequencing primer was added to the Ion Sphere Particles (ISPs) as follows:

|                                    | Volume per chip |              |
| ---------------------------------- | --------------- | ------------ |
| Component                          | Ion 314 ™ Chip  | Ion 316 ™ Chip |
| Paired-end Sequencing Primer       | 5 µL            | 12 µL        |
| Enriched ISPs in Annealing Buffer  | 8 µL            | 15 µL        |
| Total volume                       | 13 µL           | 27 µL        |

The standard sequencing protocol was then performed as essentially outlined in the Sequencing Kit User Guide.

Denature the Sequencing Polymerase

After the sequencing run was complete, the Ion chip was removed from the PGM™ System and placed on a grounding plate or in an Ion centrifuge adapter/rotor bucket. While the Ion chip was removed, a dummy (used) chip was clamped into the PGM.

100 µL of EDS was applied into the loading port on the Ion chip. The Chip was then incubated at room temperature for 1 minute.

A 1× NEBuffer 2 was prepared by diluting the stock buffer 1:10 with nuclease-free water. A detergent, Tween-20 was also added to the buffer to a final concentration of 0.05%. The chip was then washed three times with 100 µL of 1× NEBuffer 2 containing Tween-20.

Fill in the Sequence

An extension solution was prepared as follows:

|                                                               | Volume per chip |              |
| ------------------------------------------------------------- | --------------- | ------------ |
| Component                                                     | Ion 314 ™ Chip  | Ion 316 ™ Chip |
| Nuclease-free water                                           | 13 µL           | 52 µL        |
| 10 mM dNTPs (prepare a 1:4 dilution of stock dNTPs from the Ion Xpress ™ Template 200 Kit) | 2 µL | 8 µL |
| Tween 0.05%                                                   | 1 µL            | 4 µL         |
| 10X NEBuffer 2                                                | 2 µL            | 8 µL         |
| DNA Polymerase I, Large (Klenow) Fragment                     | 2 µL            | 8 µL         |
| Total                                                         | 20 µL           | 80 µL        |

The following volumes of extension solution were applied to the loading port of the respective chip.

Ion 314™ Chip: 15 µl (~5 µl overflow in flow cell wells)
Ion 316™ Chip: 75 µl (~25 µl overflow in flow cell wells)

The chip was then transferred to a covered heating block (at 25° C.) containing a 50 ml tube cap filled with deionized water (to prevent evaporation) and incubated for 10 minutes. After which, 100 ul of EDS was loaded into the loading port, and incubated at room temperature for 1 minute. After incubation, as much liquid as possible was removed from the loading port. A 1× NEBuffer 4 was prepared by diluting the stock buffer 1:10 with nuclease-free water. A detergent, Tween-20, was also added to the buffer to a final concentration of 0.05%. The chip was then washed three times with 100 µL of 1× NEBuffer 4 containing Tween-20.

Denature the Template

A second strand solution was prepared as outlined below.

|                      | Volume per chip |              |
| -------------------- | --------------- | ------------ |
| Component            | Ion 314 ™ Chip  | Ion 316 ™ Chip |
| Nuclease-free water  | 42 µL           | 168 µL       |
| NEBuffer 4 (1x)      | 6 µL            | 24 µL        |
| Nt.BbvCI             | 6 µL            | 24 µL        |
| T7 Exonuclease       | 6 µL            | 24 µL        |
| Total                | 60 µL           | 240 µL       |

The following amounts of the second strand solution was dispensed into the respective Chip.

Ion 314™ Chip: 15 µl (~5 µl overflow in flow cell wells)
Ion 316™ Chip: 75 µl (~25 µl overflow in flow cell wells)

The chip was placed on a 1.5 ml freezer rack half filled with deionized water and incubated at room temperature for 20 minutes. The fluid in the chip was replaced from the loading port, and the second strand solution was re-applied to the chip for a second and third time, with the respective incubation times for a total incubation time of 60 minutes. After the final incubation, residual liquid was removed from the chip and 100 µl of EDS was applied to the loading port. The chip was incubated at room temperature for 1 minute, after which the EDS solution was removed from the chip.

The chip was then washed 3 times with 100 µl of annealing buffer from the Ion Sequencing 200 Kit.

The sequencing polymerase from the Ion Sequencing 200 Kit was diluted in annealing buffer as shown below:

|                        | Volume per chip |              |
| ---------------------- | --------------- | ------------ |
| Component              | Ion 314 ™ Chip  | Ion 316 ™ Chip |
| Sequencing Polymerase  | 1.5 µL          | 6 µL         |
| Annealing Buffer       | 6 µL            | 24 µL        |
| Total volume           | 7.5 µL          | 30 µL        |

Any residual annealing buffer from the wash steps was removed from the chip, and the diluted sequencing polymerase was applied (in full volume) to the loading port and incubated at room temperature for 5 minutes. During incubation, the sequencing key for the PGM system was altered as shown below:

U) From the main screen, press Options.
V) Press Advanced.
W) Press Change "Library Key Sequence".
X) Enter the new key sequence: TCAGC.
Y) Press Back to return to the main screen.

Following incubation, the dummy (used) chip was removed from the PGM system and the prepared paired-end sequencing chip was loaded. The sequencing experiment was initiated via pressing "experiment" on the PGM system. During the chip check, the "wetload" box was unchecked. The chip washing and loading steps provided in the Ion Sequencing 200 Kit were also obviated to proceed directly to selecting the experimental configuration and performance of the sequencing run.

Example 13

In this non-limiting example, a paired-end library was prepared as follows.

Prepare the Paired-End Adaptor Mixture

Paired-End Adaptor oligonucleotides were created to form a paired-end adapter mixture for use in the library preparation. Paired-end P1 Adaptor oligonucleotide 3 and 4 contain an Nt.BbvCI nick site, while Adaptor A oligonucleotides 3 and 4 complete the adaptors mixture. All oligonucleotides were HPLC purified and subjected to sodium salt exchange. In the oligonucleotides * denotes a phosphorothioate bond. In the oligonucleotides "Y" denotes a C or a T nucleotide at that position.

```
Paired-end P1       5'-CCACTACGCCTCCGCTTT
Adapter oligo 3     CCTCTCTATGGGCAGTCGGTG
                    ATCCTCAGC-3'
                    SEQ ID NO: 7

Paired-end P1       5'-GCTGAGGATCACCGACTG
Adapter oligo 4     CCCATAGAGAGGAAAGCGGAG
                    GCGTAGYGG*T*T-3'
                    SEQ ID NO: 8

Adapter A           5'-CCATCTCATCCCTGCGTG
oligo 3             TCTCCGACTCAG-3'
                    SEQ ID NO: 4

Adapter A           5'-CTGAGTCGGAGACACGCA
oligo 4             GGGATGAGATGG*T*T-3'
                    SEQ ID NO: 5
```

The following paired-end sequencing primer was ordered and purified as above.

5'-C*C*A*T*CTCATCCCTGCGTGTCTCCGAC-3' (SEQ ID NO: 6), wherein * denotes a phosphorothioate bond.

Prepare Enzyme Denaturation Solution

An enzyme denaturing solution (EDS) was prepared as follows for use in the paired-end library: 10×TE pH 8.0 (5 ml), 20% SDS (5 ml) and 50 mM NaCl (0.5 ml) to a total of 50 ml in nuclease-free water. Final concentration: 1×TE pH 8.0, 2% SDS and 50 mM NaCl. 1.3 ml of EDS was used per sequencing reaction.

Prepare Additive Solution

A 4% or 8% polyvinylpyrrolidone solution (PVP) was prepared as follows for use in the paired-end library. Dissolve 0.4 grams of PVP40 into 4.8 ml of nuclease-free water to a total volume of 5 ml (8% solution) or dissolve 0.2 grams of PVP40 into 4.8 ml of nuclease-free water to a total volume of 5 ml (4% solution).

Prepare the Paired-End Adaptors Mixture

Each Adaptor oligonucleotide was diluted to a concentration of 100 um with Y μl of nuclease-free water, determined as follows:

$X$ nmole oligo/100 nmole×1000=$Y$ μl of nuclease-free water

The following reactions were prepared in separate sterile tubes:

|  | Tube 1 | Tube 2 |
|---|---|---|
| Paired-end P1 Adapter oligo 3 (100 μM) | 50 μL | — |
| Paired-end P1 Adapter oligo 4 (100 μM) | 50 μL | — |
| A Adapter oligo 3 (100 μM) | — | 50 μL |
| A Adapter oligo 4 (100 μM) | — | 50 μL |
| T4 DNA Ligase Buffer (5X) | 25 μL | 25 μL |

Each tube was heated using a thermal cycler as follows:

A) Heat at 90° C. for 2 minutes

B) Cool to room temperature (~120 minutes)

Equal volumes of each adaptor were combined into a single tube to form a complete adaptor mixture at a final concentration of about 20 μM. The complete adaptor mixture was then stored at −20° C. until ready to progress to the next step.

Library Preparation: Substitute the Paired-End Adaptors Mixture

A non-barcoded library was prepared as essentially described in the Ion Plus Fragment Library Kit (Life Technologies, Part No. 4471252), except the standard adaptors of the Ion Plus Fragment Library Kit were substituted with the adaptor mixture prepared above. The library was prepared essentially according to the protocol outlined in the above Library Preparation User Guide, which is incorporated herein in its entirety.

Template Preparation

A standard template protocol was performed as essentially described in the Ion Template Kit User Guide (Life Technologies, Part No. 4469004), which is incorporated herein in its entirety.

Perform Standard Forward Sequencing

A standard sequencing protocol was performed as essentially described in the Ion Sequencing 200 Kit User Guide (Life Technologies, Part No. 4471998), which is incorporated herein in its entirety, except that the standard sequencing primer was substituted for the paired-end sequencing primer, prepared above. The paired-end sequencing primer was added to the Ion Sphere Particles (ISPs) as follows:

|  | Volume per chip | |
|---|---|---|
| Component | Ion 314 ™ Chip | Ion 316 ™ Chip |
| Paired-end Sequencing Primer | 5 μL | 12 μL |
| Enriched ISPs in Annealing Buffer | 8 μL | 15 μL |
| Total volume | 13 μL | 27 μL |

The standard sequencing protocol was then performed as essentially outlined in the Sequencing Kit User Guide.

Denature the Sequencing Polymerase

After the sequencing run was complete, the Ion chip was removed from the PGM™ System and placed on a grounding plate or in an Ion centrifuge adapter/rotor bucket. While the Ion chip was removed, a dummy (used) chip was clamped into the PGM.

A 1× NEBuffer 2 was prepared by diluting the stock buffer 1:10 with nuclease-free water. An additive, PVP, was also added to the buffer to a final concentration of 0.4%. The chip was then washed three times with 100 µL of 1× NEBuffer 2 containing PVP.

Fill in the Sequence

An extension solution was prepared as follows:

| Component | Volume per chip | |
|---|---|---|
| | Ion 314 ™ Chip | Ion 316 ™ Chip |
| Nuclease-free water | 13 µL | 60 µL |
| 10 mM dNTPs (prepare a 1:4 dilution of stock dNTPs from the Ion Xpress ™ Template 200 Kit) | 2 µL | 8 µL |
| PVP 0.4% | 1 µL | 2 µL |
| 10X NEBuffer 2 | 2 µL | 8 µL |
| DNA Polymerase I, Large (Klenow) Fragment | 2 µL | 2 µL |
| Total | 20 µL | 80 µL |

The following volumes of extension solution were applied to the loading port of the respective chip.

Ion 314™ Chip: 15 µl (~5 µl overflow in flow cell wells)
Ion 316™ Chip: 75 µl (~25 µl overflow in flow cell wells)

The chip was then transferred to a covered heating block (at 25° C.) containing a 50 ml tube cap filled with deionized water (to prevent evaporation) and incubated for 10 minutes. A 1× NEBuffer 4 was prepared by diluting the stock buffer 1:10 with nuclease-free water. An additive, PVP, was also added to the buffer to a final concentration of 0.4%. The chip was then washed three times with 100 µL of 1× NEBuffer 4 containing PVP.

Denature the Template

A second strand solution was prepared as outlined below.

| Component | Volume per chip | |
|---|---|---|
| | Ion 314 ™ Chip | Ion 316 ™ Chip |
| Nuclease-free water | 36 µL | 144 µL |
| NEBuffer 4 (1x) | 6 µL | 24 µL |
| Nt.BbvCl | 6 µL | 24 µL |
| PVP 0.4% | 6 µL | 24 µL |
| T7 Exonuclease | 6 µL | 24 µL |
| Total | 60 µL | 240 µL |

The following amounts of the second strand solution was dispensed into the respective Chip.

Ion 314™ Chip: 15 µl (~5 µl overflow in flow cell wells)
Ion 316™ Chip: 75 µl (~25 µl overflow in flow cell wells)

The chip was placed on a 1.5 ml freezer rack half filled with deionized water and incubated at room temperature for 20 minutes. The fluid in the chip was replaced from the loading port, and the second strand solution was re-applied to the chip for a second and third time, with the respective incubation times for a total incubation time of 60 minutes. After the final incubation, residual liquid was removed from the chip and 100 µl of EDS was applied to the loading port. The chip was incubated at room temperature for 1 minute, after which the EDS solution was removed from the chip.

The chip was then washed 3 times with 100 µl of annealing buffer from the Ion Sequencing 200 Kit.

The sequencing polymerase from the Ion Sequencing 200 Kit was diluted in annealing buffer as shown below:

| Component | Volume per chip | |
|---|---|---|
| | Ion 314 ™ Chip | Ion 316 ™ Chip |
| Sequencing Polymerase | 1.5 µL | 6 µL |
| PVP 0.4% | 1 µL | 3 µL |
| Annealing Buffer | 5 µL | 21 µL |
| Total volume | 7.5 µL | 30 µL |

Any residual annealing buffer from the wash steps was removed from the chip, and the diluted sequencing polymerase was applied (in full volume) to the loading port and incubated at room temperature for 5 minutes. During incubation, the sequencing key for the PGM system was altered as shown below:

Z) From the main screen, press Options.
AA) Press Advanced.
BB) Press Change "Library Key Sequence".
CC) Enter the new key sequence: TCAGC.
DD) Press Back to return to the main screen.

Following incubation, the dummy (used) chip was removed from the PGM system and the prepared paired-end sequencing chip was loaded. The sequencing experiment was initiated via pressing "experiment" on the PGM system. During the chip check, the "wetload" box was unchecked. The chip washing and loading steps provided in the Ion Sequencing 200 Kit were also obviated to proceed directly to selecting the experimental configuration and performance of the sequencing run.

Example 14

Sequencing data obtained on an Ion 314™ Chip (Life Technologies) using the paired-end methods of Example 8 and Example 9 are provided in FIGS. 15A and 15B. Modifying Example 8 to reduce the number of EDS washes during the paired-end sequencing protocol (i.e., Example 9) provided a significant increase in the amount of paired sequencing runs (>75% of reads are paired) and also 80% of the forward reads in the reverse direction were obtained at the same quality.

Example 15

The methodology of Example 9 was further modified to increase the concentration of sequencing polymerase in the paired-end sequencing protocol. S 16 provides data from such analysis using Ion 314™ Chips (Life Technologies). Increasing the concentration of sequencing polymerase (2-fold) was found to result in an increase in paired reads and increase in the quality of reverse reads.

Example 16

The methodology of Example 10 was further modified to increase the concentration of sequencing polymerase in the paired-end sequencing protocol. FIGS. 17A and 17B provide data from such analysis using Ion 314™ Chips (Life Technologies). Increasing the concentration of sequencing polymerase (2-fold) and removing the single EDS wash was found to result in an increase in paired reads and increase in the quality of reverse reads.

Example 17

FIGS. 18A, 18B and 18C provide data obtained from Examples 11 and 12. Example 11 included the presence of an additive in the buffer, while Example 12 included the presence of a detergent in the buffer. The data provided in FIGS. 18A, 18B and 18C were obtained using Ion 314™ Chips (Life Technologies). The introduction of a detergent, such as 0.05% Tween-20, into the sequencing buffer increased paired-reads and quality of reverse reads. Addition of an additive, such as 0.4% PVP, into the sequencing buffer was also found to increase the number of paired reads and quality of reverse reads. PVP or Tween-20 in the sequencing buffer was found to result in >75% loading density of the Ion 314™ Chips.

Example 18

FIGS. 19A, 19B and 19C provide data obtained using the protocols of Example 9, Example 10, or Example 11, using Ion 314™ Chips (Life Technologies). Removing the single EDS wash step from the paired end sequencing protocol was found to result in an increase in paired reads and increase in the quality of reverse reads (Example 9 as compared to Example 10). Additionally, the introduction of an additive, such as 0.4% PVP, was also found to increase the number of paired reads and quality of reverse reads (Example 9 or Example 10 as compared to Example 11).

Example 19

In this example, the sequencing run was a 2×200 base pair paired-end run using a 300 bp insert from a *Rhodopseudomonas palustris* CGA009 Library. FIGS. 20A and 20B provide data from such analysis using Ion 316™ Chips (Life Technologies). FIGS. 20A and 20B provide data obtained using the protocols of Example 9 or Example 11. Reducing or removing the EDS wash steps from the paired end sequencing protocol was found to result in an increase in paired reads and increase in the quality of reverse reads. Additionally, the introduction of an additive, such as 0.4% PVP was also found to increase the number of paired reads and quality of reverse reads.

Example 20

In this example, the sequencing run was a 2×200 base pair paired-end run using a 300 bp insert from a *Rhodopseudomonas palustris* CGA009 Library. FIG. 21 provides data from such analysis using Ion 316™ Chips (Life Technologies). FIG. 21A provides data obtained using the protocol of Example 13. The protocol of Example 13 was also amended to modify the incubation time of the sequencing enzyme from 5 minutes to 30 minutes (FIG. 21B). Increasing the incubation time of the sequencing enzyme from 5 to 30 minutes was found to result in an increase in paired reads and increase in the quality of reverse reads.

Example 21

In this non-limiting example, a paired-end library was prepared as follows.
Prepare the Paired-End Adaptor Mixture
Paired-End Adaptor oligonucleotides were created to form a paired-end adapter mixture for use in the library preparation. Paired-end P1 Adaptor oligonucleotide 3 and 4 contain an Nt.BbvCl nick site, while Adaptor A oligonucleotides 3 and 4 complete the adaptors mixture. All oligonucleotides were HPLC purified and subjected to sodium salt exchange. In the oligonucleotides * denotes a phosphorothioate bond. In the oligonucleotides "Y" denotes a C or a T nucleotide at that position.

| Paired-end P1 Adapter oligo 3 | 5'-CCACTACGCCTCCGCTTT CCTCTCTATGGGCAGTCGGTG ATCCTCAGC-3' SEQ ID NO: 7 |
| Paired-end P1 Adapter oligo 4 | 5'-GCTGAGGATCACCGACTG CCCATAGAGAGGAAAGCGGAG GCGTAGYGG*T*T-3' SEQ ID NO: 8 |
| Adapter A oligo 3 | 5'-CCATCTCATCCCTGCGTG TCTCCGACTCAG-3' SEQ ID NO: 4 |
| Adapter A oligo 4 | 5'-CTGAGTCGGAGACACGCA GGGATGAGATGG*T*T-3' SEQ ID NO: 5 |

The following paired-end sequencing primer was ordered and purified as above.
5'-C*C*A*T*CTCATCCCTGCGTGTCTCCGAC-3' (SEQ ID NO: 6), wherein * denotes a phosphorothioate bond.
Prepare Enzyme Denaturation Solution
An enzyme denaturing solution (EDS) was prepared as follows for use in the paired-end library: 10×TE pH 8.0 (5 ml), 20% SDS (5 ml) and 50 mM NaCl (0.5 ml) to a total of 50 ml in nuclease-free water. Final concentration: 1×TE pH 8.0, 2% SDS and 50 mM NaCl. 1.3 ml of EDS was used per sequencing reaction.
Prepare Additive Solution
A 8% polyvinylpyrrolidone solution (PVP) was prepared as follows for use in the paired-end library. Dissolve 0.4 grams of PVP40 into 4.8 ml of nuclease-free water to a total volume of 5 ml (8% solution).
Prepare the Paired-End Adaptors Mixture
Each Adaptor oligonucleotide was diluted to a concentration of 100 um with Y µl of nuclease-free water, determined as follows:

*X* nmole oligo/100 nmole×1000=*Y* µl of nuclease-free water

The following reactions were prepared in separate sterile tubes:

|  | Tube 1 | Tube 2 |
| --- | --- | --- |
| Paired-end P1 Adapter oligo 3 (100 µM) | 50 µL | — |
| Paired-end P1 Adapter oligo 4 (100 µM) | 50 µL | — |
| A Adapter oligo 3 (100 µM) | — | 50 µL |
| A Adapter oligo 4 (100 µM) | — | 50 µL |
| T4 DNA Ligase Buffer (5X) | 25 µL | 25 µL |

Each tube was heated using a thermal cycler as follows:
A) Heat at 90° C. for 2 minutes
B) Cool to room temperature (~120 minutes)
Equal volumes of each adaptor were combined into a single tube to form a complete adaptor mixture at a final concentration of about 20 µM. The complete adaptor mixture was then stored at −20° C. until ready to progress to the next step.
Library Preparation: Substitute the Paired-End Adaptors Mixture
A non-barcoded library was prepared as essentially described in the Ion Plus Fragment Library Kit (Life Technologies, Part No. 4471252), except the standard adaptors of the Ion Plus Fragment Library Kit were substituted with the adaptor mixture prepared above. The library was prepared essentially according to the protocol outlined in the above Library Preparation User Guide, which is incorporated herein in its entirety.

Template Preparation

A standard template protocol was performed as essentially described in the Ion Template Kit User Guide (Life Technologies, Part No. 4469004), which is incorporated herein in its entirety.

Perform Standard Forward Sequencing

A standard sequencing protocol was performed as essentially described in the Ion Sequencing 200 Kit User Guide (Life Technologies, Part No. 4471998), which is incorporated herein in its entirety, except that the standard sequencing primer was substituted for the paired-end sequencing primer, prepared above. The paired-end sequencing primer was added to the Ion Sphere Particles (ISPs) as follows:

| | Volume per chip | |
|---|---|---|
| Component | Ion 314™ Chip | Ion 316™ Chip |
| Paired-end Sequencing Primer | 5 µL | 12 µL |
| Enriched ISPs in Annealing Buffer | 8 µL | 15 µL |
| Total volume | 13 µL | 27 µL |

The standard sequencing protocol was then performed as essentially outlined in the Sequencing Kit User Guide.

Denature the Sequencing Polymerase

After the sequencing run was complete, the Ion chip was removed from the PGM™ System and placed on a grounding plate or in an Ion centrifuge adapter/rotor bucket. While the Ion chip was removed, a dummy (used) chip was clamped into the PGM.

A 1× NEBuffer 2 was prepared by diluting the stock buffer 1:10 with nuclease-free water. An additive, PVP, was also added to the buffer to a final concentration of 0.4%. The chip was then washed twice with 100 µL of 1× NEBuffer 2 containing PVP.

Fill in the Sequence

An extension solution was prepared as follows:

| | Volume per chip | |
|---|---|---|
| Component | Ion 314™ Chip | Ion 316™ Chip |
| Nuclease-free water | 13 µL | 52 µL |
| 10 mM dNTPs (prepare a 1:4 dilution of stock dNTPs from the Ion Xpress™ Template 200 Kit) | 2 µL | 8 µL |
| PVP 8% | 1 µL | 4 µL |
| 10X NEBuffer 2 | 2 µL | 8 µL |
| DNA Polymerase I, Large (Klenow) Fragment | 2 µL | 8 µL |
| Total | 20 µL | 80 µL |

The following volumes of extension solution were applied to the loading port of the respective chip.

Ion 314™ Chip: 15 µl (~5 µl overflow in flow cell wells)
Ion 316™ Chip: 75 µl (~25 µl overflow in flow cell wells)

The chip was then transferred to a covered heating block (at 25° C.) containing a 50 ml tube cap filled with deionized water (to prevent evaporation) and incubated for 10 minutes. 100 µl of EDS was applied to the loading port. A 1× NEBuffer 4 was prepared by diluting the stock buffer 1:10 with nuclease-free water. An additive, PVP, was also added to the buffer to a final concentration of 0.4%. The chip was then washed twice with 100 µL of 1× NEBuffer 4 containing PVP.

Denature the Template

A second strand solution was prepared as outlined below.

| | Volume per chip | |
|---|---|---|
| Component | Ion 314™ Chip | Ion 316™ Chip |
| Nuclease-free water | 39 µL | 156 µL |
| NEBuffer 4 (10x) | 6 µL | 24 µL |
| Nt.BbvCI | 6 µL | 24 µL |
| PVP 8% | 3 µL | 12 µL |
| T7 Exonuclease | 6 µL | 24 µL |
| Total | 60 µL | 240 µL |

The following amounts of the second strand solution was dispensed into the respective Chip.

Ion 314™ Chip: 15 µl (~5 µl overflow in flow cell wells)
Ion 316™ Chip: 75 µl (~25 µl overflow in flow cell wells)

The chip was placed on a 1.5 ml freezer rack half filled with deionized water and incubated at room temperature for 20 minutes. After incubation, the fluid in the chip was replaced from the loading port, and the second strand solution was re-applied to the chip for a second and third time, with the respective incubation times for a total incubation time of 60 minutes. After the final incubation, residual liquid was removed from the chip and 100 µl of EDS was applied to the loading port. The chip was incubated at room temperature for 1 minute, after which the EDS solution was removed from the chip.

The chip was then washed twice with 100 µl of annealing buffer from the Ion Sequencing 200 Kit, that was supplemented with PVP as follows: annealing buffer from the Ion Sequencing 200 kit (240 µl) was added to 8% PVP40 (12 µl).

Perform Reverse Sequencing

The sequencing polymerase from the Ion Sequencing 200 Kit was diluted in annealing buffer as shown below:

| | Volume per chip | |
|---|---|---|
| Component | Ion 314™ Chip | Ion 316™ Chip |
| Sequencing Polymerase | 1.5 µL | 6 µL |
| Annealing Buffer | 6 µL | 24 µL |
| Total volume | 7.5 µL | 30 µL |

Any residual annealing buffer from the wash steps was removed from the chip, and the diluted sequencing polymerase was applied to the loading port and incubated at room temperature for 5 minutes. For a 314™ Chip, 6 µL of diluted polymerase was added. For a 316™ Chip, 25 µL of diluted polymerase was added. During incubation, the sequencing key for the PGM system was altered as shown below:

EE) From the main screen, press Options.
FF) Press Advanced.
GG) Press Change "Library Key Sequence".
HH) Enter the new key sequence: TCAGC.
II) Press Back to return to the main screen.

Following incubation, the dummy (used) chip was removed from the PGM system and the prepared paired-end sequencing chip was loaded. The sequencing experiment was initiated via pressing "experiment" on the PGM system. During the chip check, the "wetload" box was unchecked. The chip washing and loading steps provided in the Ion Sequencing 200 Kit were also obviated to proceed directly to selecting the experimental configuration and performance of the sequencing run. The sequencing run was performed as described in the Ion Sequencing 200 Kit User Guide Example 22

In this exemplary embodiment, 11 independent paired-end sequencing reactions were performed as outlined in Example 21 with the exception of using 318 Ion Chips (Part No. Sequencing was performed using a PGM sequencer. The forward and reverse sequencing data obtained is provided in the table below. In each independent experiment, the forward read was found to produce over 1 gigabyte (Gb) of sequencing data at AQ20. In some instances, the sum of the forward and reverse read were found to produce over 2 Gb of sequencing data at AQ20

| 318 | AQ20 throughput (Mb) | | | | | | |
|---|---|---|---|---|---|---|---|
| Runs | #1 | #2 | #3 | #4 | #5 | #6 | #7 |
| forward | 1,388.82 | 1,247.06 | 997.64 | 1,237.21 | 1,289.28 | 1,445.38 | 1,341.66 |
| Reverse | 723.44 | 705.02 | 774.2 | 570.23 | 614.14 | 627.88 | 950.27 |
| sum | 2112.26 | 1952.08 | 1771.84 | 1807.44 | 1903.42 | 2073.26 | 2291.93 |

| 318 | AQ20 throughput (Mb) | | | | AQ20 throughput Mean (MB) | AQ17 Read length Mean (bp) |
|---|---|---|---|---|---|---|
| Runs | #8 | #9 | #10 | #11 | | |
| forward | 1204.55 | 1204.55 | 1204.55 | 1289.95 | 1259.15 | 216 |
| Reverse | 901.19 | 618.75 | 669.33 | 783.67 | 721.65 | 166 |
| sum | 2105.74 | 1823.3 | 1873.88 | 2073.62 | 1,980.80 | |

Example 23

In this non-limiting example, a paired-end library was prepared as follows:
Prepare the Paired-End Adaptor Mixture
Paired-End Adaptor oligonucleotides were created to form a paired-end adapter mixture for use in the library preparation. Paired-end P1 Adaptor oligonucleotide 3 and 4 contain an Nt.BbvCI nick site, while Adaptor A oligonucleotides 3 and 4 complete the adaptors mixture. All oligonucleotides were HPLC purified and subjected to sodium salt exchange. In the oligonucleotides * denotes a phosphorothioate bond.

| Paired-end P1 Adapter oligo 3 | 5'-CCACTACGCCTCCGCTTT CCTCTCTATGGGCAGTCGGTG ATCCTCAGC-3' SEQ ID NO: 7 |
|---|---|
| Paired-end P1 Adapter oligo 4 | 5'-GCTGAGGATCACCGACTG CCCATAGAGAGGAAAGCGGAG GCGTAGTGG*T*T-3' SEQ ID NO: 9 |
| Adapter A oligo 3 | 5'-CCATCTCATCCCTGCGTG TCTCCGACTCAG-3' SEQ ID NO: 4 |
| Adapter A oligo 4 | 5'-CTGAGTCGGAGACACGCA GGGATGAGATGG*T*T-3' SEQ ID NO: 5 |

The following paired-end sequencing primer was ordered and purified as above.
5'-C*C*A*T*CTCATCCCTGCGTGTCTCCGAC-3' (SEQ ID NO: 6), wherein * denotes a phosphorothioate bond.
Prepare the Paired-End Adaptors Mixture
Each Adaptor oligonucleotide was diluted to a concentration of 100 um with Y µl of nuclease-free water, determined as follows:

$$X \text{ nmole oligo}/100 \text{ nmole} \times 1000 = Y \text{ µl of nuclease-free water}$$

The following reactions were prepared in separate sterile tubes:

| | Tube 1 | Tube 2 |
|---|---|---|
| Paired-end P1 Adapter oligo 3 (100 µM) | 50 µL | — |
| Paired-end P1 Adapter oligo 4 (100 µM) | 50 µL | — |
| A Adapter oligo 3 (100 µM) | — | 50 µL |
| A Adapter oligo 4 (100 µM) | — | 50 µL |
| T4 DNA Ligase Buffer (5X) | 25 µL | 25 µL |

Each tube was heated using a thermal cycler as follows:
A) Heat at 90° C. for 2 minutes
B) Cool to room temperature (~120 minutes)
Equal volumes of each adaptor were combined into a single tube to form a complete adaptor mixture at a final concentration of about 20 µM. The complete adaptor mixture was then stored at −20° C. until ready to progress to the next step.
Library Preparation: Substitute the Paired-End Adaptors Mixture
A non-barcoded library was prepared as essentially described in the Ion Plus Fragment Library Kit (Life Technologies, Part No. 4471252), except the standard adaptors of the Ion Plus Fragment Library Kit were substituted with the adaptor mixture prepared above. The library was prepared essentially according to the protocol outlined in the above Library Preparation User Guide, which is incorporated herein in its entirety.

Template Preparation

A standard template protocol was performed as essentially described in the Ion Express™ Template 200 Kit (Life Technologies, Part No. 4471253), which is incorporated herein in its entirety. For automated preparation, use the Ion One Touch™ Template Kit (Part No. 4468660).

Perform Standard Forward Sequencing

A standard sequencing protocol was performed as essentially described in the Ion Sequencing 200 Kit User Guide (Life Technologies, Part No. 4471998), which is incorporated herein in its entirety, except that the standard sequencing primer was substituted for the paired-end sequencing primer, prepared above. The paired-end sequencing primer was added to the Ion Sphere Particles (ISPs) as follows:

| Component | Volume per chip | |
|---|---|---|
| | Ion 314 ™ Chip | Ion 316 ™ Chip |
| Paired-end Sequencing Primer | 5 µL | 12 µL |
| Enriched ISPs in Annealing Buffer | 8 µL | 15 µL |
| Total volume | 13 µL | 27 µL |

The standard sequencing protocol was then performed as essentially outlined in the Sequencing Kit User Guide.

Denature the Sequencing Polymerase

After the sequencing run was complete, the Ion chip was removed from the PGM™ System and placed on a grounding plate or in an Ion centrifuge adapter/rotor bucket. While the Ion chip was removed, a dummy (used) chip was clamped into the PGM.

A 1× NEBuffer 2 (Fill-in Buffer) was prepared by diluting the stock buffer 1:10 with nuclease-free water. The chip was then washed twice with 100 µL of 1× NEBuffer 2.

Fill in the Sequence

An extension solution was prepared as follows:

| Component | Ion 318 ™ Chip |
|---|---|
| Nuclease-free water | 51 µL |
| 10 mM dNTPs (prepare a 1:4 dilution of stock dNTPs from the Ion Xpress ™ Template 200 Kit) | 8 µL |
| 5X Fill-in Buffer | 16 µL |
| DNA Polymerase | 5 µL |
| Total | 80 µL |

The following volumes of extension solution were applied to the loading port of the Ion 318™ Chip: 75 µl.

The chip was then transferred to a covered heating block (at 22° C.) containing a 50 ml tube cap filled with deionized water (to prevent evaporation) and incubated for 10 minutes. 100 µl of EDS was applied to the loading port. A 1× NEBuffer 4 was prepared by diluting the stock buffer 1:10 with nuclease-free water. An additive, PVP, was also added to the buffer to a final concentration of 0.4%. The chip was then washed twice with 100 µL of 1× NEBuffer 4 containing PVP.

Denature the Template

A second strand solution was prepared as outlined below.

| Component | Ion 318 ™ Chip |
|---|---|
| Nuclease-free water | 104 µL |
| Second strand buffer 5x | 32 µL |
| Nickase | 24 µL |
| Total | 160 µL |

The following amount of the second strand solution was dispensed into the Ion 318™ Chip: 75 µl.

The chip was placed into a thermocycler at 37° C. and incubated for 15 minutes. After incubation, the fluid in the chip was replaced from the loading port, and the second strand solution was re-applied to the chip for a second time, with the respective incubation time for a total of 30 minutes.

During the second incubation, either a 100 mM DTT solution or a 4 mM TCEP solution was prepared and adding to a 1× NEBuffer 4.

After incubation, the residual liquid was removed from the chip and 100 µl of EDS was applied to the loading port. The chip was incubated at room temperature for 1 minute, after which the EDS solution was removed from the chip. The chip was washed three times with the 1× NEBuffer 4 containing fresh DTT or TCEP. The chip was then incubated at 22° C. for 30 minutes. After incubation, the residual liquid was removed from the chip and 100 µl of EDS was applied to the loading port. The chip was incubated at room temperature for 1 minute.

Perform Reverse Sequencing

The sequencing polymerase from the Ion Sequencing 200 Kit was diluted in annealing buffer as shown below:

| Component | Ion 316 ™ Chip |
|---|---|
| Sequencing Polymerase | 6 µL |
| Annealing Buffer | 26 µL |
| Total volume | 32 µL |

After completing the 1 min incubation, the chip was washed three times with annealing buffer. Any residual annealing buffer from the wash steps was removed from the chip, and the diluted sequencing polymerase was applied to the loading port and incubated at room temperature for 5 minutes.

Following incubation, the dummy (used) chip was removed from the PGM system and the prepared paired-end sequencing chip was loaded. The sequencing experiment was initiated via pressing "experiment" on the PGM system.

Example 24

Comparative data showing the effects of reducing agents DTT or TCEP on T7 exonuclease digestion using the protocol provided in Example 23 is provided in FIG. 22. Sequencing data obtained on a 318™ Ion Chip using 4 mM TCEP and the protocol of Example 23 provided a reverse/forward (%) of greater than 93%.

Example 25

Additional methodologies were evaluated as a means to reduce digestion of the bead-immobilized primer (Primer B)

during exonuclease treatment in exemplary embodiments of the paired end sequencing methods according to the disclosure. It was determined that the following methods can be used to reduce bead-immobilized primer digestion or solid-support immobilized primer digestion during paired end sequencing. As detailed in Example 26, the inclusion of additional phosphorothioate residues into the immobilized primer (primer B) were found to reduce the level of immobilized primer digestion during paired end sequencing. Additionally, the presence of additional phosphorothioate residues in the immobilized primer as compared to the standard immobilized (four phosphorothioate) primer was found to increase sequencing throughput (AQ20), percentage pairing, and percentage reverse/forward reads (FIGS. 23A, 23B, 23C, 23D, 23E and 23F). Thus, the method can be used to improve nucleic acid sequencing throughput and percentage of paired end sequencing reads.

A C18 polyethylene glycol (PEG) linker was also evaluated as a substrate for reducing digestion of the immobilized primer during paired end sequencing. A blunt-ended substrate (Oligo 753) was created and compared to the equivalent substrate with an appended C18 PEG linker (Oligo 777). FIG. 24 shows data obtained during exonuclease incubation of the two oligonucleotide substrates. As can be seen, the presence of a PEG linker did not significantly differ from the data obtained with the blunt ended substrate; however substantial inhibition of exonuclease activity was obtained with the subsequent modifications.

A poly-T stretch of nucleotides appended to Oligo 753 was also evaluated as a substrate for reducing exonuclease digestion of immobilized primers during paired end sequencing. The blunt-ended substrate (Oligo 753) was compared to an equivalent substrate having a poly-T stretch of 5 T nucleotides (Oligo 779). FIG. 25 shows data obtained during exonuclease incubation of the two oligonucleotide substrates. As can be seen, the poly-T stretch of 5 nucleotides reduced exonuclease digestion by about 45%.

A poly-T stretch of 10 or 15 nucleotides appended to Oligo 753 were also evaluated as substrates for reducing exonuclease digestion of immobilized primers during paired end sequencing. The blunt-ended substrate (Oligo 753) was compared to an equivalent substrate appended with a poly-T stretch of 10 T nucleotides (Oligo 783) or a poly-T stretch of 15 nucleotides (Oligo 784). FIG. 26 shows data obtained during exonuclease incubation of the 10 and 15 poly-T substrates as compared to the substrate containing a poly-T stretch of 5 nucleotides (Oligo 779). As can be seen, increasing the length of the poly-T stretch of nucleotides substantially reduces the rate of exonuclease digestion.

Overall, it was observed that an oligonucleotide substrate with a stretch of 10 T nucleotides was hydrolyzed at a rate of about 10% compared to the equivalent blunt-ended substrate.

Example 26

In this example, a comparative paired end sequencing study was undertaken using either the Standard Operating Procedure (SOP) primer that contains four phosphorothioate residues (e.g., SEQ ID NO: 6) or modifying the sequencing primer to include five or six phosphorothioate residues (e.g., SEQ ID NO: 2). The paired end sequencing data obtained with five phosphorothioate residues according to the protocol of Example 23 is presented in FIGS. 23A, 23B, 23C, 23D, 23E and 23F.

Example 27

In this example, a modification to block polymerase extension (e.g., during the fill-in reaction of the paired end sequencing methods) was evaluated. A standard polymerase oligonucleotide substrate was prepared as a control (Oligo 221) and compared against equivalent substrates that either contained: a) a stretch of 5 T nucleotides (Oligo 779); b) a stretch of 15 T nucleotides (Oligo 784); or c) a stretch of 15 T nucleotides preceded by an abasic site (Oligo 786). FIG. 27 shows data obtained during polymerase extension reactions for each oligonucleotide substrate. An abasic site in conjunction with a stretch of 15 T nucleotides was found to significantly block polymerase extension. An exonuclease digestion test was also performed according to Example 25 to evaluate the abasic site/poly-T substrate. It was determined that the abasic site/poly-T substrate did not increase the rate of exonuclease digestion compared to the poly-T 15 nucleotide substrate.

While the principles of the present teachings have been described in connection with specific embodiments, it should be understood clearly that these descriptions are made only by way of example and are not intended to limit the scope of the present teachings or claims. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalents.

What is claimed:

1. A method for generating single-stranded nucleic acids, comprising:
   a) hybridizing a first primer to a nucleic acid molecule;
   b) extending the first primer via polymerization under polymerization conditions, thereby forming an extended first primer product that is complementary to a portion of the nucleic acid molecule;
   c) introducing a nick into a portion of the nucleic acid molecule that is hybridized to the extended first primer product, where the nick includes a free 5' end and a free 3' end in the nucleic acid molecule; and
   d) degrading the nucleic acid molecule from the free 5' end of the nick using a degrading agent, thereby generating a single-stranded extended primer product which remains hybridized to an undegraded portion of the nucleic acid molecule.

2. The method of claim 1, wherein the nucleic acid molecule is a single stranded nucleic acid template.

3. The method of claim 1, wherein the 5' end of the nucleic acid molecule is linked to a solid support.

4. The method of claim 1, wherein the solid support comprises a bead, particle, microparticle, microsphere, slide, flowcell or reaction chamber.

5. The method of claim 1, wherein the nucleic acid molecule includes a scissile linkage.

6. The method of claim 1, wherein the nick is introduced into a portion of the nucleic acid molecule with a nicking enzyme or restriction enzyme.

7. The method of claim 1, wherein the nick is introduced by nicking a scissile linkage within the nucleic acid molecule, wherein the scissile linkage comprises a phosphorothioate linkage, phosphoramidate linkage, photolabile internucleosidic linkage, apurinic tetrahydrofuran site, or uracil base.

8. The method of claim 1, further comprising:
   a) separating the single-stranded extended primer product from the undegraded portion of the nucleic acid molecule;
   b) capturing the separated single-stranded extended primer product onto a solid support; and
   c) sequencing the separated single-stranded extended primer product.

9. The method of claim 8, wherein the solid support comprises a bead, microsphere, nanopore, well, trough, groove, channel, flowcell, microwell, slide or other attachment surface.

* * * * *

SEQUENCE LISTING

<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: Synthetic DNA

<400> SEQUENCE: 1
cctctctatg ggcagtcggt gatcctcagc                30

<210> SEQ ID NO 2

```
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(7)
<223> OTHER INFORMATION: phosphorothioate bond between this location

<400> SEQUENCE: 2
ccatctcatc cctgcgtgtc tccgac                                        26

<210> SEQ ID NO 3
<211> LENGTH: 32
<212> TYPE: DNA
<213> ORGANISM: Artificial Sequence
<220> FEATURE:
<223> OTHER INFORMATION: Synthetic DNA

<400> SEQUENCE: 3
gctgaggatc accgactgcc catagagagg tt                                 32

<210> SEQ ID NO 4
<211> LENGTH: 30
<212> TYPE: DNA
<213> ORGANISM: Artificial Sequence
<220> FEATURE:
<223> OTHER INFORMATION: Synthetic DNA

<400> SEQUENCE: 4
ccatctcatc cctgcgtgtc tccgactcag                                    30

<210> SEQ ID NO 5
<211> LENGTH: 32
<212> TYPE: DNA
<213> ORGANISM: Artificial Sequence
<220> FEATURE:
<223> OTHER INFORMATION: Ssynthetic DNA
<220> FEATURE:
<221> NAME/KEY: misc_feature
<222> LOCATION: (30)..(32)
<223> OTHER INFORMATION: phosphorothioate bond between this location

<400> SEQUENCE: 5
ctgagtcgga gacacgcagg gatgagatgg tt                                 32

<210> SEQ ID NO 6
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(5)
<223> OTHER INFORMATION: phosphorothioate bond between this location

<400> SEQUENCE: 6
ccatctcatc cctgcgtgtc tccgac                                        26

<210> SEQ ID NO 7
<211> LENGTH: 48
<212> TYPE: DNA
<213> ORGANISM: Artificial Sequence
<220> FEATURE:
<223> OTHER INFORMATION: Synthetic DNA

<400> SEQUENCE: 7
```

```
ccactacgcc tccgctttcc tctctatggg cagtcggtga tcctcagc                        48

<210> SEQ ID NO 8
<211> LENGTH: 50
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (46)..(46)
<223> OTHER INFORMATION: "Y" is either a "T" or a "C" nucleotide
<220> FEATURE:
<221> NAME/KEY: misc_feature
<222> LOCATION: (48)..(50)
<223> OTHER INFORMATION: phosphorothioate bond between this location

<400> SEQUENCE: 8
gctgaggatc accgactgcc catagagagg aaagcggagg cgtagyggtt                      50

<210> SEQ ID NO 9
<211> LENGTH: 50
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (48)..(50)
<223> OTHER INFORMATION: phosphorothioate bond between this location

<400> SEQUENCE: 9
gctgaggatc accgactgcc catagagagg aaagcggagg cgtagtggtt                      50
```